US008178509B2

(12) United States Patent
Linden et al.

(10) Patent No.: US 8,178,509 B2
(45) Date of Patent: May 15, 2012

(54) METHOD TO TREAT SICKLE CELL DISEASE

(75) Inventors: Joel M. Linden, Charlottesville, VA (US); Kori Wallace, Charlottesville, VA (US); Robert Alan Figler, Earlysville, VA (US); Jayson M. Rieger, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 202 days.

(21) Appl. No.: 11/673,360

(22) Filed: Feb. 9, 2007

(65) Prior Publication Data
US 2008/0009460 A1 Jan. 10, 2008

Related U.S. Application Data

(60) Provisional application No. 60/772,603, filed on Feb. 10, 2006.

(51) Int. Cl.
*A61K 31/7076* (2006.01)
*C07H 19/167* (2006.01)
(52) U.S. Cl. .................................. 514/46; 536/27.3
(58) Field of Classification Search ................ None
See application file for complete search history.

(56) References Cited

U.S. PATENT DOCUMENTS

| | | | |
|---|---|---|---|
| 3,892,777 A | 7/1975 | Gruenman et al. |
| 4,012,495 A | 3/1977 | Schmiechen et al. |
| 4,193,926 A | 3/1980 | Schmiechen et al. |
| 4,242,345 A | 12/1980 | Brenner et al. |
| 4,448,721 A | 5/1984 | DeLuca et al. |
| 4,559,157 A | 12/1985 | Smith et al. |
| 4,608,392 A | 8/1986 | Jacquet et al. |
| 4,665,074 A | 5/1987 | Amschler |
| 4,695,660 A | 9/1987 | Otte et al. |
| 4,820,508 A | 4/1989 | Wortzman |
| 4,824,660 A | 4/1989 | Angello et al. |
| 4,879,296 A | 11/1989 | Daluge et al. |
| 4,938,949 A | 7/1990 | Borch et al. |
| 4,956,345 A | 9/1990 | Miyasaka et al. |
| 4,965,271 A | 10/1990 | Mandell et al. |
| 4,968,697 A | 11/1990 | Hutchison |
| 4,992,478 A | 2/1991 | Geria |
| 5,070,877 A | 12/1991 | Mohiuddin et al. |
| 5,096,906 A | 3/1992 | Mandell et al. |
| 5,124,455 A | 6/1992 | Lombardo et al. |
| 5,140,015 A | 8/1992 | Olsson et al. |
| 5,189,027 A | 2/1993 | Miyashita et al. |
| 5,272,153 A | 12/1993 | Mandell et al. |
| 5,278,150 A | 1/1994 | Olsson et al. |
| 5,298,508 A | 3/1994 | Jacobson et al. |
| 5,364,862 A | 11/1994 | Spada et al. |
| 5,561,111 A | 10/1996 | Guerrant et al. |
| 5,561,134 A | 10/1996 | Spada et al. |
| 5,565,462 A | 10/1996 | Eitan et al. |
| 5,593,973 A | 1/1997 | Carter |
| 5,593,975 A | 1/1997 | Cristalli |
| 5,593,976 A | 1/1997 | Mongelli et al. |
| 5,665,754 A | 9/1997 | Feldman et al. |
| 5,668,139 A | 9/1997 | Belardinelli et al. |
| 5,696,254 A | 12/1997 | Mansour et al. |
| 5,731,296 A | 3/1998 | Sollevi |
| 5,756,706 A | 5/1998 | Mansour et al. |
| 5,776,940 A | 7/1998 | Daluge et al. |
| 5,854,081 A | 12/1998 | Linden et al. |
| 5,877,180 A | 3/1999 | Linden et al. |
| 5,877,190 A | 3/1999 | Dhainaut et al. |
| 5,932,558 A | 8/1999 | Cronstein et al. |
| 5,998,386 A | 12/1999 | Feldman |
| 6,004,945 A | 12/1999 | Fukunaga |
| RE36,494 E | 1/2000 | Olsson et al. |
| 6,020,321 A | 2/2000 | Cronstein et al. |
| 6,020,339 A | 2/2000 | Perrier et al. |
| 6,034,089 A | 3/2000 | Han et al. |
| 6,060,481 A | 5/2000 | LaNoue et al. |
| 6,117,878 A | 9/2000 | Linden et al. |
| 6,232,297 B1 * | 5/2001 | Linden et al. ............ 514/46 |
| 6,303,619 B1 | 10/2001 | Linden et al. |
| 6,322,771 B1 | 11/2001 | Linden et al. |
| 6,326,359 B1 | 12/2001 | Monaghan et al. |
| 6,332,771 B1 | 12/2001 | Adams et al. |
| 6,339,072 B2 | 1/2002 | Martin et al. |
| 6,350,735 B1 | 2/2002 | Monaghan |
| 6,387,889 B1 | 5/2002 | Endo et al. |
| 6,407,076 B1 | 6/2002 | Box et al. |
| 6,448,235 B1 | 9/2002 | Linden et al. |
| 6,455,510 B1 | 9/2002 | Charles et al. |

(Continued)

FOREIGN PATENT DOCUMENTS

| | | |
|---|---|---|
| BR | 0007864 A | 6/2001 |
| EP | 0488331 A1 | 6/1992 |
| EP | 0488336 A1 | 6/1992 |
| EP | 0488336 B1 | 5/1995 |
| EP | 0700908 A1 | 3/1996 |
| EP | 1110554 A1 | 6/2001 |
| EP | 1194440 A2 | 4/2002 |
| EP | 1150991 B1 | 4/2004 |
| EP | 1194440 B1 | 2/2005 |
| JP | 6299330 A | 5/1987 |

(Continued)

OTHER PUBLICATIONS

The Merck Manual of Diagnosis and Therapy, Seventeenth Edition, published 1999 by Merck Research Laboratories, pp. 245-256.*

(Continued)

*Primary Examiner* — Eric S Olson

(74) *Attorney, Agent, or Firm* — Schwegman, Lundberg & Woessner, P.A.

(57) ABSTRACT

The present invention provides a therapeutic method for treating an inflammatory response caused by a sickle cell crisis, comprising administration of an effective amount of an $A_{2A}$ adenosine receptor agonist. Optionally, the method includes administration of a type IV PDE inhibitor (e.g., rolipram).

11 Claims, 9 Drawing Sheets

U.S. PATENT DOCUMENTS

| | | |
|---|---|---|
| 6,514,949 B1 | 2/2003 | Linden et al. |
| 6,525,032 B2 | 2/2003 | Mantell et al. |
| 6,531,457 B2 | 3/2003 | Linden et al. |
| 6,545,002 B1 | 4/2003 | Linden et al. |
| 6,624,158 B2 | 9/2003 | Mantell et al. |
| 6,670,334 B2 | 12/2003 | Linden |
| 6,936,596 B2 | 8/2005 | Konno et al. |
| 7,160,890 B2 | 1/2007 | Castelhano et al. |
| 7,214,665 B2 | 5/2007 | Linden et al. |
| 7,217,702 B2 | 5/2007 | Beauglehole et al. |
| 7,226,913 B2 | 6/2007 | Linden et al. |
| 7,307,079 B2 | 12/2007 | Den Hartog et al. |
| 7,378,400 B2 | 5/2008 | Rieger et al. |
| 7,396,825 B2 | 7/2008 | Okusa et al. |
| 7,427,606 B2 | 9/2008 | Linden et al. |
| 7,442,687 B2 | 10/2008 | Rieger et al. |
| 7,553,823 B2 | 6/2009 | Zablocki et al. |
| 7,576,069 B2 | 8/2009 | Rieger et al. |
| 7,589,076 B2 * | 9/2009 | Rieger et al. ............ 514/46 |
| 7,605,143 B2 * | 10/2009 | Rieger et al. ............ 514/46 |
| 7,737,127 B2 | 6/2010 | Linden et al. |
| 7,875,595 B2 | 1/2011 | Rieger et al. |
| 7,888,329 B2 | 2/2011 | Rieger et al. |
| 7,989,431 B2 | 8/2011 | Rieger et al. |
| 2001/0027185 A1 | 10/2001 | Linden et al. |
| 2002/0032168 A1 | 3/2002 | Mantrell et al. |
| 2002/0058641 A1 | 5/2002 | Mantell et al. |
| 2002/0072597 A1 | 6/2002 | Mantell et al. |
| 2002/0111327 A1 | 8/2002 | Linden et al. |
| 2003/0013675 A1 | 1/2003 | Yeadon et al. |
| 2003/0060487 A1 * | 3/2003 | Bamdad et al. ............ 514/326 |
| 2003/0162742 A1 | 8/2003 | Linden et al. |
| 2003/0186925 A1 | 10/2003 | Palmer et al. |
| 2003/0186926 A1 | 10/2003 | Linden et al. |
| 2005/0004221 A1 | 1/2005 | Hildebrand et al. |
| 2005/0020532 A1 | 1/2005 | Elzein et al. |
| 2005/0065341 A1 | 3/2005 | Wang et al. |
| 2005/0182018 A1 | 8/2005 | Linden et al. |
| 2005/0261236 A1 | 11/2005 | Okusa et al. |
| 2005/0282831 A1 | 12/2005 | Beauglehole et al. |
| 2006/0030889 A1 | 2/2006 | Ben-Haim et al. |
| 2006/0040888 A1 | 2/2006 | Rieger et al. |
| 2006/0040889 A1 | 2/2006 | Rieger et al. |
| 2006/0052298 A1 | 3/2006 | Guerrant et al. |
| 2006/0100169 A1 | 5/2006 | Rieger et al. |
| 2006/0128652 A1 | 6/2006 | Jagtap et al. |
| 2006/0128708 A1 | 6/2006 | Diamond et al. |
| 2006/0217343 A1 | 9/2006 | Rieger et al. |
| 2007/0027073 A1 | 2/2007 | Rubinstein et al. |
| 2007/0032450 A1 | 2/2007 | Rieger |
| 2007/0072843 A1 | 3/2007 | Wang et al. |
| 2007/0232559 A1 | 10/2007 | Linden et al. |
| 2007/0265440 A1 | 11/2007 | Linden et al. |
| 2008/0027022 A1 | 1/2008 | Linden et al. |
| 2008/0064653 A1 | 3/2008 | Li et al. |
| 2008/0176845 A1 | 7/2008 | Sitaraman et al. |
| 2008/0214581 A1 | 9/2008 | Allen et al. |
| 2008/0262001 A1 | 10/2008 | Kranenburg et al. |
| 2008/0312160 A1 | 12/2008 | Guerrant et al. |
| 2009/0012035 A1 | 1/2009 | Jacobson et al. |
| 2009/0081764 A1 | 3/2009 | Pausch et al. |
| 2009/0118309 A1 | 5/2009 | Beauglehole et al. |
| 2009/0123510 A1 | 5/2009 | Cronstein et al. |
| 2009/0162282 A1 * | 6/2009 | Thompson et al. ............ 424/1.73 |
| 2009/0162292 A1 * | 6/2009 | Thompson et al. ............ 424/9.35 |
| 2009/0170803 A1 | 7/2009 | Linden et al. |
| 2009/0181920 A1 | 7/2009 | Watkins et al. |
| 2009/0253647 A1 | 10/2009 | Rieger et al. |
| 2009/0280059 A1 * | 11/2009 | Rieger et al. ............ 424/1.73 |
| 2009/0298788 A1 * | 12/2009 | Rieger et al. ............ 514/46 |
| 2009/0325967 A1 | 12/2009 | Fairhurst et al. |
| 2010/0152127 A1 | 6/2010 | Linden et al. |
| 2010/0166698 A1 | 7/2010 | Rieger |
| 2011/0136755 A1 | 6/2011 | Rieger et al. |

FOREIGN PATENT DOCUMENTS

| | | |
|---|---|---|
| JP | 06299335 A | 5/1987 |
| JP | 03287537 A | 12/1991 |
| JP | 59197 A | 1/1993 |
| JP | 59198 A | 1/1993 |
| JP | 05025195 A | 2/1993 |
| JP | 05-163294 A2 | 6/1993 |
| JP | 07-508718 | 9/1995 |
| JP | 11335302 A | 12/1999 |
| JP | 20007695 A | 1/2000 |
| JP | 2002536300 | 10/2002 |
| NZ | 530976 | 7/2005 |
| WO | WO-9005526 A1 | 5/1990 |
| WO | WO-9015812 A1 | 12/1990 |
| WO | WO-9109864 A1 | 7/1991 |
| WO | WO-93/22328 A1 | 11/1993 |
| WO | WO-95/11681 A1 | 5/1995 |
| WO | WO-96/02553 A2 | 2/1996 |
| WO | WO-96/04280 A1 | 2/1996 |
| WO | WO-9852611 A1 | 11/1998 |
| WO | WO-98/57651 A1 | 12/1998 |
| WO | WO-99/34804 A1 | 7/1999 |
| WO | WO-99/38877 A2 | 8/1999 |
| WO | WO-99/41267 A1 | 8/1999 |
| WO | WO-99/62518 A1 | 12/1999 |
| WO | WO-99/63938 A2 | 12/1999 |
| WO | WO-99/67263 A1 | 12/1999 |
| WO | WO-99/67264 A1 | 12/1999 |
| WO | WO-99/67265 A1 | 12/1999 |
| WO | WO-99/67266 A1 | 12/1999 |
| WO | WO-0012098 A1 | 3/2000 |
| WO | WO-00/23457 A1 | 4/2000 |
| WO | WO-00/44763 A2 | 8/2000 |
| WO | WO-0044763 A3 | 8/2000 |
| WO | WO-00/72799 A2 | 12/2000 |
| WO | WO-00/78777 A1 | 12/2000 |
| WO | WO-00/78779 A2 | 12/2000 |
| WO | WO-0078774 A3 | 12/2000 |
| WO | WO-00/78774 A2 | 12/2001 |
| WO | WO-01/94368 A1 | 12/2001 |
| WO | WO-02/09701 A1 | 2/2002 |
| WO | WO-02/22630 A1 | 3/2002 |
| WO | WO-02/096462 A1 | 12/2002 |
| WO | WO-03/014137 A1 | 2/2003 |
| WO | WO-03/029264 A2 | 4/2003 |
| WO | WO-03029264 A2 | 4/2003 |
| WO | WO-03029264 A3 | 4/2003 |
| WO | WO-03/086408 A1 | 10/2003 |
| WO | WO-03086408 A1 | 10/2003 |
| WO | WO-03/090733 A1 | 11/2003 |
| WO | WO-2005084653 A2 | 9/2005 |
| WO | WO-2005/097140 A2 | 10/2005 |
| WO | WO-2005/107463 A1 | 11/2005 |
| WO | WO-2006/015357 A2 | 2/2006 |
| WO | WO-2006015357 A3 | 2/2006 |
| WO | WO-2006/023272 A1 | 3/2006 |
| WO | WO-2006/028618 A1 | 3/2006 |
| WO | WO-2007/092936 A2 | 8/2007 |
| WO | WO-2007/092936 C2 | 8/2007 |
| WO | WO-2007/092936 A3 | 8/2007 |
| WO | WO-2007/120972 A2 | 10/2007 |
| WO | WO-2007120972 A3 | 12/2007 |
| WO | WO-2008/124150 A1 | 10/2008 |

OTHER PUBLICATIONS

"STN Database Descriptions", 2006 Chemical Abstracts Catalog, published 2006 by Chemical Abstracts Service, p. 52.*

Silverman, R., The Organic Chemistry of Drug Design and Drug Action, published 1992 by Academic Press, pp. 4-47.*

Ballas, S. K., "Sickle Cell Anaemia: Progress in Pathogenesis and Treatment" Drugs (2002) vol. 62 No. 8 p. 1143-1172.*

Cargnoni et al., "Role of A2A Receptors in the Modulation of Myocardial Reperfusion damage" Journal of Cardiovascular Pharmacology (1999) vol. 33 No. 6, pp. 883-893.*

Sullivan et al., "Cyclic AMP-dependent inhibition of human neutrophil oxidative activity by substituted 2-propynylcyclohexyl adenosine A2A receptor agonists" British Journal of Pharmacology (2001) vol. 132, pp. 1017-1026.*

Auchampach et al., "A3 adenosine receptor agonist IB-MECA reduces myocardial ischemia-reperfusion injury in dogs" Am J Physiol Heart Circ Physiol (2003) vol. 285, pp. H607-H613.*
Kanko et al., "Protective Effects of Clopidogrel on Oxidant Damage in a Rat Model of Acute Ischemia" Tohoku J. Exp. Med. (2005) vol. 205 pp. 133-139.*
Entman et al., "Inflammation in the course of early myocardial ischemia" FASEB Journal (1991) vol. 5 pp. 2529-2537.*
Chemical Abstracts regisrty entries 313348-27-5, 287197-78-6, and 250386-15-3, downloaded from CAS registry Nov. 17, 2010.*
"Chemical Abstracts Registry No. 250386-15-3", (Dec. 9, 1999), 1 pg.
"Chemical Abstracts Registry No. 152918-18-8", (Feb. 10, 1994), 1 pg.
"Chemical Abstracts Registry No. 287179-78-6", (Aug. 24. 2000), 1 pg.
"Chemical Abstracts Registry No. 313348-27-5", (Jan. 10, 2001), 1 pg.
"PCT Application No. PCT/US07/61919, International Search Report mailed Nov. 7, 2007", 3 pgs.
"PCT Application No. PCT/US07/61919, Written Opinion mailed Nov. 7, 2007", 8 pgs.
Abiru, T., et al., "Nucleosides and Nucleotides. 107. 2-(cycloalkylalkynyl)adenosines: Adenosine $A_2$ Receptor Agonists with Potent Antihypertensive Effects", *Journal of Medicinal Chemistry*, 35(12), (Jun. 12, 1992), 2253-2260.
Adah, S. A., "Synthesis of Complex Ethynyladenosines Using Organic Triflic Enolates in Palladium-Catalyzed Reactions: Potential Agonists for the Adenosine $A_2$ Receptor", *Tetrahedron*, 53, (1997) 6747-6754.
Belcher, J. D., et al., "Transgenic Sickle Mice Have Vascular Inflammation", *Blood*, 101(10), (2003), 3953-3959.
Bridges, A. J., et al., "$N^6$-[2-(3,5-Dimethoxyphenyl)-2-(2-Methylphenyl)-Ethyl]Adenosine and Its Uronamide Derivatives. Novel Adenosine Agonists With Both High Affinity and High Selectivity for the Adenosine A2 Receptor", *Journal of Medicinal Chemisty*, 31(7), (Jul. 1988),1282-1285.
Bruns, R. F., "Adenosine Receptors—Roles and Pharmacology", *Biological Actions of Extracellular ATP*, 603, Annals of The New York Academy of Sciences,(1990),211-266.
Bruns, R. F., et al., "Characterization of the $A_2$ Adenosine Receptor Labeled by [$^3$H]NECA in Rat Striatal Membranes", *Molecular Pharmacology*, 29, (1986), 331-346.
Buchanan, G. R., "Sickle Cell Disease", *Hematalogy 2004*, 35-47.
Buster, B., et al., "The Effect of Adenosine Receptor Agonists on Neutrophil Pleocytosis and Blood-Brain Barrier Pathophysiology in Experimental Bacterial Meningitis", *Abstract of the Interscience Conference on Antimicrobial Agents and Chemotherapy*, 37, Abstract No. B-72,(1997),p. 39.
Camaioni, E., et al., "Adenosine receptor agonists: synthesis and □iological evaluation of the diastereoisomers of 2-(3-Hydroxy-3-phenyl-1-propyn-1-yl)NECA", *Bioorganic & Medicinal Chemistry*, 5(12), (Dec. 1997),2267-75.
Cassada, D C., et al., "Adenosine $A_{2A}$ agonist reduces paralysis after spinal cord ischemia: correlation with $A_{2A}$ receptor expression on motor neurons", *Annals of Thoracic Surgery*, 74(3), (Sep. 2002), 846-849; discussion 849-50.
Cassada, D C., et al., "Adenosine $A_{2A}$ analogue ATL-146e reduces systemic tumor necrosing factor-alpha and spinal cord capillary platelet-endothelial cell adhesion molecule-1 expression after spinal cord ischemia", *Journal of Vascular Surgery*, 35(5), (May 2002), 994-998.
Cassada, D C., et al., "Adenosine $A_{2A}$ analogue improves neurologic outcome after spinal cord trauma in the rabbit.", *Journal of Trauma-Injury Infection & Critical Care*, 53(2), (Aug. 2002), 225-229.
Cassada, D C., et al., "Adenosine Analogue Reduces Spinal Cord Reperfusion Injury in a Time-Dependent Fashion", *Surgery*, 130(2), (Aug. 2001), 230-235.
Cassada, D C., et al., "An adenosine $A_{2A}$ agonist, ATL-146e, reduces paralysis and apoptosis during rabbit spinal cord reperfusion.", *Journal of Vascular Surgery*, 34(3), (Sep. 2001), 482-88.

Cassada, D C., et al., "Systemic adenosine $A_{2A}$ agonist ameliorates ischemic reperfusion injury in the rabbit spinal cord", *Annals of Thoracic Surgery*, 72(4), (Oct. 2001), 1245-1250.
Chies, J. A. B., "Sickle Cell Disease: A Chronic Inflammatory Condition", *Medical Hypotheses*, 57(1), (2001), 46-50.
Cristalli, G., "2-Alkynyl Derivatives of Adenosine an Adenosine-5'-N-ethyluronamide as Selective Agonists at $A_2$ Adenosine Receptors", *Journal of Medicinal Chemistry*, 35 (13), (1992), 2363-2368.
Cristalli, G., et al., "2-Alkynyl Derivatives of Adenosine-5'-N-ethyluronamide: Selective A2 Adenosine Receptor Agonists with Potent Inhibitory Activity on Platelet Aggregation", *Journal of Medicinal Chemistry*, 37, (1994),1720-1726.
Cristalli, G., et al., "2-Aralkynyl and 2-Heteroalkynyl Derivatives of Adenosine-5'-N-ethyluronamide as Selective $A_{2A}$ Adenosine Receptor Agonists", *J. Med. Chem.*, 38 (9), (1995),1462-1472.
Cristalli, G., et al., "Characterization of Potent Ligands at Human Recombinant Adenosine Receptors", *Drug Development Research*, 45, Research Overview,(1998),176-181.
Cronstein, B. N., "Adenosine Modulates the Generation of Superoxide Anion by Stimulated Human Neutrophils Via Interaction With a Specific Cell Surface Receptor", *Annals New York Academy of Science*, 451, (1985), 291-314.
Cronstein, B. N., "Adenosine; A Physiologic Modulator of Superoxide Anion Generated by Human Neutrophils. Adenosine Acts Via an $A_2$ Receptor on Human Neutrophils", *Journal of Immunology*, 135 (2), (1985), 1366-1371.
Cronstein, B. N., "Engagement of Adenosine Receptors Inhibits Hydrogen Peroxide ($H_2O_2$) Release by Activated Human Neutrophils", *Clinical Immunology and Immunopathology*, 42(1), (1987), 76-85.
Cronstein, B. N., "Methotrexate Inhibits Leukocyte Influx Into Inflammatory Sites Via The Adenosine ($A^2$) Receptor", *Clinical Research*, 41(2), (1993), p. 244A.
Cronstein, B N., et al., "Neutrophil Adherence to Endothelium is Enhanced Via Adenosine $A_1$ Receptors and Inhibited Via Adenosine $A_2$ Receptors", *The Journal of Immunology*, 148 (7), (1992), 2201-2206.
Cronstein, N. , et al., "Occupancy of Adenosine Receptors Raises Cyclic AMP Alone and in Synergy With Occupancy of Chemoattractant Receptors and Inhibits Membrane Depolarization", *Biochemical Journal*, 252(3), (1988), 709-715.
Cronstein, B. N., "The Adenosine/Neutrophil Paradox Resolved: Human Neutrophils Possess Both $A_1$ and $A_2$ Receptors That Promote Chemotaxis and Inhibits $O_2$ Generation, Respectively", *Journal of Clinical Investigation*, 85 (4), (1990), 1150-1157.
Day, Y. , et al., "$A_{2A}$ adenosine receptors on bone marrow-derived cells protect liver from ischemia-reperfusion injury", *The Journal of Immunology*, 174(8), (2005), 5040-5046.
Day, Y.-J. , et al., "Protection From Ischemic Liver Injury by Activation of $A_{2A}$ Adenosine Receptors During Reperfusion: Inhibition of Chemokine Induction", *American Journal of Physiology Gastrointestinal and Liver Physiology*, 286, (2004), G285-G293.
Day, Y. J., et al., "Renal Protection from Ischemia Mediated by $A_{2A}$ Adenosine Receptors on Bone Marrow-Derived Cells.", *Journal of Clinical Investigation*, 112(6), (2003),883-891.
De La Harpe, J. , "Adenosine Regulates the Respiratory Burst of Cytokine—Triggered Human Neutrophils Adherent to Biological Surfaces", *Journal of Immunology*, 143(2), (1989), 596-602.
De Moraes, V. L., et al., "Effect of Cyclo-Oxygenase Inhibitors and Modulators of Cyclic AMP Formation on Lipopolysaccharide-Induced Neutrophil Infiltration in Mouse Lung", *British Journal of Pharmacology*, 117, (1996), 1792-1796.
De Sarro, G., et al., "Effects of Adenosine Receptor Agonists and Antagonists on Audiogenic Seizure-Sensible DBA/2 Mice", *European Journal of Pharmacology*, 371 (1999), 137-145.
De Zwart, M., et al., "5-N-Substituted Carboxamidoadenosines as Agonists for Adenosine Receptors", *Journal of Medicinal Chemistry*, 42(8), (Apr. 22, 1999),1384-1392.
Elzein, E., et al., "Design, Synthesis and Biological Evaluation Of 2-(4-Substituted-N-Pyrazolyl)-Adenosine Derivatives As Novel Short Acting Adenosine A2A Receptor Agonists", *Drug Develop-*

*ment Research*, 50 (1), Abstracts From Purines 2000: Biochemical, Pharmacological, and Clinical Perspectives: Abstract No. 061,(May 2000), p. 64.

Fabry, M. E., et al., "High Expression of Human $\beta^S$- and $\alpha$-globins in Transgenic Mice: Hemoglobin Composition and Hematological Consequences", *Proc. Natl. Acad. Sci. USA*, 89 (1992), 12150-12154.

Fang, G. D., et al., "DWH146e (DWH), A New Selective Adenosine A2a Receptor Agonist, Improves Survival in *E. coli* O26:B6 Lipopolysaccharide (LPS)-Induced Experimental Murine Endotoxemia",*Journal of Investigative Medicine*, Abstract No. 797,(2000),p. 148A.

Fenster, M. S., et al., "Activation of adenosine $A_{2\alpha}$ receptors inhibits mast cell degranulation and mast cell-dependent vasoconstriction", *Microcirculation*, 7(2), (Apr. 2000), 128-135.

Firestein, G. S., "Adenosine Regulating Agents: A Novel Approach to Inflammation and Inflammatory Arthritis", *Clinical Research*, 41(2), (1993),170A.

Fiser, S M., et al., "Adenosine $A_{2A}$ receptor activation decreases reperfusion injury associated with high-flow reperfusion.", *Journal of Thoracic & Cardiovascular Surgery*, 124(5), (Nov. 2002), 973-978.

Francis, J. E., "Highly Selective Adenosine $A_2$ Receptor Agonists in a Series of N-Alkylated 2-Aminoadenosines", *Journal of Medicinal Chemistry*, 34 (8), (1991),pp.2570-2579.

Frenette, P. S., "Sickle Cell Vasoocclusion: Heterotypic, Multicellular Aggregations Driven by Leukocyte Adhesion", *Microcirculation*, 11, (2004), 167-177.

Glover, D. K., et al., "Bolus Injection of DWH-146E, A Novel Adenosine A2A Receptor Agonist for Use in Vasodilator Stress Imaging", *Journal of Nuclear Cardiology*, 7 (4), Abstract No. 44.20,(Sep. 23, 2000), 1 page.

Glover, D. K., et al., "Characterization of a New, Highly Selective Adenosine $A_{2A}$ Receptor Agonist with Potential Use in Pharmacologic Stress Perfusion Imaging", *Circulation*, 100, Abstract,(1999), 1 pg.

Glover, D K., et al., "Pharmacological stress myocardial perfusion imaging with the potent and selective $A_{2A}$ adenosine receptor agonists ATL193 and ATL146e administered by either intravenous infusion or bolus injection", *Circulation*, 104(10), (Sep. 4, 2001),1181-1187.

Glover, D. K., et al., "Pharmacological stress thallium scintigraphy with 2-cyclohexylmethylidenehydrazinoadenosine (WRC-0470). A novel, short-acting adenosine $A_{2A}$ receptor agonist.", *Circulation*, 94(7), (Oct. 1, 1996),1726-1732.

Glover, D. K., et al., "Vasodilator Stress Imaging Using New Adenosine $A_{2A}$ Receptor Agonists Administered by Bolus Injection", *J. Am. Coll. Cardiol.*, 35, Abstract,(2000), 1 pg.

Griswold, D. E., et al., "Effect of Selective Phosphodieasterase Type IV Inhibitor, Rolipram, on Fluid and Cellular Phases of Inflammatory Response", *Inflammation*, 17(3), (1993), 333-344.

Harada, N., et al., "Adenosine and Selective $A_{2A}$ Receptor Agonists Reduce Ischemia/Reperfusion Injury of Rat Liver Mainly by Inhibiting Leukocyte Activation", *The Journal of Pharmacology and Experimental Therapeutics*, 294(3), (2000),1034-1042.

Haskó, G., et al., "Adenosine Inhibits IL-12 and TNF-$_\alpha$ Production via Adenosine $A_{2a}$ Receptor-Dependent and Independent Mechanisms", *The FASEB Journal*, 14, (2000), 2065-2074.

Hebbel, R. P., et al., "Special Issue of *Microcirculation*: Examination of the Vascular Pathobiology of Sickle Cell Anemia", *Microcirculation*, 11 (2004), 99-100.

Hebbel, R. P., et al., "The Endothelial Biology of Sickle Cell Disease: Inflammation and a Chronic Vasculopathy", *Microcirculation*, 11, (2004), 129-151.

Heller, L. J., et al., "Effect of Adenosine on Histamine Release and Atrioventricular Conduction During Guinea Pig Cardiac Anaphylaxis", *Circulation Research*, 62(6), (Jun. 1988),1147-1158.

Homma, H , et al., "Nucleosides and nucleotides. 112. 2-(1-Hexyn-1-yl)adenosine -5'-uronamides: a new entry of selective $A_2$ adenosine receptor agonists with potent antihypertensive activity.", *Journal of Medicinal Chemistry*, 35(15), (Jul. 1992), 2881-2890.

Hussain, T. , et al., $^{125}$I-APE Binding to Adenosine Receptors in Coronary Artery: Photoaffinity Labeling With $^{125}$1-azidoAPE, *The Journal of Pharmacology and Experimental Therapeutics*, 276 (1), (Jan. 1996), 284-288.

Hutchison, A. J., "2-(Arylalkylamino)Adenosine-5'-Uronamides: A New Class of Highly Selective Adenosine $A_2$Receptor Ligands", *Journal of Medicinal Chemistry*, 33 (7), (1990), 1919-1924.

Hutchison, A. J., "CGS 21680C, an $A_2$ Selective Adenosine Receptor Agonist With Preferential Hypotensive Activity", *The Journal of Pharmacology and Experimental Therapeutics*, 251 (1), (1989), 47-55.

Iannone, M. A., "Effects of Adenosine on Human Neutrophil Function and Cyclic AMP Content", In: *Topics and Perspectives in Adenosine Research*, Eds. E. Gerlach et al., Springer-Verlag, Berlin, Germany,(1986),pp. 286-298.

Ishiwata, K. , et al., "Further Characterization of a CNS Adenosine A2a Receptor Ligand [11C]KF18446 with in vitro Autoradiography and in vivo Tissue Uptake", *Annals of Nuclear Medicine*, 14 (2), Abstract Only, Obtained from Chemicals Abstracts, 133, Abstract No. 346544, HCAPlus Accession No. 480897 (2000),81-89.

Jarvis, M. F., "[$^3$H]CGS 21680, A Selective $A_2$ Adenosine Receptor Agonist Directly Labels $A_2$ Receptors in Rat Brain.", *Journal of Pharmacology and Experimental Therapeutics*, 251(3), (Dec. 1989),888-893.

Jordan, J. E., et al., "Adenosine $A_2$ Receptor Activation Attenuates Reperfusion Injury by Inhibiting Neutrophil Accumulation, Superoxide Generation and Coronary Endothelial Adherence", *The Journal of Pharmacology and Experimental Therapeutics*, 280(1), (1997), 301-309.

Kaminuma, O. , et al., "Effect of T-440, a Novel Type IV Phosphodiesterase Inhibitor, on Allergen-Induced Immediate and Late Asthmatic Reaction and Leukocyte Infiltration into the Airways of Guinea Pigs", *International Archives of Allergy & Immunology*, 112(4), (1997), 406-411.

Kaul, D. K., et al., "Anti-Inflammatory Therapy Ameliorates Leukocyte Adhesion and Microvascular Flow Abnormalities in Transgenic Sickle Mice", *American Journal of Physiology—Heart and Circulatory Physiology*, 287, (2004),H293-H301.

Kaul, D. K., et al., "Hypoxia/Reoxygenation Causes Inflammatory Response in Transgenic Sickle Mice But Not in Normal Mice", *The Journal in Clinical Investigation*, 106(3), 411-420, (2000).

Koshiba, M. , "Patterns of $A_{2A}$ Extracellular Adenosine Receptor Expression in Different Functional Subsets of Human Peripheral T Cells", *The FASEB Journal*, Abstract No. 703.38, (1999), p. A944.

Koshiba, M , et al., "Patterns of $A_{2A}$ Extracellular Adenosine Receptor Expression in Different Functional Subsets of Human Peripheral T Cells. Flow Cytometry Studies With Anti-$A_{2A}$ Receptors Monoclonal Antibodies.", *Molecular Pharmacology*, 55 (3), (Mar. 1999), 614-624.

Lappas, C. M., et al., "$A_{2A}$ adenosine receptor induction inhibits IFN-gamma production in murine CD4$^+$ T cells", *Journal of Immunology*, 174(2), (Jan. 15, 2005),1073-1080.

Lard, L. R., et al., "Neutrophil Activation in Sickle Cell Disease", *Journal of Leukocyte Biology*, 66, (1999), 411-415.

Linden, J. , et al., "($^{125}$I)Aminobenzyladenosine, a New Radioligand with Improved Specific Binding to Adenosine Receptors in Heart", *Circulation Research*, 56 (2), (Feb. 1985),279-284.

Linden, J. , "Allosteric Enhancement of Adenosine Receptors", In: *Purinergic Approaches in Experimental Therapeutics*, Chapter 5, Edited by K.A. Jacobson et al., and Published by Wiley-Liss, Inc., (1997),pp. 85-97.

Linden, J. , et al., "Chapter 2—Adenosine Receptors", In: *Handbook of Receptors and Channels—G Protein Coupled Receptors*, Peroutka, S. J., Editor, CRC Press, Boca Raton, FL,(1994),29-44.

Linden, J. , "Molecular Approach to Adenosine Receptors: Receptor-Mediated Mechanisms of Tissue Protection", *Annual Review of Pharmacology and Toxicology*, 41, (2001),775-787.

Link, A. A., et al., "Ligand-Activation of the Adenosine $A_{2a}$ Receptors Inhibits IL-12 Production by Human Monocytes", *The Journal of Immunology*, 164, (2000), 436-442.

Lum, A. F. H., et al., "Inflammatory Potential of Neutrophils Detected in Sickle Cell Disease", *American Journal of Hematology*, 76 (2004), 126-133.

Luthin, D. R., et al., "Adenosine Receptors", *Biomembranes*, 2B, (1996),pp. 321-347.

Luthin, D. R., "Characterization of Two Affinity States of Adenosine $A_{2a}$ Receptors With a New Radioligand, 2-[2-(4-amino-3-[$^{125}$I]iodophenyl) Ethylamino]Adenosine.", *Molecular Pharmacology*, 47 (2), (Feb. 1995), 307-313.

Luthin, D. R., et al., "Comparison of $A_4$ and $A_{2a}$ Binding Sites in Striatum and COS Cells Transfected With Adenosine $A_{2a}$ Receptors.", *The Journal of Pharmacology and Experimental Therapeutics*, 272, (1995), 511-518.

Luthin, D. R., et al., "Photoaffinity Labeling With 2(−)[2-(4-Azido-3(−)[$^{125}$I]-Iodophenyl)ethylamino]adenosine and Autoradiography With 2-[2-(4-Amino-3-[$^{125}$I]Iodophenyl)ethylamino]adenosine of $A_{2a}$ Adenosine Receptors in Rat Brain.", *Journal of Neurochemistry*, 65(5), (1995), 2072-2079.

Mager, Peter. P., "Neural network approaches applied to selective $A_{2a}$ adenosine receptor agonists", *Med. Chem. Res.*, 8(6), (1998), 277-290.

Martin, P. L., et al., "Pharmacology of 2-cyclohexylmethylidenehydrazinoadenosine (WRC-0470), a Novel, Short-acting Adenosine $A_{2A}$ Receptor Agonist That Produces Selective Coronary Vasodilation.", *Drug Development Research*, 40 (4), (1997), 313-324.

McGarrity, S. T., "Regulation of Human Neutrophil Function by Adenine Nucleotides", *Journal of Immunology*, 142(6), (1989), 1986-1994.

McPherson, J A., "Adenosine $A_{2A}$ receptor stimulation reduces inflammation and neointimal growth in a murine carotid ligation model", *Arteriosclerosis, Thrombosis & Vascular Biology*, 21(5), (May 2001), 791-796.

McPherson, J. A., et al., "Effect of Prolonged Adenosine $A_{2A}$ Receptor Activation on Neointimal Formation in the Injured Mouse Carotid Artery", *The FASEB Journal*, Abstract No. 299.2, (1999),A367.

McPherson, J. A., et al., "Prolonged Adenosine $A_{2a}$ Receptor Stimulation Reduces Inflammation and Neointima Formation in a Murine Carotoid Ligation Model", *Supplement to Circulation*, 100 (18), Abstract No. 3652,(Nov. 2, 1999), 1 page.

Moore, C. C., et al., "$A_{2A}$ Adenosine Receptor Agonists Modify Inflammatory Responses in an *E. coli* Peritonitis Murine Septic Shock Model", *Proceeding of the 43$^{rd}$ Annual Meeting of the Infectious Disease Society of America*, Abstract No. 52, San Francisco,(Oct. 6-9, 2005), p. 43.

Morabito, L. , et al., "Methotrexate and Sulfasalazine Promote Adenosine Release by a Mechanism that Requireds Ecto-5'-Nucleotidase-Mediated Conversion of Adenine Nucleotides", *Journal of Clinical Investigation*, 101(2), (1998),295-300.

Murphree, L. J., et al., "Human $A_{2A}$ Adenosine Receptors: High-Affinity Agonist Binding to Receptor-G Protein Complexes Containing $G\beta^{4}$", *Molecular Pharmacology*, 61(2), (2002), 455-462.

Nagel, R. L., et al., "The Panoply of Animal Models for Sickle Cell Anaemia", *British Journal of Haematology*, 112 (2001), 19-25.

Needleman, J. P., et al., "Breathing Patterns During Vaso-occlusive Crisis of Sickle Cell Disease", *Chest*, 122, (2002), 43-46.

Nielson, C. P., "Effects of Adenosine on Polymorphonuclear Leucocyte Function, Cyclic 3': 5'-adenosine Monophosphate, and Intracellular Calcium", *British Journal of Pharmacology*, 97(3) (1989),882-888.

Niiya, K., "2-(N'-Alkylidenehydrazino)Adenosines: Potent and Selective Coronary Vasodilators", *Journal of Medicinal Chemistry*, 35(24), (1992), 4557-4561.

Nolte, D. , et al., "Reduction of Postischemic Leukocyte-Endothelium Interaction by Adenosine Via $A_2$ Receptor", *Naunyn-Schmiedeberg's Archives of Pharmacology*, 346(2), (1992), 234-237.

O'Regan, M. H., et al., "Adenosine Receptor Agonists Inhibit the Release of γ-Aminobutyric Acid (GABA) From the Ischemic Rat Cerebral Cortex", *Brain Research*, 582(1), (1992),22-26.

Okusa, M D., et al., "$A_{2A}$ Adenosine Receptor-Mediated Inhibition of Renal Injury and Neutrophil Adhesion",*American Journal of Physiology—Renal Fluid & Electrolyte Physiology*, 279(5), (2000), F809-F818.

Okusa, M D., et al., "Enhanced Protection from Renal Ischemia: Reperfusion Injury With $A_{2A}$-Adenosine Receptor Activation and PDE 4 Inhibition", *Kidney International*, 59(6), (2001), 2114-2125.

Okusa, M. D., et al., "Selective $A_{2A}$ adenosine receptor activation reduces Ischemia-reperfusion injury in rat kidney", *Am. J. Physiol.*, vol. 277 (3, Pt 2), (1999),F404-F412.

Olah, M. E., et al., "Adenosine Receptor Subtypes: Characterization and Therapeutic Regulation", *Annual Review of Pharmacology and Toxicology*, 35, (1995),581-606.

Olsson, R. A., et al., "$N^6$ Substituted N-Alkyladenosine-5'-Uronamides: Bifunctional Ligands Having Recognition Groups for $A_1$ and $A_2$ Adenosine Receptors", *Journal of Medicinal Chemistry*, 29 (9), (1986), 1683-1689.

Orringer, E. P., et al., "Purified Polosamer 188 for Treatment of Acute Vaso-occusive Crisis of Sickle Cell Disease", *JAMA*, 286(17), 2099-2106.

Pathare, A., et al., "Cytokines in Sickle Cell Disease", *Hematology*, 8(5), (2003), 329-337.

Peart, J., et al., "Adenosine-mediated cardioprotection in ischemic-reperfused mouse heart.", *Journal of Cardiovascular Pharmacology*, 39(1), (Jan. 2002),117-129.

Peet, N. P., et al., "Conformationally Restrained, Chiral (Phenylisopropyl)Amino-Substituted Pyrazolo[3,4-d]Pyrimidines and Purines With Selectivity for Adenosine $A_1$ and $A_2$ Receptors", *Journal of Medicinal Chemistry*, 35 (17), (1992),3263-3269.

Peirce, S. M., et al., "Attenuation of I/R Injury in Skin Using A Selective $A_{2A}$ Adenosine Receptor Agonist", *FASEB Journal*, 14 (4), Abstract No. 333.1,(Mar. 15, 2000), p. A466.

Peirce, S M., "Selective $A_{2A}$ adenosine receptor activation reduces skin pressure ulcer formation and inflammation", *American Journal of Physiology—Heart & Circulatory Physiology*, 281(1), (Jul. 2001), H67-H74.

Pflueger, A. C., et al., "Adenosine-Induced Renal Vasoconstriction in Diabetes Mellitus Rats: Role of Nitric Oxide", *Am. J. Physiol. Renal Physiol.*; 276, (1999), F340-346.

Platt, O. S., et al., "Pain in Sickle Cell Disease", *New England Journal of Medicine*, 325(1), (1991), 11-16.

Platt, O. S., "Sickle Cell Anemia as an Inflammatory Disease", *The Journal of Clinical Investigation*, 106 (3), (2000), 337-338.

Pulle, V. , et al., "Design, Synthesis and Pharmacological Evaluation of 2(1-Alkyl-Pyrazol-4-YL) Adenosine Derivatives As Short Acting Adenosine A2A Receptor Agonists", *Drug Development Research*, 50 (1), Abstracts From Purines 2000: Biochemical, Pharmacological and Clinical Perspectives: Abstract No. 062,(May 2000), p. 64.

Rashad, S., et al., "Effect of Non-Steroidal Anti-Inflammatory Drugs on the Course of Osteoarthritis", *The Lancet*,2(8662), (Sep. 2, 1989),519-522.

Rieger, J. M., et al., "Design, Synthesis, and Evaluation of Novel $A_{2A}$ Adenosine Receptor Agonists", *Journal of Medicinal Chemistry*, 44(4), (2001), 531-539.

Riou, L M., et al., "Influence of propranolol, enalaprilat, verapamil, and caffeine on adenosine $A_{2A}$-receptor-mediated coronary vasodilation", *Journal of the American College of Cardiology*, 40(9), (Nov. 6, 2002), 1687-1694.

Roberts, P. A., et al., "Inhibition by Adenosine of Reactive Oxygen Metabolite Production by Human Polymorphonuclear Leucocytes", *Biochemical Journal*, 227(2), (1985),669-674.

Robeva, A. S., et al., "Double Tagging Recombinant $A_1$- and $A_{2A}$-Adenosine Receptors With Hexahistidine and the FLAG Epitope. Development of an Efficient Generic Protein Purification Procedure.", *Biochemical Pharmacology*, 51(4), (Feb. 1996), 545-555.

Robeva, A. S., et al., "Molecular Characterization of Recombinant Human Adenosine Receptors", *Drug Development Research*, 39, (1996), 243-252.

Rosin, D. L., et al., "Immunohistochemical Localization of Adenosine $A_{2A}$ Receptors in the Rat Central Nervous System", *The Journal of Comparative Neurology*, 401, (1998),pp. 163-186.

Ross, S. D., et al., "Selective Adenosine-A2A Activation Reduces Lung Reperfusion Injury Following Transplantation",*Journal of Heart and lung transplantation*, 18 (1), Abstract Only, Proceedings of the Nineteenth Annual Meeting and Scientific Sessions of the International Society for Heart and Lung Transplantation, San Francisco, CA,(Jan. 1999),p. 72.

Ross, S D., et al., "Selective Adenosine-$A_{2A}$ Activation Reduces Lung Reperfusion Injury Following Transplantation", *Journal of Heart & Lung Transplantation*, 18(10), (1999),994-1002.

Saunthararajah, Y., et al., "Effects of 5-aza-2'-deoxycytidine on Fetal Hemoglobin Levels, Red Cell Adhesion, and Hematopoietic Differentiation in Patients With Sickle Cell Disease", *Blood*, 102(12), (2003), 3865-3870.

Schiffmann, S. N., et al., "Distribution of adenosine $A_2$ receptor mRNA in the human brain", *Neuroscience Letters*, 130, (1991), 177-181.

Schlack, W., et al., "Adenosine $A_2$-Receptor Activation at Reperfusion reduces Infarct Size and Improves Myocardial Wall Function in Dog Heart", *Journal of Cardiovascular Pharmacology*, 22, (1993), 89-96.

Schrier, D. J., et al., "The Effects of Adenosine Agonists on Human Neutrophil Function", *Journal of Immunology*, 137 (10), (1986), 3284-3289.

Shapiro, B. S., "The Management of Pain in Sickle Cell Disease", *Pediatric Clinics of North America*, 36(4), (1989), 1029-1041.

Sheardown, M. J., "Unexpected Neuroprotection Observed with the Adenosine $A_{2A}$ Receptor Agonist CGS 21860", *Drug Development Research*, 39, (1996), 108-114.

Sipka, S., "Adenosine Induced Delay of Expression of AIDS Virus, HIV, in H9T Cells", *Acta. Biochimica et Biophysica Hungarica*, 23(1), (1988), 75-82.

Smits, P., et al., "Cardiovascular effects of two xanthines and the relation to adenosine antagonism", *Clinical Pharmacology and Therapeutics*, 45 (6), (1989), 593-599.

Solovey, A., et al., "Circulating Activating Endothelial Cells in Sickle Cell Anemia", *The New England Journal of Medicine*, 337(22), (1997), 1584-1590.

Solovey, A., et al., "Tissue Factor Expression by Endothelial Cells in Sickle Cell Anemia", *Journal of Clinical Investigation*, 101(9), (1998), 1899-1904.

Steinberg, M. H., et al., "Effect of Hydroxyurea on Mortality and Morbidity in Adult Sickle Cell Anemia", *JAMA*, 289(13), (2003), 1645-1651.

Stuart, M. J., et al., "Sickle Cell Disease", *The Lancet*, 364, (2004), 1343-1360.

Sullivan, G. W., "$A_{2A}$ Adenosine Receptor Activation Improves Survival in Mouse Models of Endotoxemia and Sepsis", *Journal of Infectious Diseases*, 189(10), (May 15, 2004), 1897-1904.

Sullivan, G. W., "Adenosine (ADO) Modulates Endotoxin and TNF-Induced PMN Activation", *Clinical Research*, 41(2), (1993), 172A.

Sullivan, G.W., et al., "Cyclic AMP-Dependent Inhibition of Human Neutrophil Oxidative Activity by Substitued 2-Propynylcyclohexyl Adenosine $A_{2A}$ Receptor Agonists", *British Journal of Pharmacology*, 132(5), (2001), 1017-1026.

Sullivan, G. W., et al., "Neutrophil $A_{2A}$ Adenosine Receptor Inhibits Inflammation in a Rat Model of Meningitis: Synergy with the Type IV Phosphodiesterase Inhibitor, Rolipram", *The Journal of Infectious Diseases*, 180, No. 5, (1999), 1550-1560.

Sullivan, G. W., et al., "Role of $A_{2A}$ Adenosine Receptors in Inflammation", *Drug Development Research*, 45 (3/4), (1998), 103-112.

Sullivan, G. W., et al., "The role of inflammation in vascular diseases", *Journal of Leukocyte Bilogy*, 67, (May 2000), pp. 591-602.

Sullivan, G. W., et al., "The Specific Type IV Phosphodiesterase Inhibitor Rolipram Combined with Adenosine Reduces Tumor Necrosis Factor-α-Primed Neutrophil Oxidative Activity", *International Journal of Immunopharmacology*, 17(10), (1995), 793-803.

Takiguchi, Y., et al., "Early adminstration of YT-146, an adenosine $A_2$ receptor agonist, inhibits neointimal thickening after rat femoral artery endothelium injury", *European Journal of Pharmacology 281* (1995), 205-207.

Turhan, A., et al., "Primary Role for Adherent Leukocytes in Sickle Cell Vascular Occlusion: A New Paradigm", *Proc. Natl. Acad. Sci. USA*, 99(5), (2002), 3047-3051.

Ueeda, M., et al., "2-Alkoxyadenosines: Potent and Selective Agonists at the Coronary Artery $A_2$ Adenosine Receptor", *Journal of Medicinal Chemistry*, 34(4), (1991), 1334-1339.

Underwood, D. C., et al., "Inhibition of Antigen-Induced Bronchoconstriction and Eosinophil Infiltration in the Guinea by the Cyclic AMP-Specific Phosphodiesterase Inhibitor, Rolipram", *The Journal of Pharmacology and Experimental Therapeutics*, 266(1), (1993), 306-313.

Van Calker, D., et al., "Adenosine Regulates via Two Different Types of Receptors, the Accumulation of Cyclic Amp in Cultured Brain Cells", *Journal of Neurochemistry*, 33, (1979), pp. 999-1005.

Van Calker, D., et al., "Carbamazepine Distinguishes Between Adenosine Responses That Mediate Different Second Messenger Responses", *European Journal of Pharmacology*, 206 (4), (1991), 285-290.

Vittori, S, et al., "2-alkenyl and 2-alkyl derivatives of adenosine and adenosine-5'-N-ethyluronamide: different affinity and selectivity of E- and Z-diasteromers at $A_{2A}$ adenosine receptors.", *Journal of Medicinal Chemistry*, 39(21), (Oct. 1996), 4211-4217.

Volpini, R., et al., "Synthesis of Di- and Tri-Substituted Adenosine Derivatives and Their Affinities at Human Adenosine Receptor Subtypes", *Nucleosides & Nucleotides*, 18 (11,12), (1999), 2511-2520.

Wagner, M. C., et al., "Sickle Cell Adhesion Depends on Hemodynamics and Endothelial Activation", *J. Lab. Clin. Med.*, 144, (2004), 260-267.

Walker, B. A., et al., "Adenosine $A_{2a}$ Receptor Activation Delays Apoptosis in Human Neutrophils", *The American Association of Immunologists*, (1997), pp. 2926-2931.

Wan, A. A., et al., "Binding of the Adenosine A2 Receptor Ligand (3H)CGS 21680 to Human and Rat Brain: Evidence for Multiple Affinity Sites", *Journal of Neurochemistry*, (1990), 1763-1771.

Weiner, D. L., et al., "Preliminary Assessment of Inhaled Nitric Oxide for Acute Vaso-occlusive Crisis in Pediatric Patients With Sickle Cell Disease", *JAMA*, 289(9), (2003), 1136-1142.

Wood, K. C., et al., "Endothelial Cell P-selectin Mediates a Proinflammatory and Prothrobogenic Phenotype in Cerebral Venules of Sickle Cell Transgenic Mice", *Am. J. Physiol. Heart Circ. Physiol.*, 286, (2004), H1608-H1614.

Wun, T., et al., "Platelet-Erythrocyte Adhesion in Sickle Cell Disease", *Journal of Investigative Medicine*, 47(3), (1999), 121-126.

Yale, S. H., et al., "Approach to the Vaso-occulsive Crisis in Adults With Sickle Cell Disease", *American Family Physician*, 61(5), (2000), 1349-1356.

Yoneyama, F., "Vasodepressor Mechanisms of 2-(1-octynyl)-Adenosine (YT-146), a Selective Adenosine A2 Receptor Agonist, Involve the Opening of Glibenclamide-sensitive $K^+$ Channels", *European Journal of Pharmacology*, 213 (1), (1992), pp. 199-204.

Zablocki J., et al., "Novel Short Acting Coronary Vasodilators That are Functionally Selective for the $A_{2A}$ Receptor Based on 2-Heterocyclic Substituted Adenosine Derivatives", *Drug Development Research*, 50 (1), Abstracts From Purines 2000: Biochemical, Pharmacological and Clinical Perspectives: Abstract No. 059, (May 2000), p. 63.

Zipursky, A., et al., "Oxygen Therapy in Sickle Cell Disease", *The American Journal of Pediatric Hematology/Oncology*, 14(3), (1992), 222-228.

"U.S. Appl. No. 10/412,726, Final Office Action mailed Jul. 23, 2008", 15 pgs.

"U.S. Appl. No. 10/412,726, Response filed Jan. 22, 2009 to Final Office Action mailed Jul. 23, 2008", 23 pgs.

"U.S. Appl. No. 10/412,726, Response filed Apr. 10, 2008 to Non-Final Office Action mailed Feb. 22, 2008", 30 pgs.

"U.S. Appl. No. 10/412,726, Non-Final Office Action mailed Feb. 22, 2008", 10 pgs.

"U.S. Appl. No. 10/412,726, Notice of Allowance mailed Mar. 12, 2009", 4 pgs.

"U.S. Appl. No. 11/121,169, Notice of Allowance mailed Feb. 29, 2008", 6pgs.

"U.S. Appl. No. 11/196,529, Notice of Allowance mailed Feb. 24, 2009", 8 pgs.

"U.S. Appl. No. 11/196,529, Response filed Aug. 7, 2008 to Non Final Office Action mailed Jun. 23, 2008", 21 pgs.

"U.S. Appl. No. 11/196,529, Response filed Dec. 19, 2008 to Final Office Action mailed Dec. 2, 2008", 19 pgs.

"U.S. Appl. No. 11/196,529, Final Office Action mailed Dec. 2, 2008.", 13 pgs.

"U.S. Appl. No. 11/196,529, Non-Final Office Action mailed Jun. 23, 2008", 33 pgs.

"U.S. Appl. No. 11/196,798, Notice of Allowance mailed Feb. 24, 2009", 5 pgs.

"U.S. Appl. No. 11/196,798, Non-Final Office Action mailed Mar. 31, 2008", 30 pgs.

"U.S. Appl. No. 11/196,798, Non-Final Office Action mailed Sep. 17, 2008", 6 pgs.

"U.S. Appl. No. 11/196,798, Response filed May 21, 2008 to Non Final Office Action mailed Apr. 21, 2008", 18 pgs.

"U.S. Appl. No. 11/196,798, Response filed Dec. 17, 2008 to Non-Final Office Action mailed Sep. 17, 2008", 17 pgs.

"U.S. Appl. No. 11/196,802, Notice of Allowance mailed Mar. 28, 2008", 33 pgs.

"U.S. Appl. No. 11/672,868, Non-Final Office Action mailed Apr. 13, 2009", 37 pgs.

"U.S. Appl. No. 11/691,374, Non-Final Office Action mailed Jan. 12, 2009", 40 pgs.

"U.S. Appl. No. 11/691,374, Final Office Action mailed Jun. 17, 2009", 14 pgs.

"U.S. Appl. No. 11/691,374, Preliminary Amendment filed Jun. 12, 2007", 21 pgs.

"U.S. Appl. No. 11/691,374, Response filed Aug. 17, 2009 to Final Office Action mailed Jun. 17, 2009", 14 pgs.

"U.S. Appl. No. 11/691,374, Response filed Apr. 13, 2009 to Non Final Office Action mailed Jan. 12, 2009", 23 pgs.

Knapp, C. M., et al., "The Type IV Phosphodiester Inhibitors, Ro 20-1724 and Rolipram,Block the Initiation of Cocaine Self Administration"; *Pharmocology, Biochemistry and Behavior*,62(1), (Jan. 1999), 151-158.

Webster, M., "Merriam-Webster's Collegiate Dictionary", *Tenth Edition*, (1998), 924 and 935.

*The Merck Manual of Diagnosis and Therapy*, Beers, M.A., et al. (eds.), Merck and Company, (Jan. 1999), 924-925.

*Taber's Cyclopedic Medical Dictionary*, 19th Edition, Venes, et al. (eds.), F. A. Davis, Philadelphia, (2001), 960-961.

Adah, S. A, et al., "Synthesis of complex ethynyladenosines using organic triflic enolates in palladium-catalyzed reactions: Potential agonists for the adenosine $A_2$ receptor", *Tetrahedron*, 53(20), (May 19, 1997), 6747-6754.

Barold, S. S., et al., "Significance of Transient Electrocardiographic Q Waves in Coronary Artery Diseasse", *Cardiology Clinics*, 5(3), (Aug. 1987), 367-380.

Brito, G. A. C., et al., "*Clostridium difficile* Toxin A Induces Intestinal Epithelial Cell Apoptosis and Damage: Role of Gln and Ala-Gln in Toxin A Effects", *Digestive Diseases and Sciences*, 50(7), (2005), 1271-1278.

Carruthers, A. M., et al., "Hypotensive Responses to the Putative Adenosine $A_3$ Receptor Agonist $N^6$-2-(4-Aminophenyl)-Ethyladenosine in the Rat", *Drug Development Research*, 30, (1993), 147-152.

Cavalcante, I. C, et al., "Effect of Novel $A_{2A}$ adenosine receptor agonist ATL 313 on *Clostridium difficile* toxin A-induced murin Ileal enteritis", *Infection and Immunity* 74(5), (May 2006), 2606-2612.

Cembrzynska-Nowak, M, et al., "Elevated Release of Tumor Necrosis Factor-alpha and Interferon-gamma by Bronchoalveolar Leukocytes From Patients With Bronchial Asthma.", *American Review of Respiratory Disease*, 147(2), (1993), 291-295.

Charache, S., et al., "Effect of Hydroxyurea on the Frequency of Painful Crisis in Sickle Cell Anemia", *The New England Journal of Medicine*, 332(20), (1995), 1317-1322.

Chou, T. C., et al., "Quantitative analysis of dose-effect relationships: the combined effects of multiple drugs or enzyme inhibitors", *Adv. Enzyme Regul.*, 22, (1984), 27-55.

Cohen, S. B, et al., "Adenosine-2 alpha analogue augments the treatment in experimental infectious arthritis", *Poster presented at the 48th Annual Meeting of the Orthopaedic Research Society*, Dallas, USA, (Feb. 10-13, 2002), Poster No. 0689, 1 pg.

Cothran, D. L., et al., "Ontogeny of Rat Myocardial $A_1$ Adenosine Receptors", *Biol Neonate*,68 (2), (1995), 111-118.

Cristalli, G., et al., "2-Alkynyl derivatives of adenosine-5'-N-ethyluronamide: selective A2 adenosine receptor agonists with potent inhibitory activity on platelet aggregation.", *J Med Chem.*, 37(11), (May 27, 1994), 1720-1726.

Cristalli, G., et al., "2-Aralkynyl and 2-heteroalkynyl derivatives of adenosine-5'-N-ethyluronamide as Selective $A_{2a}$ adenosine receptor agonists.", *J Med Chem.*, 38(9), (Apr. 28, 1995), 1462-1472.

Cronstein, B. N., "Adenosine, an Endogenous Anti-Inflammatory Agent", *Journal of Applied Physiology*, 76(1), (1994), 5-13.

Dechatelet, L R., et al., "Mechanism of the Luminol-Dependent Chemiluminescence of Human Neutrophils", *The Journal of Immunology*, 129(4), (1982), 1589-1593.

Dinarello, C. A., "Interleukin-1 and Tumor Necrosis Factor: Effector Cytokines in Autoimmune Diseases", *Seminars in Immunology*, 4, (1992), 133-145.

Doyle, M. P., et al., "Nucleoside-induced Arteriolar Constriction: a Mast Cell-dependent Response.", *American Journal of Physiology*, 266(5), (May 1994), H2042-H2050.

Fabry, M. E., et al., "High Expression of Human $\beta^S$- and $\alpha$-globins in Transgenic Mice: Erythrocyte Abnormalities, Organ Damage, and the Effect of Hypoxia", *Proc. Natl. Acad. Sci. USA*, 89, (1992), 12155-12159.

Fang, G. D, et al., "ATL 146e (ATL), a Selective A[2A] Adenosine Receptor Agonist, Combined with Ceftriaxone, Markedly Improves Survival in a Mouse Model of *E. coli* 026:B6 Sepsis", *Meeting Abstract B-1110, Presented at the 41st Interscience Conference on Antimicrobial Agents and Chemotherapy*, Chicago, USA, (Dec. 16-19, 2001).

Feoktistov, I., et al., "Adenosine $A_{2B}$ receptors", *The American Society for Pharmacological and Experimental Therapeutics*, 49(4), (1997), 381-402.

Feoktistov, I., et al., "Role of Adenosine in Asthma", *Drug Development Research*, 39, (1996), 333-336.

Ferrante, A., "Optimal Conditions for Simultaneous Purification of Mononuclear and Polymorphonuclear Leucocytes From Human Blood by the Hypaque-Ficoll Method", *Journal of Immunological Methods*, 36(2), (1980), 109-117.

Figler, R. A., et al., "Reconstitution of Bovine $A_1$ Adenosine Receptors and G Proteins in Phospholipid Vesicles: $\beta\gamma$.-Subunit Composition Influences Guanine Nucleotide Exchange and Agonist Binding", *Biochemistry*, 36(51), (1997), 6288-16299.

Figler, R. A., et al., "Reconstitution of Recombinant Bovine $A_1$ Adenosine Receptors in Sf9 Cell Membranes with Recombinant G Proteins of Defined Composition.", *Molecular Pharmcology*, 50(6), (Dec. 1996), 1587-1595.

Fozard, J. R., et al., "Adenosine $A_3$ Receptors Mediate Hypotension in the Angiotensin II-supported Circulation of the Pithed Rat", *British Journal of Pharmacology*, 109(1), (1993), 3-5.

Frangogiannis, N G, et al., "The Role of the Neutrophil in Myocardial Ischemia and Reperfusion", *Myocardial Iscehmia: Mechanisms, Reperfusion, Protection*, M. Karmazyn, Editor, Birkhauser Verlag Basel, (1996), 236-284.

Gao, Z, et al., "Purification of $A_1$ Adenosine Receptor-G-protein Complexes: Effects of Receptor Down-regulation and Phosphorylation on Coupling", *Biochemical Journal*, 338 (Pt3), (1999), 729-736.

Gao, Z., et al., "$A_{2B}$ Adenosine and $P2Y_2$ Receptors Stimulate Mitogen-activated Protein Kinase in Human Embryonic Kidney-293 Cells. Cross-talk Between Cyclic AMP and Protein Kinase c Pathways", *Journal of Biological Chemistry*, 274(9), (Feb. 26, 1999), 5972-5980.

Gilchrist, A., et al., "Antagonists of the Receptor-G Protein Interface Block $G_i$-coupled Signal Transduction", *Journal of Biological Chemistry*, 273 (24), (Jun. 12, 1998), 14912-14919.

Girardi, N, et al., "Inflammatory Aneurysm of the Ascending Aorta and Aortic Arch", *Ann. Thor. Surg.*, 65, (1997), 251-253.

Hall, J., et al., "Abnormal Hypothalamic-Pituitary-Adrenal Axis Function in Rheumatoid Arthritis", *Arthritis & Rheumatism*, 37(8), (1994), 1132-1137.

Hamaguchi, M., et al., "Mechanisms and Roles of Neutrophil Infiltration in Stress-Induced Gastric Injury in Rats", *Digestive Diseases and Sciences*, 46(12), (2001), 2708-2715.

Hamajima, E., et al., "Effects of FK506, An Immunosuppressive Agent, on Genesis of Water-Immersion Stress-Induced Gastric Lesions in Rats", *Digestive Diseases and Sciences*, 39(4), (1994), 713-720.

Hartung, H. P., "Immune-Mediated Demyelination", *Annals of Neurology*, 33 (6), (Jun. 1993), 563-567.

Hatley, M. E., et al., "Increased Production of 12/15 Lipoxygenase Eicosanoids Accelerates Monocyte/Endothelial Interactions in Diabetic db/db Mice", *The Journal of Biological Chemistry*, 278(28), (2003), 25369-25375.

Hogan, C. J., et al., "Inhibiting the inflammatory response in joint sepsis", *Arthroscopy*, 17(3), (Mar. 2001), 311-315.

Holmes, D, R., et al., "Restenosis After Percutaneous Transluminal Coronary Angioplasty (PTCA): A Report From the PTCA Registry of the National Heart, Lung, and Blood Institute", *American Journal of Cardiology*, 53, 1984, 77C-81C.

Imagawa, D. K., et al., "The Role of Tumor Necrosis Factor in Allograft Rejection", *Transplantation*, 51, (Jan. 1991), 57-62.

Ito, B. R., et al., "Role of Cardiac Mast Cells in Complement C5a-induced Myocardial Ischemia", *American Journal of Physiology—Heart and Circulatory Physiology*, 264(5), (May 1993), H1346-H1354.

Jolly, S. R., "Effects of Lodoxamide on Ischemic Reperfused Myocardium", *Journal of Cardiovascular Pharmacology*, 4(3), (1982), 441-448.

Kahky, M. P., et al., "Portal Infusion of Tumor Necrosis Factor Increases Mortality in Rats", *Journal of Surgical Research*, 49 (2), (1990), 138-145.

Keller, A. M., "Acute Reoxygeneration Injury in the Isolated Rat Heart: Role of Resident Cardiac Mast Cells", *Circulation Research*, 63(6), (Dec. 1988), 1044-1052.

Kennedy, A. P., et al., "Covalent Modification of Transmembrane Span III of the $A_1$ Adenosine Receptor With an antagonist Photoaffinity Probe.", *Molecular Pharmacology*, 50, (Oct. 1996), 789-798.

Klotz, Karl-Norbert, et al., "2-Substituted N-ethylcarboxamidoadenosine derivatives as high-affinity agonists at human $A_3$ adenosine receptors", *Naunyn-Schmiedebergs Archives of Pharmacology*, 360(2), (Aug. 1999), 103-108.

Kokura, S., et al., "T-Lymphocyte-Derived Tumor Necrosis Factor Exacerbates Anoxia-Reoxygenation-Induced Neutrophil-Endothelial Cell Adhesion", *Circulation Research*, 86, (2000), 205-213.

Kolachala, V., et al., "TNF-α Upregulates Adenosine 2b (A2b) Receptor Expression and Signalling in Intestinal Epithlial Cells: A Basis for A2bR Overexpression in Colitis", *Cell. Mol. Life Sci.*, 62, (2005), 2647-2657.

Kollias-Baker, C., et al., "Allosteric Enhancer PD 81,723 Acts by Novel Mechanism to Potentiate Cardiac Actions of Adenosine", *Circulation Research*, 75(6), (Dec. 1994), 961-971.

Krawisz, J. E., et al., "Quantitative Assay for Acute Intestinal Inflammation Based on Myeloperoxidase Activity", *Gastroenterology*, 87(6), (1984), 1344-1350.

Leclerc, G., et al., "Percutaneous Arterial Gene Transfer in a Rabbit Model", *Journal of Clinical Investigation*, 90(3), (1992), 936-944.

Legrand-Poels, S., et al., "Activation of Human Immunodeficiency Virus Type 1 by Oxidative Stress", *AIDS Research and Human Retroviruses*, 6(12), (1990), 1389-1397.

Lette, J., et al., "Safety of Dipyridamole Testing in 73,806 Patients: The Multicenter Dipyridamole Safety Study", *Journal of Nuclear Cardiology*, 2(1), (1995), 3-17.

Li, Y., et al., "Mouse Spinal Cord Compression Injury is Reduced by Either Activation of the Adenosine $A_{2A}$ Receptor on Bone Marrow-Derived Cells or Deletion of the $A_{2A}$ Receptor on Non-Bone Marrow-Derived Cells", *Neuroscience*, 141, (2006), 2029-2039.

Linden, J, "Cloned Adenosine $A_3$ Receptors: Pharmacological Properties, Species Differences and Receptor Functions.", *Trends in Pharmacological Sciences*, 15(8), (Aug. 1994), 298-306.

Linden, J, et al., "The Structure and Function of $A_1$ and $A_{2B}$ Adenosine Receptors", *Life Science*, 62 (17/18), , (1998), 1519-1524.

Linden, J., "Calculating the Dissociation Constant of an Unlabeled Compound from the Concentration Required to Displace Radiolabel Binding by 50%", *Journal of Cyclic Nucleotide Research*, 8(3), (1982), 163-172.

Linden, J., "Chapter 2—Recombinant Techniques as Applied to the Study of A1 Adenosine Receptors", *In: Adenosine and Adenine Nucleotides: From Molecular Biology to Integrative Physiology*, Belardinelli, L., Editor, Kluwer Academic Publishers, Boston, (1995), 15-19.

Linden, J., et al., "Molecular Cloning and Functional Expression of a Sheep $A_3$ Adenosine Receptor with Widespread Tissue Distribution", *Molecular Pharmacology*, 44(3), (1993), 524-532.

Londos, C., et al., "Subclasses of external adenosine receptors", *Proc. Natl. Acad. Sci. USA*, 77(5), (1980), 2551-2554.

Mahan, L. C., et al., "Cloning and Expression of an $A_1$ Adenosine Receptor from Rat Brain", *Molecular Pharmacology*, 40(1), (Jul. 1991), 1-7.

Männel, D. N., et al., "Tumor Necrosis Factor: A Cytokine Involved in Toxic Effects of Endotoxin", *Reviews of Infectious Diseases*, 9(Suppl. 5), (1987), S602-S606.

March, J., "", *In: Advanced Organic Chemistry: Reactions, Mechanisms, and Structure*, Fourth Edition, John Wiley & Sons, (1992), p. 400.

Marquardt, D. L., et al., "Potentiation of Mast Cell Mediator Release by Adenosine", *The Journal of Immunology*, 120(3), (Mar. 1978), 871-878.

Martin, P. L., et al., "Characterization of 8-(N-Methylisopropyl)Amino-$N^6$-(5'-Endohydroxy-endonorbornyl)-9-methyladenine (WRC-0571), a Highly Potent and Selective, Non-xanthine Antagonist of A1 Adenosine Receptors.", *The Journal of Pharmacology and Experimental Therapeutics*, 276(2), (Feb. 1996), 490-499.

Matherne, G. P., et al., "Transgenic $A_1$ Adenosine Receptor Overexpression Increases Myocardial Resistance to Ischemia", *Proc. Natl. Acad. Sci. USA*, 94, (Jun. 1997), 6541-6546.

Matsuyama, T., "Cytokines and HIV Infection: is AIDS a Tumor Necrosis Factor Disease?", *AIDS*, 5(12), (1991), 1405-1417.

McGarrity, S. T., "Inhibition of Neutrophil Superoxide Anion Generation by Platelet Products: Role of Adenine Nucleotides", *Journal of Leukocyte Biology*, 44(5), (1988), 411-421.

McLaughlin, D. P., et al., "Hemodynamic and Metabolic Correlates of Dipyridamole-induced Myocardial Thallium-201 Perfusion Abnormalities in Multivessel Coronary Artery Disease.", *American Journal of Cardiology*, 73(16), (Jun. 1994), 1159-1164.

Miyamoto, F, et al., "Retinal Cytokine Response in Mouse Alkali-Burned Eye", *Opthalmic Research*, 30, (1997), 168-171.

Mizumura, T., et al., "PD 81,723, an Allosteric Enhancer of the $A_1$ Adenosine Receptor, Lowers the Threshold for Ischemic Preconditioning in Dogs.", *Circulation Research*, 79(3), (Sep. 1996), 415-423.

Molnar-Kimber, K. L., et al., "Modulation of TNFα and IL-1β From Endotoxin-Stimulated Monocytes by Selective PDE Isozyme Inhibitors", *Agents & Actions*, 39, (1993), C77-C79.

Mumby, S. M., et al., "G-protein α-subunit expression, myristoylation, and membrane association in COS cells", *Proc. Natl. Acad. Sci. USA*. 87(2), (Jan. 1990), 728-732.

Nabel, E. G., "Site-Specific Gene Expression in Vivo by Direct Gene Transfer into the Arterial Wall", *Science*, 249, (1990), 1285-1288.

Newman, K. D., "Adenovirus-mediated Gene Transfer into Normal Rabbit Arteries Results in Prolonged Vascular Cell Activation, Inflammation and Neointimal Hyperplasia", *Journal of Clinical Investigation*, 96(6), (1995), 2955-2965.

Odashima, M., et al., "Attenuation of Gastric Mucosal Inflammation Induced by Aspirin Through the Activation of $A_{2a}$ Adenosine Receptor in Rats", *World Journal of Gastroenterology*, 12(4), (2006), 6 pgs.

Odashima, M., et al., "Selective Adenosine $A_{2A}$ Receptor Agonist, ATL-146e, Attenuates Stress-Induced Gastric Lesions in Rats", *Journal of Gastroenterology and Hepatology*, 20(2), (2005), 275-280.

Osuka, M. D, et al., "Enhanced protection from renal ischemia-reperfusion [correction of ischemia:reperfusion] injury with $A_{2A}$-adenosine receptor activation and PDE 4 inhibition", *Kidney Int.*, 59(6), (Jun. 2001), 2114-2125.

Pennell, R L, et al., "Inflammatory abdominal aortic aneurysms: A thirty-year review", *Journal of Vascular Surgery*, 2, (1985), 859-869.

Pfister, J. R., et al., "Synthesis and Biological Evaluation of the Enantiomers of the Potent and Selective $A_1$-adenosine Antagonist 1,3-dipropyl-8-[2-(5,6-epoxynorbonyl)]-xanthine", *Journal of Medicinal Chemistry*, 40 (12), (1997), 1773-1778.

Raitt, M. H., et al., "Abnormal Q Waves are Common Early in AMI and Do Not Predict Decreased Myocardial Salvage With Thrombolytic Therapy", *Special Issue Journal of American College of Cardiology*, Abstract No. 895-77, (Feb. 1994), p. 195A.

Ranhosky, A., et al., "The Safety of Intravenous Dipyridamole Thallium Myocardial Perfusion Imaging", *Circulation*, 81(4), (Apr. 1990), 1205-1209.

Rieger, G. M, et al., "Design, Synthesis and Evaluation of Novel $A_{2A}$ Adenosine Receptor Agonist", *Journal of Medicinal Chemistry*, 44(4), (Feb. 15, 2001), 531-539.

Ross, R., "The Pathogenesis of Atherosclerosis: A Perspective for the 1990s", *Nature*, 362, (Apr. 29, 1993), 801-809.

Ross, S. D, "Selective Adenosine-$A_{2A}$ Activation Reduces Lung Reperfusion Injury Following Transplantation", *Journal of Heart and lung transplantation*, 18 (1), (Oct. 1999), 994-1002.

Rothe, G. A., et al., "Flow Cytometric Measurement of the Respiratory Burst Activity of Phagocytes Using Dihydrorhodamine 123", *Journal of Immunological Methods*, 138(1), (1991), 133-135.

Santucci, L., et al., "Pentoxifylline Prevents Indomethacin Induced Acute Gastric Mucosal Damage in Rats: Role of Tumour Necrosis Factor Alpha", *Gut*, 35, (1994), 909-915.

Sawmiller, D. R., et al., "Effects and Xanthine Amine Congener on Hypoxic Resistence and Venous and Epicardial Adenosine Concentrations.", *Cardiovascular Research*, 28(5), (May 1994), 604-609.

Seekamp, A., "Ischemia—Reperfusion Injury", *Agents and Actions Supplements*, 41, (1993), 137-152.

Sharief, M. K., et al., "Elevated Serum Levels of Tumor Necrosis Factor-$\alpha$ in Guillain-Barre Syndrome", *Annals of Neurology*, 33, (Jun. 1993), 591-596.

Sharma, H S, et al., "Role of cytokines in myocardial ischemia and reperfusion", *Med. of Inflamm.*, 6, (1987), 175-183.

Shay, H., et al., "A Simple Method for the Uniform Production of Gastric Ulceration in the Rat", *Gastroenterology*, 5(1), (1945), 43-61.

Shi, W., et al., "Endothelial Responses to Oxidized Lipoproteins Determine Genetic Susceptibility to Atherosclerosis in Mice", *Circulation*, 102, (2000), 75-81.

Siragy, H. M., et al., "Sodium Intake Markedly Alters Renal Interstitial Fluid Adenosine", *Hypertension*, 27 (3 Pt 1), (Mar. 1996), pp. 404-407.

Sullivan, G W., et al., "Interactions of Human Neutrophils with Leukotoxic Streptococci",*Infection and Immunity*, 30 (1), (1980), pp. 272-280.

Sullivan, G. W., et al., "Adenosine and Related Compounds Counteract Tumor Necrosis Factor-$\alpha$ Inhibition of Neutrophil Migration: Implication of a Novel Cyclic AMP-Independent Action on the Cell Surface", *The Journal of Immunology*, 145(5), (1990), 1537-1544.

Sullivan, G. W, et al., "Neutrophil $A_{2A}$ adenosine receptor inhibits inflammation in a rat model of meningitis: synergy with the type IV phosphodiesterase inhibitor, rolipram.", *The Journal of Infectious Diseases*, 180(5), (Nov. 1999), 1550-1560.

Sullivan, G. W., "Two Methylxanthines, Pentoxifylline (PTX) and Caffeine (CAF) Have Divergent Effects on Tumor Necrosis Factor (TNF)-Primed Human Neutrophil (PMN) Activation", *Clinical Research*, 41(2), (1993), p. 172A.

Takeuchi, K., et al., "Oxygen Free Radicals and Lipid Peroxidation in the Pathogenesis of Gastric Mucosal Lesions Induced by Indomethacin in Rats"*Digestion*, 49(3), (1991), 175-184.

Terrosu, P., et al., "Angiographic Correlate of Post-Reperfusion Abnormal Q Waves", *Japanese Heart Journal*, 29(2), (Mar. 1988), 179-187.

Tomer, A., "Platelet Activation as a Marker for in vivo Prothrombotic Activity: Detection by Flow Cytometry", *Journal of Biological Regulators and Homeostatic Agents*, 18, (2004), 172-177.

Topol, E. J., et al., "Randomised Trial of Coronary Intervention With Antibody Against Platelet IIb/IIIa integrin for Reduction of Clinical Restenosis: Results at Six Months", *The Lancet*, 343(8902), (1994), 881-886.

Tracey, K. J., "Cachectin/Tumor Necrosis Factor Induces Cachexia, Anemia, and Inflammation", *Journal of Experimental Medicine*, 167, (Mar. 1988), 1211-1227.

Tucker, A. L., et al., "A1 adenosine receptors. Two amino acids are responsible for species differences in ligand recognition", *Journal of Biological Chemistry*, 269(45), (Nov. 11, 1994), 27900-27906.

Ukena, D., et al., "Species Differences in Structure-Activity Relationships of Adenosine Agonists and Xanthine Antagonists at Brain A1 Adenosine Receptors", *FEBS Letters*, 209(1), , (Dec. 1986), 122-128.

Venes, et al., "Taber's Cyclopedic Dictionary", *Taber's Cyclopedic Medical Dictionary*, 19, 960-961.

Vu, C. B., et al., "Piperazine Derivatives of [1,2,4] Triazolo [1,5-a][1,3,5]triazine as Potent and Selective Adenosine A (sub 2a) Receptor Antagonists", *J. Med. Chem.*, 47, (2004), 4291-4299.

Walker, D I, et al., "Inflammatory Aneurysms of the Abdominal Aorta", *Brit. J. Surg.*, 59, (1972), 609-614.

Wallace, J. L., et al., "Gastric Ulceration Induced by Nonsteroidal Anti-Inflammatory Drugs is a Neutrophil-Dependent Process", *American Journal of Physiology Gastrointestinal and Liver Physiology*, 259, (1990), G462-G467.

Wolff, A. A., et al., "Ventricular Arrhythmias Parallel Cardiac Histamine Efflux After Coronary Artery Occlusion in the Dog", *Agents and Actions*, 25 (3/4), (1988), 296-306.

Yoshida, N., et al., "Role of Neutrophil-Mediated Inflammation in Aspirin-Induced Gastric Mucosal Injury", *Digestive Diseases and Sciences*, 40(11), (1995), 2300-2304.

Yoshikawa, T., et al., "Augmentative Effects of Tumor Necrosis Factor-Alpha (Human, Natural Type) on Polymorphonuclear Leukocyte-Derived Superoxide Generation Induced by Various Stimulants", *International Journal of Immunopharmacology*, 14(8), (1992), 1391-1398.

Yoshikawa, T., et al., "Role of Active Oxygen, Lipid Peroxidation, and Antioxidants in the Pathogenesis of Gastric Mucosal Injury Induced by Indomethacin in Rats", *Gut*,34(6), (1992), 732-737.

Zhang, X., et al., "Cellular Accumulation and Retention of the Technetium-99m-Labelled Hypoxia Markers BRU59-21 and Butylene Amine Oxime", *Nuclear Medicine and Biology*, 28, (2001), 949-957.

"U.S. Appl. No. 08/272,821, Non Final Office Action mailed Mar. 9, 1998", 6 pgs.

"U.S. Appl. No. 08/272,821, Notice of Allowance mailed Aug. 5, 1998", 4 pgs.

"U.S. Appl. No. 08/272,821, Preliminary Amendment filed Jun. 20, 1997", 5 pgs.

"U.S. Appl. No. 08/272,821, Response filed Jun. 9, 2008 to Non Final Office Action mailed Mar. 9, 2008", 8 pgs.

"U.S. Appl. No. 08/272,821, Response filed Nov. 3, 1997 to Restriction Requirement mailed Oct. 2, 1997", 5 pgs.

"U.S. Appl. No. 08/272,821, Restriction Requirement mailed Oct. 2, 1997", 5 pgs.

"U.S. Appl. No. 09/003,930, Final Office Action mailed Aug. 6, 1999", 6 pgs.

"U.S. Appl. No. 09/003,930, Non-Final Office Action mailed Nov. 4, 1998", 7 pgs.

"U.S. Appl. No. 09/003,930, Preliminary Amendment filed Feb. 8, 1999", 5 pgs.

"U.S. Appl. No. 09/003,930, Response filed May 4, 1999 to Non-Final Office Action mailed Nov. 4, 1998", 12 pgs.

"U.S. Appl. No. 09/003,930, Response filed Nov. 4, 1999 to Final Office Action mailed Aug. 6, 1999", 10 pgs.

"U.S. Appl. No. 09/320,769, Non Final office action mailed Jul. 18, 2000", 5 pgs.

"U.S. Appl. No. 09/333,387, Non-Final Office Action mailed Jul. 13, 2000", 5 pgs.

"U.S. Appl. No. 09/333,387, Notice of Allowance mailed Aug. 25, 2000", 2 pgs.

"U.S. Appl. No. 09/333,387, Response filed Aug. 28, 2000 to Non-Final Office Action mailed Jul. 13, 2000", 2 pgs.

"U.S. Appl. No. 09/333,387, Supplemental Amendment filed Aug. 28, 2000", 2 pgs.

"U.S. Appl. No. 09/333,387, Supplemental Notice of Allowability mailed Mar. 7, 2001", 4 pgs.

"U.S. Appl. No. 09/336,198, Non Final Office Action mailed Mar. 8, 2001", 7 pgs.

"U.S. Appl. No. 09/336,198, Notice of allowance mailed Jun. 25, 2001", 4 pgs.

"U.S. Appl. No. 09/336,198, Response filed Jun. 8, 2001 to Non Final office action mailed Mar. 8, 2001", 4 pgs.

"U.S. Appl. No. 09/543,385, Notice of Allowance filed Mar. 25, 2002", 5 pgs.
"U.S. Appl. No. 09/543,385, Notice of Allowance mailed Sep. 24, 2001", 5 pgs.
"U.S. Appl. No. 09/543,385, Preliminary Amendment filed Apr. 4, 2000", 2 pgs.
"U.S. Appl. No. 09/543,385, Response filed Jun. 29, 2001 to Restriction Requirement mailed May 29, 2001", 2 pgs.
"U.S. Appl. No. 09/543,385, Restriction Requirement mailed May 29, 2001", 3 pgs.
"U.S. Appl. No. 09/543,385, Supplemental Preliminary Amendment filed Aug. 31, 2000", 6 pgs.
"U.S. Appl. No. 09/634,407, Non Final office action mailed Sep. 25, 2001", 21 pgs.
"U.S. Appl. No. 09/634,407, Notice of allowance mailed Sep. 4, 2002", 10 pgs.
"U.S. Appl. No. 09/634,407, Response filed Feb. 26, 2002 to Non Final office action mailed Sep. 25, 2001", 8 pgs.
"U.S. Appl. No. 09/827,083, 312 Amendment filed Dec. 10, 2002", 2 pgs.
"U.S. Appl. No. 09/827,083, Notice of Allowance mailed Sep. 10, 2002", 6 pgs.
"U.S. Appl. No. 09/827,083, Preliminary Amendment mailed Apr. 5, 2001", 5 pgs.
"U.S. Appl. No. 10/041,776, Non final office action mailed Dec. 31, 2002", 14 pgs.
"U.S. Appl. No. 10/041,776, Notice of allowance mailed Jul. 15, 2003", 14 pgs.
"U.S. Appl. No. 10/041,776, Response filed Apr. 30, 2003 to Non final office action mailed Dec. 31, 2002", 11 pgs.
"U.S. Appl. No. 10/263,379, Advisory Action mailed Mar. 1, 2006", 7 pgs.
"U.S. Appl. No. 10/263,379, Advisory Action mailed Apr. 11, 2006", 5 pgs.
"U.S. Appl. No. 10/263,379, Final Office Action mailed Nov. 1, 2006", 6 pgs.
"U.S. Appl. No. 10/263,379, Final Office Action mailed Nov. 9, 2005", 15 pgs.
"U.S. Appl. No. 10/263,379, Final Office Action mailed Nov. 23, 2004", 43 pgs.
"U.S. Appl. No. 10/263,379, Non-Final Office Action mailed Apr. 25, 2005", 13 pgs.
"U.S. Appl. No. 10/263,379, Non-Final Office Action mailed Jun. 14, 2006", 7 pgs.
"U.S. Appl. No. 10/263,379, Non-Final Office Action mailed Jun. 17, 2004", 35 pgs.
"U.S. Appl. No. 10/263,379, Notice of Allowance mailed Dec. 12, 2006", 4 pgs.
"U.S. Appl. No. 10/263,379, Response filed Feb. 8, 2006 to Final Office Action mailed Nov. 9, 2005", 19 pgs.
"U.S. Appl. No. 10/263,379, Response filed Feb. 23, 2005 to Final Office Action mailed Nov. 23, 2004", 20 pgs.
"U.S. Appl. No. 10/263,379, Response filed Apr. 4, 2006 to Final Office Action mailed Nov. 9, 2005 and Advisory Action mailed Mar. 1, 2006", 19 pgs.
"U.S. Appl. No. 10/263,379, Response filed Apr. 23, 2004 to Restriction Requirement mailed Mar. 24, 2004", 2 pgs.
"U.S. Appl. No. 10/263,379, Response filed May 2, 2006 to Final Office Action mailed Nov. 9, 2005 and Advisory Action mailed Apr. 11, 2006", 15 pgs.
"U.S. Appl. No. 10/263,379, Response filed Sep. 11, 2006 to Non Final Office Action mailed Jun. 14, 2006", 13 pgs.
"U.S. Appl. No. 10/263,379, Response filed Sep. 26, 2005 to Non Final Office Action mailed Apr. 25, 2005", 19 pgs.
"U.S. Appl. No. 10/263,379, Response filed Oct. 18, 2004 to Non Final Office Action mailed Jun. 17, 2004", 25 pgs.
"U.S. Appl. No. 10/263,379, Response filed Nov. 21, 2006 to Final Office Action mailed Nov. 1, 2006", 13 pgs.
"U.S. Appl. No. 10/263,379, Restriction Requirement mailed Mar. 24, 2004", 4 pgs.
"U.S. Appl. No. 10/379,154, 312 Amendment filed Apr. 4, 2007", 3 pgs.
"U.S. Appl. No. 10/379,154, Final Office Action mailed Feb. 17, 2004", 4 pgs.
"U.S. Appl. No. 10/379,154, Final Office Action mailed Mar. 30, 2006", 5 pgs.
"U.S. Appl. No. 10/379,154, Non-Final Office Action mailed Jun. 17, 2004", 4 pgs.
"U.S. Appl. No. 10/379,154, Non-Final Office Action mailed Aug. 1, 2005", 5 pgs.
"U.S. Appl. No. 10/379,154, Non-Final Office Action mailed Aug. 8, 2003", 4 pgs.
"U.S. Appl. No. 10/379,154, Non-Final Office Action mailed Dec. 15, 2004", 5 pgs.
"U.S. Appl. No. 10/379,154, Notice of Allowance mailed Jan. 4, 2007", 5 pgs.
"U.S. Appl. No. 10/379,154, Response filed May 16, 2005 to Non-Final Office Action mailed Dec. 15, 2004", 7 pgs.
"U.S. Appl. No. 10/379,154, Response filed May 17, 2004 to Final Office Action mailed Feb. 17, 2004", 6 pgs.
"U.S. Appl. No. 10/379,154, Response filed May 31, 2006 to Final Office Action mailed Mar. 30, 2006", 7 pgs.
"U.S. Appl. No. 10/379,154, Response filed Sep. 17, 2004 to Non-Final Office Action Jun. 17, 2004", 6 pgs.
"U.S. Appl. No. 10/379,154, Response filed Nov. 6, 2003 to Non-Final Office Action mailed Aug. 8, 2003", 8 pgs.
"U.S. Appl. No. 10/379,154, Response filed Dec. 1, 2005 to Non-Final Office Action mailed Aug. 1, 2005", 7 pgs.
"U.S. Appl. No. 10/412,726, Examiner Interview Summary mailed Mar. 21, 2007", 3 pgs.
"U.S. Appl. No. 10/412,726, Examiner Interview Summary mailed Apr. 23, 2007", 4 pgs.
"U.S. Appl. No. 10/412,726, Examiner Interview Summary mailed Apr. 26, 2007", 4 pgs.
"U.S. Appl. No. 10/412,726, Examiner Interview Summary mailed Jul. 11, 2006", 5 pgs.
"U.S. Appl. No. 10/412,726, Final Office Action mailed Jul. 19, 2007", 10 pgs.
"U.S. Appl. No. 10/412,726, Final Office Action mailed Oct. 8, 2004", 7 pgs.
"U.S. Appl. No. 10/412,726, Final Office Action mailed Dec. 5, 2005", 13 pgs.
"U.S. Appl. No. 10/412,726, Non Final Office Action mailed Mar. 16, 2005", 15 pgs.
"U.S. Appl. No. 10/412,726, Non Final Office Action mailed Apr. 7, 2004", 8 pgs.
"U.S. Appl. No. 10/412,726, Non Final Office Action mailed Oct. 30, 2006", 12 pgs.
"U.S. Appl. No. 10/412,726, Non-Final Office Action mailed Apr. 16, 2010", 5 pgs.
"U.S. Appl. No. 10/412,726, Response filed Feb. 8, 2005 to Final Office Action mailed Oct. 8, 2004", 22 pgs.
"U.S. Appl. No. 10/412,726, Response filed Apr. 27, 2007 to Non Final Office Action mailed Oct. 30, 2006", 23 pgs.
"U.S. Appl. No. 10/412,726, Response filed May 5, 2006 to Final office action mailed Dec. 5, 2005", 23 pgs.
"U.S. Appl. No. 10/412,726, Response filed Jul. 9, 2004 to Non Final Office Action mailed Jul. 9, 2004", 20 pgs.
"U.S. Appl. No. 10/412,726, Response filed Sep. 16, 2005 to Non Final Office Action mailed Mar. 16, 2005", 25 pgs.
"U.S. Appl. No. 10/412,726, Response filed Oct. 31, 2007 to Final Office Action mailed Jul. 19, 2007", 28 pgs.
"U.S. Appl. No. 11/002,008, Final office action mailed Apr. 2, 2007", 25 pgs.
"U.S. Appl. No. 11/002,008, Non Final office action mailed Jul. 13, 2006", 11 pgs.
"U.S. Appl. No. 11/002,008, Response filed Dec. 18, 2008 to Non Final office action mailed Jul. 13, 2006", 31 pgs.
"U.S. Appl. No. 11/002,008, Notice of Allowance mailed Dec. 12, 2007", 8 pgs.
"U.S. Appl. No. 11/002,008, Response filed Sep. 17, 2007 to Final Office Action mailed Apr. 2, 2007.", 26 pgs.
"U.S. Appl. No. 11/121,169, Non-Final Office Action Mailed Aug. 21, 2007", 8 pgs.

"U.S. Appl. No. 11/121,169, Response to Non-Final Office Action filed Dec. 20, 2007", 16 pgs.
"U.S. Appl. No. 11/196,529, Preliminary Amendment filed Nov. 7, 2005", 20 pgs.
"U.S. Appl. No. 11/196,798, Response filed Feb. 8, 2008 to Restriction Requirement mailed Jan. 9, 2008", 18 pgs.
"U.S. Appl. No. 11/196,798, Restriction Requirement mailed Jan. 9, 2008", 6 pgs.
"U.S. Appl. No. 11/196,802, Preliminary Amendment filed Nov. 10, 2005", 16 pgs.
"U.S. Appl. No. 11/196,802, Response filed Feb. 8, 2008 to Restriction Requirement mailed Jan. 9, 2008", 16 pgs.
"U.S. Appl. No. 11/196,802, Restriction Requirement mailed Jan. 9, 2008", 6 pgs.
"U.S. Appl. No. 11/222,664, Non final office action mailed Mar. 16, 2007", 10 pgs.
"U.S. Appl. No. 11/222,664, Non final office action mailed Jul. 14, 2006", 28 pgs.
"U.S. Appl. No. 11/222,664, Preliminary Amendment mailed Jun. 17, 2006", 4 pgs.
"U.S. Appl. No. 11/222,664, Response filed Sep. 17, 2007 to Non-Final Office Action mailed Mar. 16, 2007.", 25 pgs.
"U.S. Appl. No. 11/222,664, Response filed Dec. 14, 2006 to Non final office action mailed Jul. 14, 2006", 28 pgs.
"U.S. Appl. No. 11/222,664, Notice of Allowance Mailed Dec. 12, 2007", 11 pgs.
"U.S. Appl. No. 11/497,280, Non-Final Office Action mailed Jun. 3, 2009 ", 14 pgs.
"U.S. Appl. No. 11/672,868, Examiner Interview Summary mailed Nov. 5, 2009", 2 pgs.
"U.S. Appl. No. 11/672,868, Preliminary Amendment mailed Feb. 12, 2008", 15 pgs.
"U.S. Appl. No. 11/691,374, Non Final Office Action mailed Sep. 29, 2009", 6 pgs.
"U.S. Appl. No. 11/691,374, Notice of Allowance mailed Feb. 1, 2010", 7 pgs.
"U.S. Appl. No. 11/691,374, Preliminary Amendment filed Mar. 26, 2007", 3 pgs.
"U.S. Appl. No. 11/691,374", 73 pgs.
"U.S. Appl. No. 11/691,374, Response filed Dec. 3, 2009 to Non Final Office Action mailed Sep. 29, 2009", 16 pgs.
"U.S. Appl. No. 11/739,680, Non-Final Office Action mailed Mar. 31, 2009", 20 pgs.
"U.S. Appl. No. 11/739,680, Preliminary Amendment filed Apr. 24, 2007", 3 pgs.
"U.S. Appl. No. 11/739,680, Supplemental Preliminary Amendment filed Jul. 18, 2007", 6 pgs.
"U.S. Appl. No. 11/765,320, Non-Final Office Action mailed Aug. 20, 2010", 24 pgs.
"U.S. Appl. No. 11/765,320, Response filed Jun. 2, 2010 to Restriction Requirement mailed Apr. 2, 2010", 20 pgs.
"U.S. Appl. No. 11/765,320, Restriction Requirement mailed Apr. 2, 2010", 5 pgs.
"U.S. Appl. No. 12/338,599, Preliminary Amendment filed Feb. 20, 2009", 7 pgs.
"U.S. Appl. No. 12/487,235 Final Office Action mailed Sep. 20, 2010", 15 pgs.
"U.S. Appl. No. 12/487,235, Non-Final Office Action mailed Dec. 28, 2009", 7 pgs.
"U.S. Appl. No. 12/487,235, Response filed Jun. 28, 2010 to Non Final Office Action mailed Dec. 28, 2009", 12 pgs.
"U.S. Appl. No. 12/487,265, Non-Final Office Action mailed Dec. 18, 2009", 5 pgs.
"U.S. Appl. No. 12/487,265, Notice of Allowance mailed Apr. 6, 2010", 4 pgs.
"U.S. Appl. No. 12/487,265, Notice of Allowance mailed Sep. 7, 2010", 6 pgs.
"U.S. Appl. No. 12/487,265, Response filed Jan. 21, 2010 to Non Final Office Action mailed Dec. 18, 2009", 7 pgs.
"U.S. Appl. No. 12/630,231, Non Final Office Action mailed Jun. 28, 2010", 14 pgs.
"Australian Application Serial No. 2002362443, Response filed May 1, 2008 to Examiner's First Report mailed May 29, 2007", 46 pgs.
"Australian Application Serial No. 2005201255, Examiner's First Report mailed Apr. 13, 2007", 2 pgs.
"Australian Application Serial No. 2005201255, Response filed Feb. 7, 2008 to Examiner's Report dated Oct. 31, 2007", 6 pgs.
"Australian Application Serial No. 2005201255, Response filed Oct. 2, 2007 to Examiner's Report mailed Apr. 13, 2007", 8 pgs.
"Australian Application Serial No. 21082/99, Examiner's First Report dated Jun. 29, 2001", 3 pgs.
"Australian Application Serial No. 27454/00, Examiner's Report mailed Feb. 20, 2003", 1 pgs.
"Australian Application Serial No. 27454/00, Response filed Oct. 19, 2004 to Examiner's Report mailed Feb. 20, 2003", 14 pgs.
"Canadian Application Serial No. 2,361,614, Notice of Allowance mailed Mar. 26, 2008", 1 pg.
"Canadian Application Serial No. 2,361,614, Office Action mailed Jul. 20, 2007", 2 pgs.
"Canadian Application Serial No. 2,361,614, Response filed Nov. 7, 2007 to Office Action mailed Jul. 20, 2007", 9 pgs.
"Canadian Application Serial No. 2,375,374, Office Action Mailed Jan. 14, 2009", 11 pgs.
"Canadian Application Serial No. 2,375,374, Response filed Mar. 16, 2009 to Office Action Mailed Jan. 14, 2009", 7 pgs.
"Canadian Application Serial No. 2,460,911, Office Action mailed Apr. 16, 2010", 2 pgs.
"Canadian Application Serial No. 2,460,911, Office Action mailed Jun. 12, 2009", 7 pgs.
"Canadian Application Serial No. 2,460,911, Response filed Dec. 14, 2009 to Non Final Office Action mailed Jun. 12, 2009", 35 pgs.
"Canadian Application Serial No. 2375374, Notice of Allowance mailed Jul. 23, 2009", 1 pg.
"European Application Serial No. 00905833.0, Communication mailed Nov. 13, 2002", 3 pgs.
"European Application Serial No. 00905833.0, Response filed May 14, 2003 to Communication mailed Nov. 13, 2002", 12 pgs.
"European Application Serial No. 00941335.2-2110, Communication mailed Aug. 26, 2002", 4 pgs.
"European Application Serial No. 00941335.2-2110, Response filed Dec. 20, 2002 to Communication mailed Aug. 26, 2002", 10 pgs.
"European Application Serial No. 02800432.3, Communication mailed Jan. 13, 2005", 3 pgs.
"European Application Serial No. 02800432.3, Communication mailed Aug. 30, 2005", 2 pgs.
"European Application Serial No. 02800432.3, Communication mailed Sep. 20, 2004", 6 pgs.
"European Application Serial No. 02800432.3, Communication mailed Oct. 16, 2006", 5 pgs.
"European Application Serial No. 02800432.3, Office Action mailed Apr. 22, 2010", 3 Pgs.
"European Application Serial No. 02800432.3, Office Action Response Filed Jun. 23, 2010", 2 pgs.
"European Application Serial No. 02800432.3, Response filed Feb. 21, 2007 to Communication mailed Oct. 16, 2006", 19 pgs.
"European Application Serial No. 02800432.3, Response filed Nov. 1, 2005 to Communication mailed Aug. 30, 2005", 19 pgs.
"European Application Serial No. 03728372.8, Office Action mailed Apr. 11, 2005", 4 pgs.
"European Application Serial No. 03728372.8, Office Action mailed Nov. 24, 2005", 3 pgs.
"European Application Serial No. 03728372.8, Response filed Feb. 22, 2006 to Office Action mailed Nov. 24, 2005", 10 pgs.
"European Application Serial No. 03728372.8, Response filed Oct. 21, 2005 to Office Action mailed Apr. 11, 2005", 14 pgs.
"European Application Serial No. 05756108.6, Office Action mailed Aug. 6, 2010", 9 pgs.
"European Application Serial No. 05803845.6, Communication mailed Jul. 26, 2007", 3 pgs.
"European Application Serial No. 05803845.6, Response filed Dec. 17, 2007 to Communication mailed Jul. 26, 2007", 28 pgs.
"European Application Serial No. 99901368.3, Communication dated Aug. 16, 2000", 2 pgs.
"International Application Serial No. PCT/US00/02324, International Preliminary Examination Report completed Apr. 5, 2001", 14 pgs.

"International Application Serial No. PCT/US00/02324, International Search Report mailed Oct. 20, 2000", 8 pgs.
"International Application Serial No. PCT/US00/02324, Response filed Mar. 1, 2001 to Written Opinion mailed Dec. 1, 2000", 13 pgs.
"International Application Serial No. PCT/US00/02324, Written Opinion mailed Dec. 1, 2000", 6 pgs.
"International Application Serial No. PCT/US00/14548, International Search Report mailed Feb. 1, 2001", 4 pgs.
"International Application Serial No. PCT/US00/14548, Response filed May 20, 2001 to Written Opinion mailed Feb. 27, 2001", 13 pgs.
"International Application Serial No. PCT/US00/14548, Written Opinion mailed Feb. 27, 2001", 7 pgs.
"International Application Serial No. PCT/US00/14548, Written Opinion mailed Jun. 25, 2001", 4 pgs.
"International Application Serial No. PCT/US00/16029, Amendment and Response filed Jun. 26, 2001 to Written Opinion mailed Apr. 26, 2001", 12 pgs.
"International Application Serial No. PCT/US00/16029, International Preliminary Examination Report completed Jul. 24, 2001", 14 pgs.
"International Application Serial No. PCT/US00/16029, International Search Report mailed Feb. 8, 2001", 6 pgs.
"International Application Serial No. PCT/US00/16029, Written Opinion mailed Apr. 26, 2001", 6 pgs.
"International Application Serial No. PCT/US02/31383, International Search Report mailed May 2, 1920", 8 pgs.
"International Application Serial No. PCT/US05/15241, International Search Report mailed Aug. 19, 2005", 3 pgs.
"International Application Serial No. PCT/US07/61919, International Search Report mailed Nov. 7, 2007", 3 pgs.
"International Application Serial No. PCT/US07/61919, Written Opinion mailed Nov. 7, 2007", 8 pgs.
"International Application Serial No. PCT/US2005/015241, International Preliminary Examination Report mailed Nov. 16, 2006", 6 pgs.
"International Application Serial No. PCT/US2005/015241, International Search Report and Written Opinion mailed Sep. 14, 2005", 10 pgs.
"International Application Serial No. PCT/US2005/027474, International Preliminary Examination Report mailed Feb. 15, 2007", 10 pgs.
"International Application Serial No. PCT/US2005/027474, International Search Report and Written Opinion mailed Jan. 25, 2006", 16 pgs.
"International Application Serial No. PCT/US2005/027474, Search Report for mailed Jan. 25, 2006", 5 pgs.
"International Application Serial No. PCT/US2005/027475, International Preliminary Examination Report mailed Feb. 15, 2007", 7 pgs.
"International Application Serial No. PCT/US2005/027475, International Search Report mailed Jan. 23, 2006", 6 pgs.
"International Application Serial No. PCT/US2005/027475, Written Opinion mailed Jan. 23, 2006", 8 pgs.
"International Application Serial No. PCT/US2005/027479, International Preliminary Examination Report mailed Feb. 15, 2007", 12 pgs.
"International Application Serial No. PCT/US2005/027479, International Search Report mailed Sep. 6, 2006", 6 pgs.
"International Application Serial No. PCT/US2005/027479, Written Opinion mailed Sep. 6, 2006", 10 pgs.
"International Application Serial No. PCT/US2007/061867, International Preliminary Examination Report mailed Aug. 21, 2008", 8 pgs.
"International Application Serial No. PCT/US2007/061867, International Search Report mailed Nov. 26, 2007", 3 pgs.
"International Application Serial No. PCT/US2007/061867, Written Opinion mailed Nov. 26, 2007", 8 pgs.
"International Application Serial No. PCT/US2007/061919, International Preliminary Examination Report mailed Aug. 21, 2008", 8 pgs.
"International Application Serial No. PCT/US2008/004553, International Preliminary Examination Report mailed Oct. 22, 2009", 8 pgs.
"International Application Serial No. PCT/US2008/004553, International Search Report mailed Jul. 30, 2008", 2 pgs.
"International Application Serial No. PCT/US2008/004553, Written Opinion mailed Jul. 30, 2008", 7 pgs.
"International Application Serial No. PCT/US99/00366, International Preliminary Examination Report completed Mar. 20, 2000", 9 pgs.
"International Application Serial No. PCT/US99/00366, International Search Report mailed Mar. 20, 2000", 7 pgs.
"International Application Serial No. PCT/US99/00366, Remarks and Response filed Jan. 5, 2000 to Written Opinion mailed Oct. 29, 1999", 2 pgs.
"International Application Serial No. PCT/US99/00366, Written Opinion mailed Oct. 29, 1999", 8 pgs.
"International International Serial No. PCT/US00/14548, Response filed Jul. 23, 2001 to Written Opinion mailed Jun. 25, 2001", 2 pgs.
Abiru, T., et al., "Differential vasodilatory action of 2-octynyladenosine (YT-146), an adenosine A2 receptor agonist, in the isolated rat femoral artery and vein.", Eur J Pharmacol., 281(1), (Jul. 25, 1995), 9-15.
Ali, H., et al., "Methylxanthines Block Antigen-induced Responses in RBL-2H3 Cells Independently of Adenosine Receptors or Cyclic AMP: Evidence for Inhibition of Antigen Binding to IgE", Journal of Pharmacology and Experimental Therapeutics, 258, (1991), 954-962.
Andersson, P., et al., "Anti-anaphylactic and anti-inflammatory effects of xanthines in the lung", Curr. Clin. Pract. Ser., (1985), 187-192.
Andrews, F. J., et al., "Effect of Nonsteroidal Anti-Inflammatory Drugs on LFA-1 and ICAM-1 Expression in Gastric Mucosa", American Journal of Physiology-Gastrointestinal and Liver Physiology, 266, (1994), G657-G664.
Appleyard, C. B., et al., "Tumor Necrosis Factor Mediation of NSAID-Induced Gastric Damage: Role of Leukocyte Adherence", American Journal of Physiology—Gastrointestinal and Liver Physiology, 33, (1996), G42-G48.
Baraldi, Pier G., et al., "Synthesis and Biological Activity of a New Series of N6-Arylcarbamoyl, 2-(Ar)alkynyl-N6-arylcarbamoyl, and N6-Carboxamido derivatives of adenosine-5'-N-ethyluronamide as A1 and A3 Adenosine receptor agonists", Journal of Medicinal Chemistry, 41(17), (Aug. 13, 1998), 3174-3185.
Beck, P. L., et al., "Mechanisms of NSAID-Induced Gastrointestinal Injury Defined Using Mutant Mice", Gastroenterology, 119(3), (2000), 699-705.
Berkich, D. A., et al., "Evidence of Regulated Coupling of A1 Adenosine Receptors by Phosphorylation in Zucker Rats.", American Journal of Physiology, 268(4), (Apr. 1995), E693-E704.
Bhattacharya, S., et al., "Effects of Long-term Treatment With the Allosteric Enhancer, PD81,723, on Chinese Hamster Ovary Cells Expressing Recombinant Human A1 Adenosine Receptors", Molecular Pharmacology, 50(1), (Jul. 1996), 104-111.
Bhattacharya, S., et al., "The Allosteric Enhancer, PD 81,723, Stabilizes Human A1 Adenosine Receptor Coupling to G Proteins", Biochimica et Biophysica Acta, 1265 (1), (Feb. 1995), 15-21.
Bradford, M. M., "A Rapid and Sensitive Method for the Quantitation of Microgram Quantities of Protein Utilizing the Principle of Protein-Dye Binding", Analytical Biochemistry, 72, (1976), 248-254.
Brodie, D. A., et al., "A Study of the Factors Involved in the Production of Gastric Ulcers by the Restraint Technique", Gastroenterology, 38(3), (1960), 353-360.
Cavalcante, I. C, et al., "Effect of Novel A2A Adenosine Receptor Agonist ATL 313 on Clostridium difficile Toxin A-Induced Murine Ileal Enteritis", Infection and Immunity, vol. 74, No. 5, (May 2006), 2606-2612.
Chow, F., et al., "Macrophages in mouse type 2 diabetic nephropathy: correlation with diabetic state and progressive renal injury", Kidney Int., 65(1), XP002593910, ISSN: 0085-2538, (Jan. 2004), 116-28.
Cristalli, G, et al., "Platelet aggregation inhibitory activity of selective A2 Adenosine Receptor Agonists", Nucleosides & Nucleotides, vol. 14 No. 3-5, (1995), 449-453.
Hanlon, W. A., "rTNF alpha Facilitate Human Polymorphonuclear Leukocyte Adherence to Fibrinogen Matrices With Mobilization of Specific and Tertiary But Not Azurophilic Granule Markers", Journal of Leukocyte Biology, 50 (1), (1991), 43-48.

Harada, N., et al., "Adenosine reduces ischemia/reperfusion injury of rat liver by inhibiting leukocyte activation: Involvement of adenosine A2a receptor", Jpn. J. Pharmacol., 79(Suppl), Abstract No. O-214, (1999), 89P.

Okusa, M. D, "A(2A) adenosine receptor: a novel therapeutic target in renal disease", Am J Physiol Renal Physiol., 282(1), XP002593908; ISSN : 0002-9513, (Jan. 2002), F10-8.

Okusa, Mark D, "Attenuation of renal inflammation by adenosine 2A receptor (A2A-AR) activation in ischemia-reperfusion injury (I/R) Regulation adhesion molecule and cytokine expression", 33RD Annual Meeting of the American Society of Nephrology vol. 11, No. Program and A, XP008124542; ISSN : 1046-6673, (Sep. 1, 2000), 132A.

Rieger, J. M, et al., "Design, Synthesis, and Evaluation of Novel A2A Adenosine Receptor Agonists", J. Med. Chem., 44, (2001), 531-539.

Shepherd, R. K, et al., "Adenosine-induced vasoconstriction in vivo. Role of the mast cell and A3 adenosine receptor.", Circ Res., 78(4), (Apr. 1996), 627-34.

Takahashi, T., et al., "Increased spontaneous adherence of neutrophils from type 2 diabetic patients with overt proteinuria: possible role of the progression of diabetic nephropathy.", Diabetes Care, 23(3), XP002593909; ISSN: 0149-5992, (Mar. 2000), 417-8.

"U.S. Appl. No. 10/412,726, Examiner Interview Summary mailed Nov. 30, 2010", 2 pgs.

"U.S. Appl. No. 11/497,280, Examiner Interview Summary mailed Dec. 16, 2009", 2 pgs.

"U.S. Appl. No. 11/765,320, Response filed Jan. 20, 2011 to Non Final Office Action mailed Aug. 20, 2010", 22 pgs.

"U.S. Appl. No. 12/338,599, Supplemental Preliminary Amendment filed Oct. 15, 2010", 3 pgs.

"U.S. Appl. No. 12/487,235, Examiner Interview Summary Dec. 7, 2010", 3 pgs.

"U.S. Appl. No. 12/487,235, Response filed Feb. 18, 2011 to Final Office Action mailed Sep. 20, 2010", 11 pgs.

"U.S. Appl. No. 12/712,022, Non Final Office Action mailed Mar. 23, 2011", 53 pgs.

"U.S. Appl. No. 12/712,022, Non-Final Office Action mailed Nov. 9, 2010", 53 pgs.

"U.S. Appl. No. 12/712,022, Response filed Feb. 7, 2011 to Non Final Office Action mailed Nov. 9, 2010", 27 pgs.

"Australian Application Serial No. 2005267706, Examiner Report mailed on Sep. 16, 2010", 2 Pgs.

"Canadian Application Serial No. 2,460,911, Office Action Response Filed Oct. 14, 2010", 4 pgs.

"Canadian Application Serial No. 2460911, Notice of Allowance mailed Dec. 21, 2010", 1 pg.

"European Application Serial No. 02800432.3, Office Action mailed Dec. 29, 2010", 3 pgs.

"European Application Serial No. 02800432.3, Response filed Mar. 17, 2011 to Non Final Office Action mailed Dec. 29, 2010", 40.

"European Application Serial No. 05756108.6, Office Action mailed Feb. 3, 2011", 7 pgs.

"European Application Serial No. 05803845.6, Communication mailed Oct. 18, 2010", 4 pages.

"European Application Serial No. 05803845.6, Response filed Feb. 9, 2011 to Non Final Office Action mailed Oct. 18, 2010", 3 pgs.

"European Application Serial No. 10181920.9, Extended European Search Report mailed Nov. 30, 2010", 11 pgs.

"International Application Serial No. PCT/US09/30565, International Search Report and Written Opinion mailed Apr. 6, 2009", 7 pgs.

"Japanese Application Serial No. 2000-596019, Office Action Response Filed Nov. 15, 2010", 23 pgs.

"Japanese Application Serial No. 2001-504969, Response filed Jan. 7, 2011 to Office Action mailed Jul. 1, 2010", 3 pgs.

"Japanese Application Serial No. 2007-511486, Office Action mailed Feb. 8, 2011", 4 pgs.

"Singapore Application Serial No. 200706337-3, Response to Written Opinion Filed: Dec. 13, 2010", 15 pgs.

Clerici, C., et al., "Effect of Intraduodenal Administrative of 23-Methyl-UDCA Diastereoisomers on Bile Flow in Hamsters", Digestive Diseases and Sciences, vol. 37, No. 5, (May 1992), 791-798.

Goodwin, Jay T, et al., "Physicochemical Determinants of Passive Membrane Permeability: Role of Solute Hydrogen-Bonding Potential and Volume", J Med Chem, 44, (2001), 3721-3729.

Kerns, Edward, et al., "Drug-Like Properties: Concepts, Structure Design and Methods: From ADME to Toxicity Optimization", Elsevier, (2008), 92:96.

Nogrady, Thomas, et al., "Medicinal Chemistry: A Molecular and Biochemical Approach", Oxford University Press, 3rd Edition, (2005), 135.

Okusa, M. D, et al., "Enhanced protection from renal ischemia-reperfusion injury with A(2A)-adenosine receptor activation and PDE 4 inhibition.", Kidney Int., 59(6), (Jun. 2001), 2114-25.

Okusa, M. D, et al., "Selective A2A adenosine receptor activation reduces ischemia-reperfusion injury in rat kidney", Am J Physiol., 277(3 Pt 2), (Sep. 1999), F404-12.

Remuzon, Philippe, et al., "Fluoronaphthyridines as Antibacterial Agents. 6. Synthesis and Structure-Activity Relationships of New Chiral 7-(1-, 3-, 4-, and 6-Methyl-2, 5-Diazabicyclo [2.2.1] heptan-2-yl]-1-(1,1-dimethylethyl)-6-fluoro-1,4-di-hydro-4-oxo1, 8-naphthyridine-3- . . . ", J Med Chem, 35, (1992), 2898-2909.

Shikata, Kemichi, et al., "Therapies for diabetic nephropathy", Journal of Clinical and Experimental Medicine: 209(1), (Apr. 2004), 54-59.

Silverman, R., et al., "The Organic Chemistry of Drug Design and Drug Action", Academic Press, (1992), 16-17.

"Brazilian Application Serial No. PI 0007864-6, Response filed Sep. 26, 2011 to Office Action mailed May 18, 2011", 12 pgs.

"Chilean Application Serial No. 1609-00, Office Action mailed Sep. 23, 2011", 1 pg.

"U.S. Appl. No. 11/765,320, Non Final Office Action mailed Apr. 15, 2011", 7 pgs.

"U.S. Appl. No. 12/338,599, Notice of Allowance mailed Jun. 28, 2011", 9 pgs.

"U.S. Appl. No. 12/712,022, Final Office Action mailed Aug. 24, 2011", 10 pgs.

"U.S. Appl. No. 12/712,022, Response filed Jun. 23, 2011 to Non Final Office Action mailed Mar. 23, 2011", 19 pgs.

"U.S. Appl. No. 13/027,901, Non Final Office Action mailed Mar. 31, 2011", 15 pgs.

"U.S. Appl. No. 13/027,901, Non Final Office Action mailed Jul. 6, 2011", 8 pgs.

"Brazil Application Serial No. PI 0007864-6,Office Action mailed May 18, 2011", 5 pgs.

"Brazil Application Serial No. PI0011725-0, Office Action mailed Jun. 9, 2011", 4 pgs.

"Canadian Application Serial No. 2,576,826, Office Action mailed Sep. 22, 2011", 4 pgs.

"Chinese Application Serial No. 200580033215.2, Non Final Office Action dated Jul. 4, 2011", 7 pgs.

"European Application Serial No. 05756108.6, Response filed Jul. 20, 2011 to Non Final Office Action dated Feb. 3, 2011", 22 pgs.

"European Application Serial No. 10181920.9, Office Action mailed Jul. 21, 2011", 4 pgs.

"European Divisional Application Serial No. 10181920.9, Response filed Jun. 29, 2011 to EP Search Report dated Nov. 30, 2010", 53 pgs.

"Japanese Application Serial No. 2001-504939, Final Office Action mailed Jul. 29, 2011", 6 pgs.

"Japanese Application Serial No. 2007-511486, Office Action Response filed Aug. 5, 2011 to Office Action mailed Feb. 23, 2011", 29 pgs.

"Japanese Application Serial No. 2007-524924, Office Action mailed Sep. 16, 2011", 3 pgs.

"New Zealand Application Serial No. 585697, Non Final Office Action dated Aug. 29, 2011", 2 pgs.

"New Zealand Application Serial No. 585697, Response filed Aug. 11, 2011 to Examination Report dated Jun. 3, 2010", 3 pgs.

"New Zealand Application Serial No. 585697, Response filed Sep. 28, 2011 to Office Action mailed Aug. 31, 2011", 13 pgs.

"Singapore Application Serial No. 200706337-3, Response to Written Opinion filed Oct. 3, 2011", 13 pgs.

"Singapore Application Serial No. 200706337-3, Office Action mailed May 3, 2011", 10 pgs.

* cited by examiner

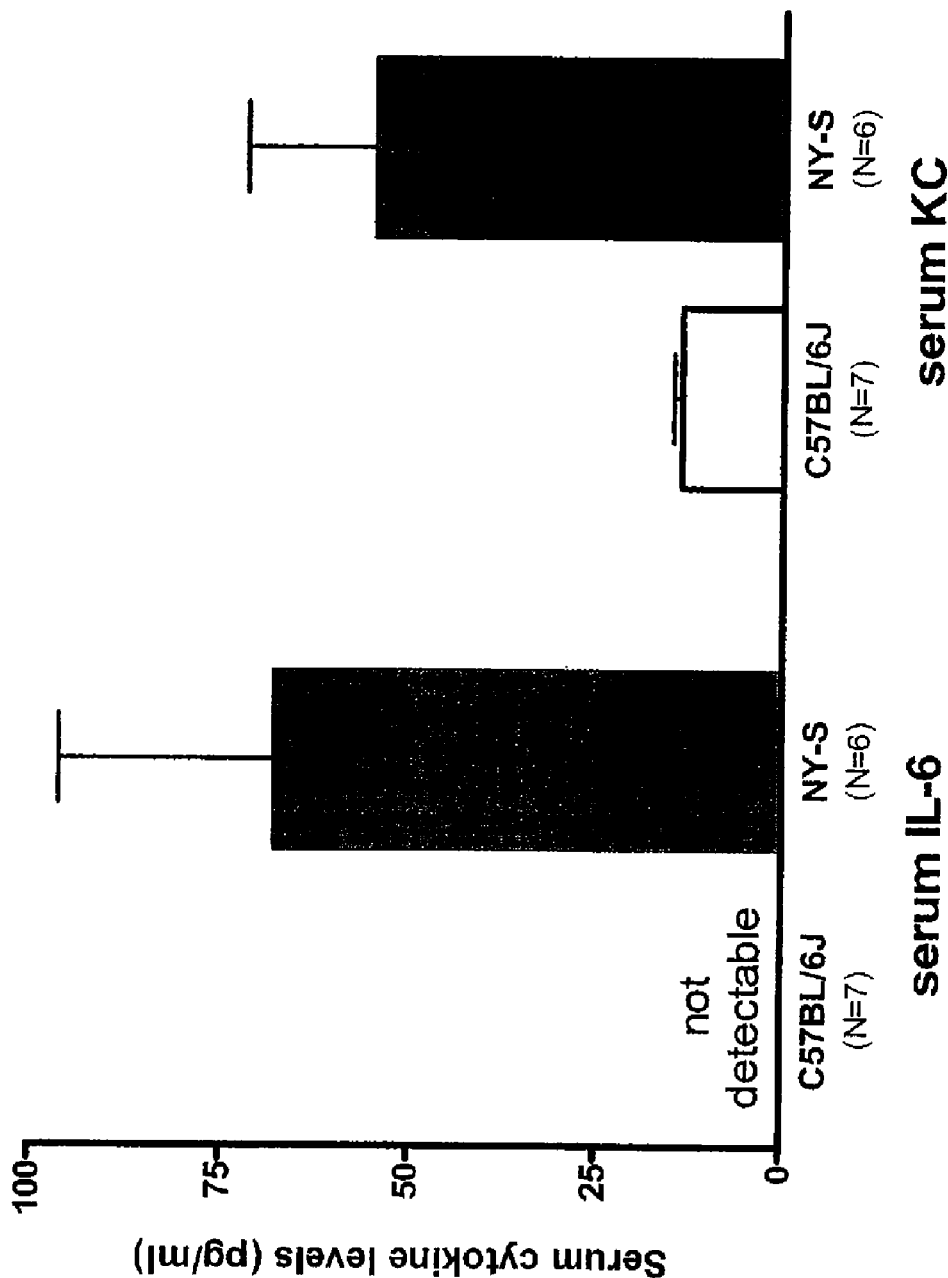

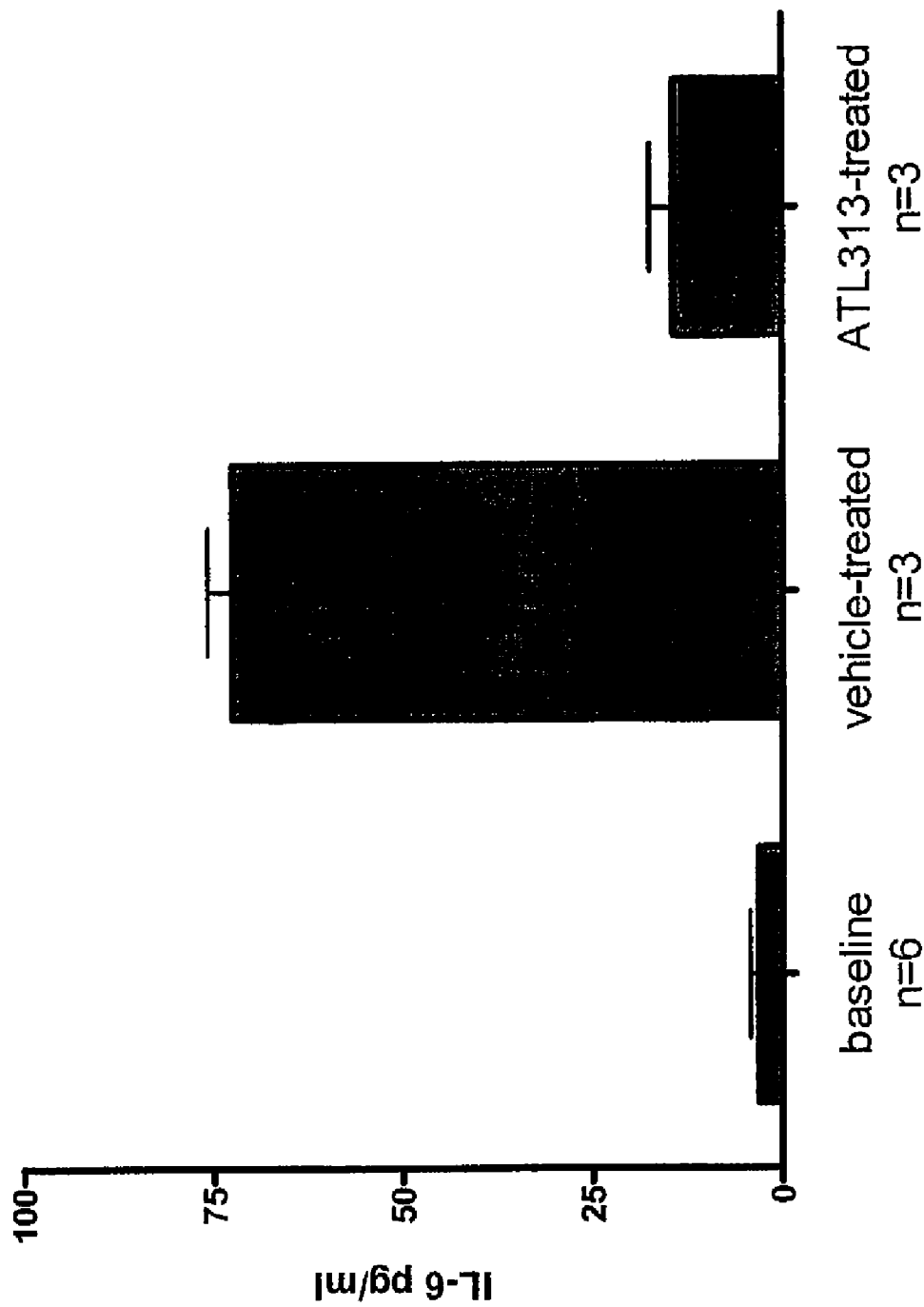

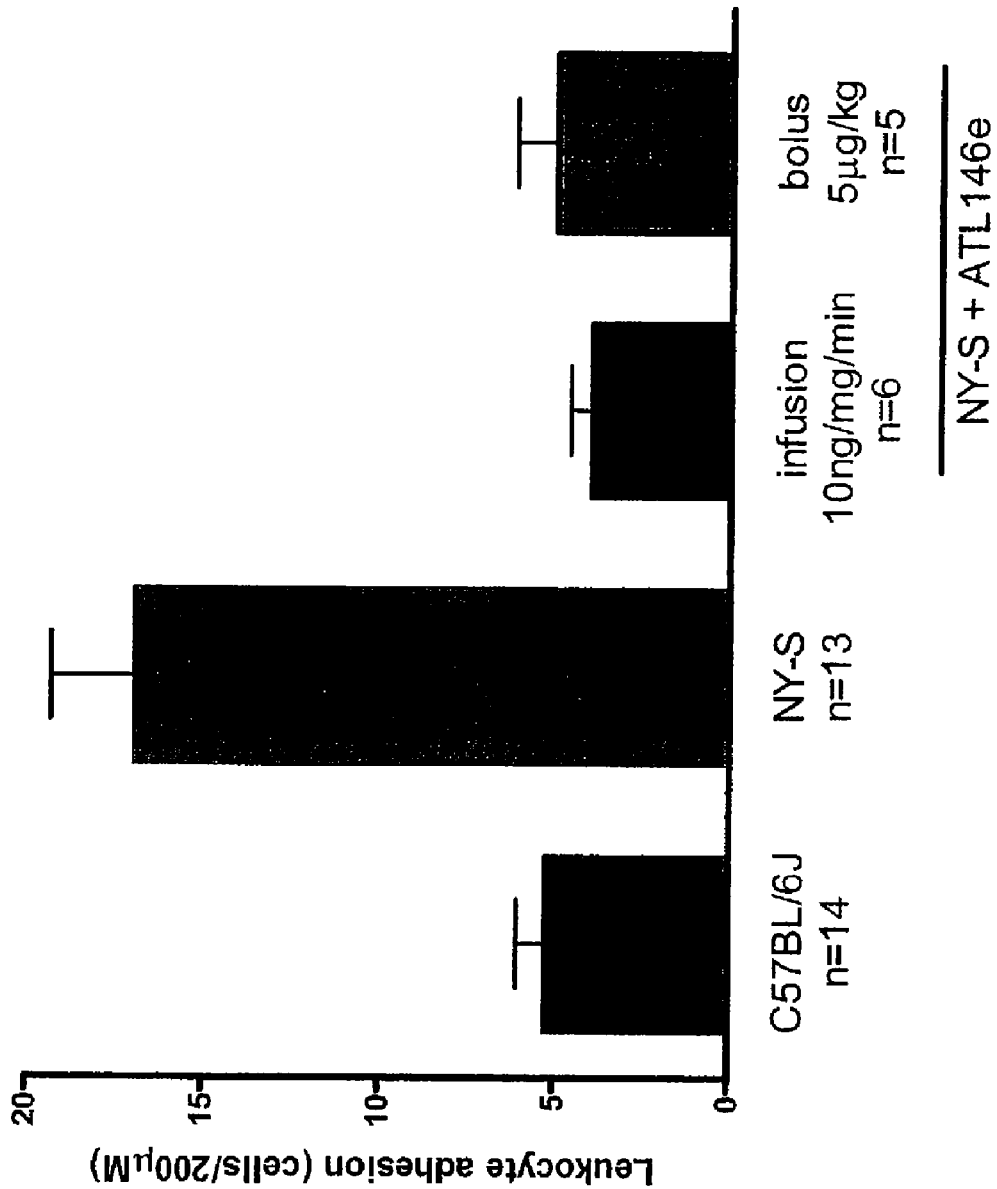
Fig 3. Effect of continuous infusion or bolus injection of ATL146e on leukocyte adhesion in NY-S mice

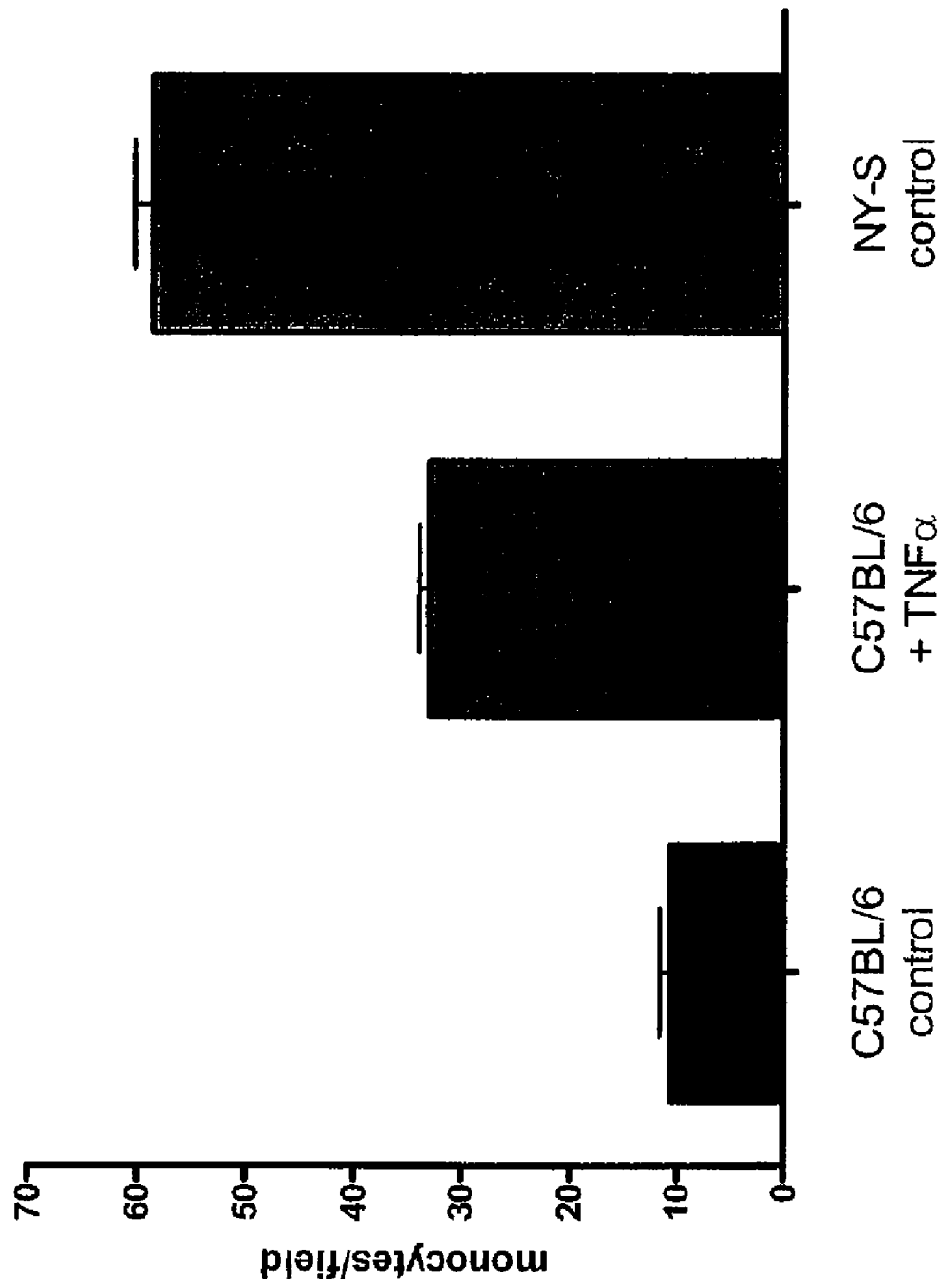

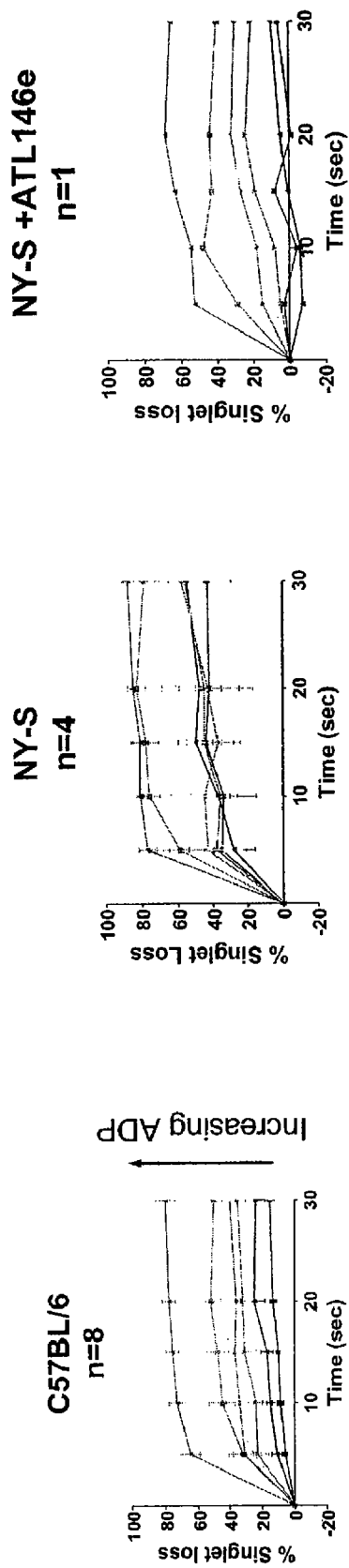
Figure 5: ATL146e reduces the hypersensitivity of platelets from NY-S mice

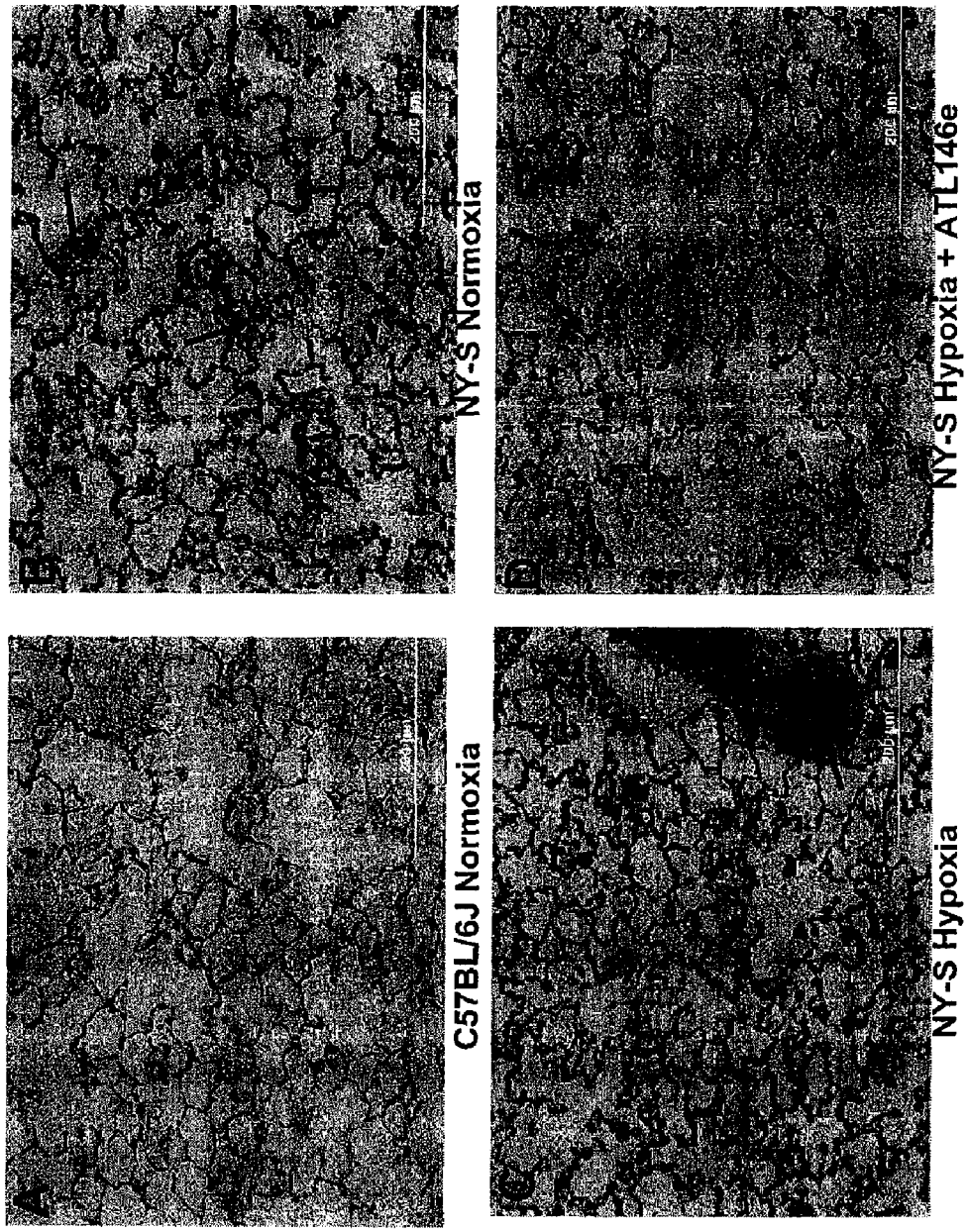
Figure 6. ATL146e alleviates hypoxia-induced vascular congestion

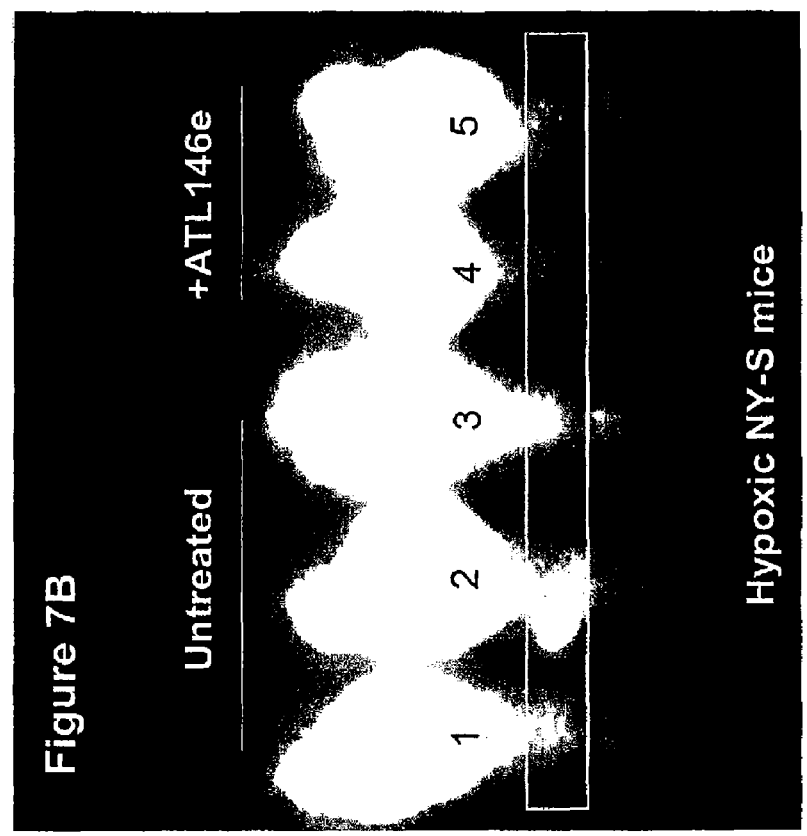
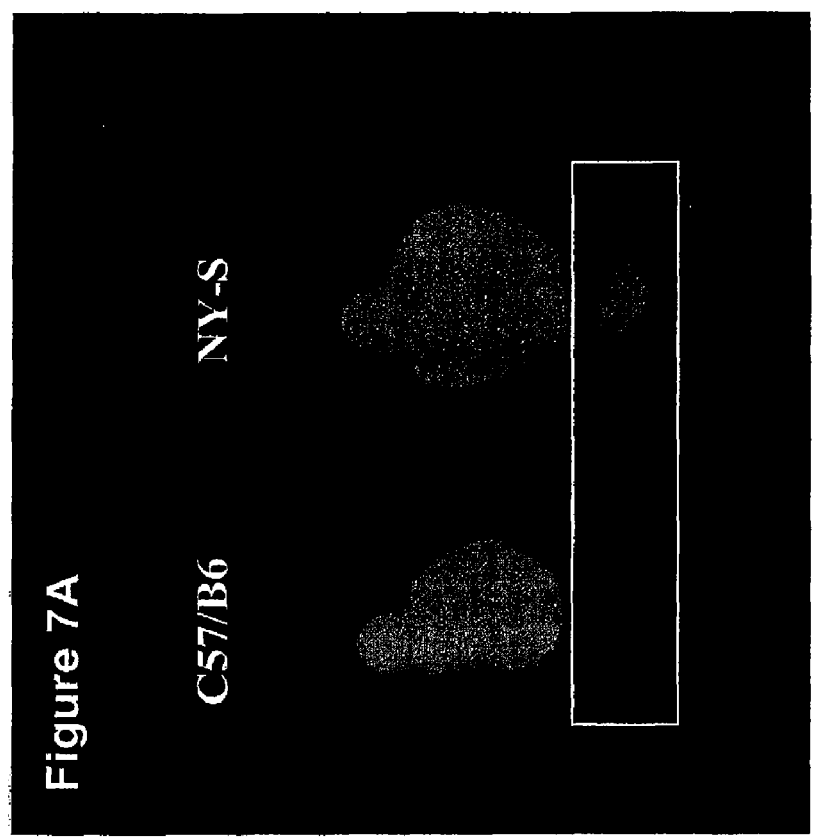

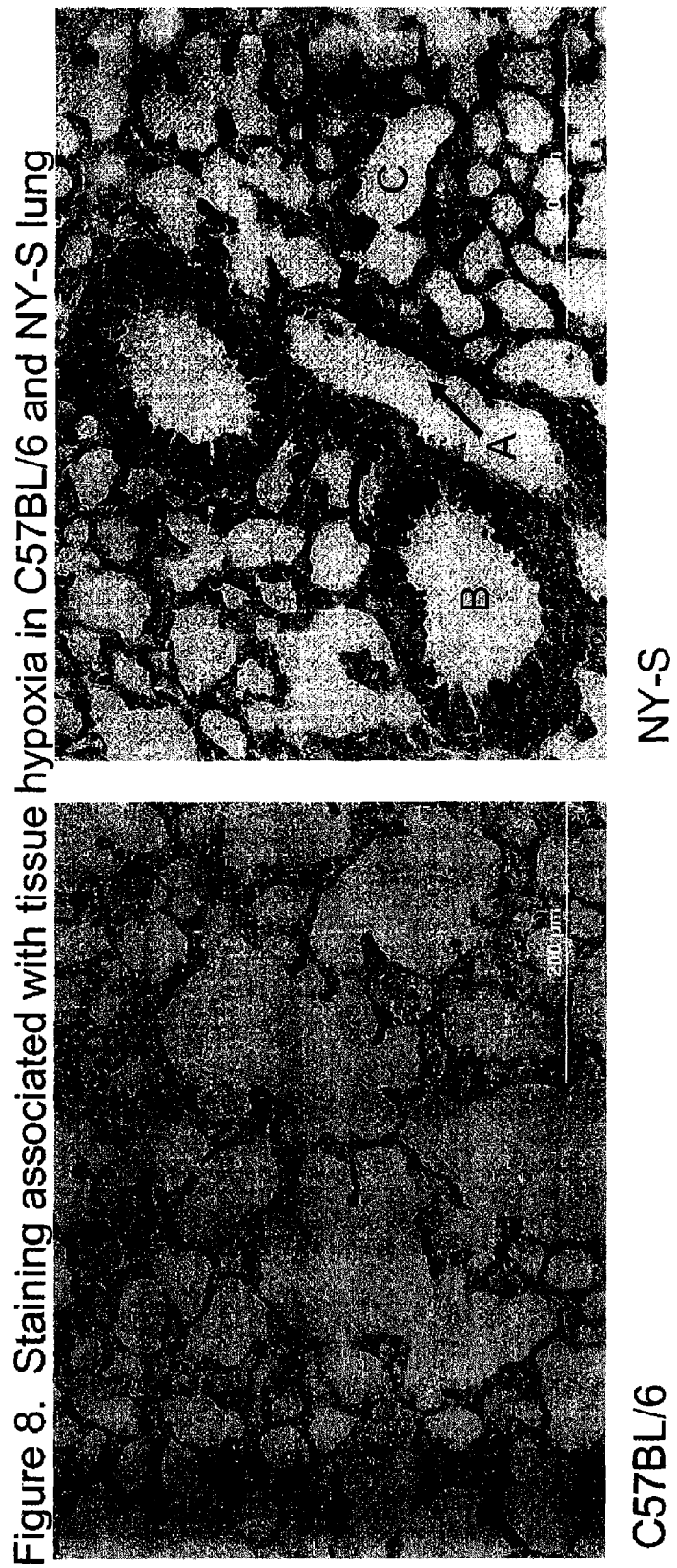
Figure 8. Staining associated with tissue hypoxia in C57BL/6 and NY-S lung

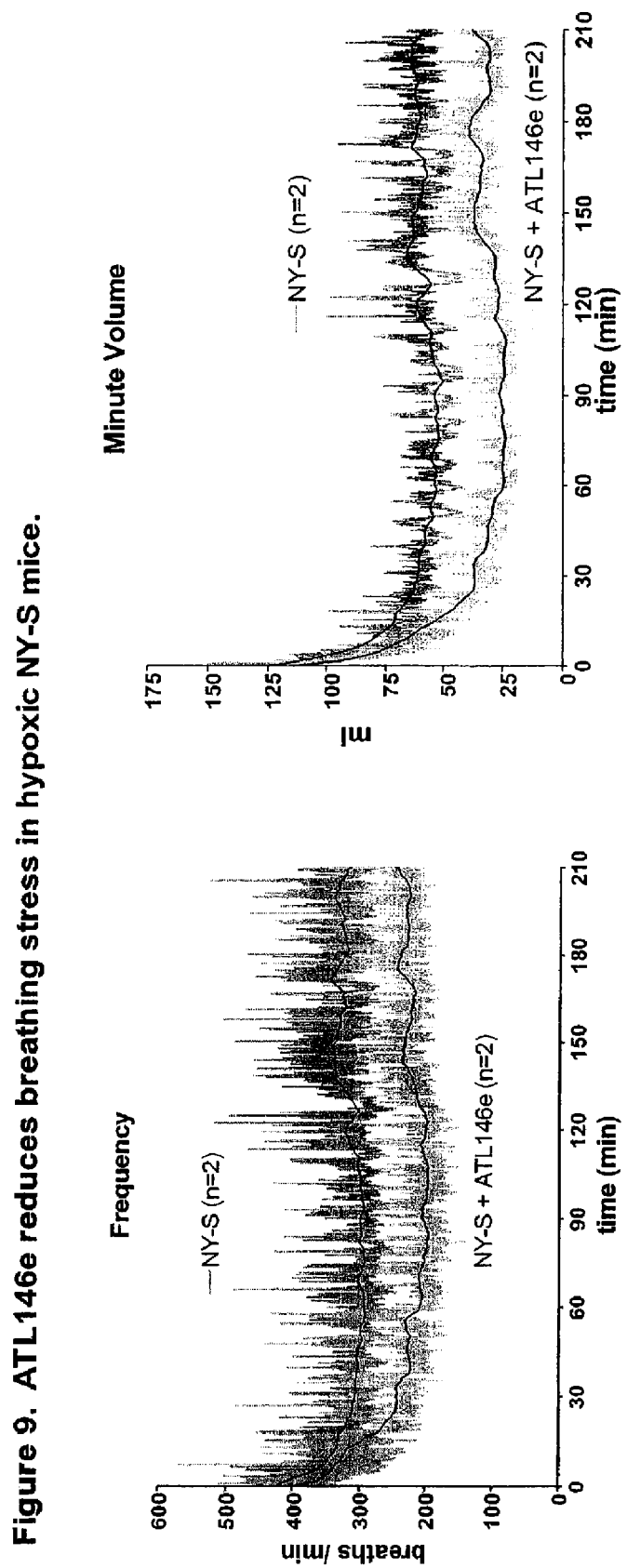
Figure 9. ATL146e reduces breathing stress in hypoxic NY-S mice.

METHOD TO TREAT SICKLE CELL DISEASE

RELATED APPLICATION

This application claims priority from U.S. Provisional Application Ser. No. 60/772,603 filed Feb. 10, 2006, the contents of the provisional application is incorporated herein by reference in its entirety.

STATEMENT OF GOVERNMENT RIGHTS

This invention was made with the assistance of government support under United States Grant No. P01 HL073361 from the National Institutes of Health. The government may have certain rights to the invention.

BACKGROUND OF THE INVENTION

Sickle Cell Disease (SCD) results from a single nucleotide mutation in hemoglobin that causes red cell sickling. It presents clinically as repeated occurrences of painful vaso-occlusive crises (i.e., pain crisis), acute chest syndrome, cerebrovascular accidents, splenic dysfunction and renal dysfunction (*Am. J. Epidem.* 2000, 151(9):839-845). This disorder is prevalent in over 72,000 individuals in the United States and over 2 million individuals world-wide. Over 2 million Americans are believed to carry the sickle cell allele.

Pain associated with a vaso-occlusive crisis among patients with SCD is a common reason for emergency department visits and hospitalization. Acute pain in patients with SCD is ischemic in nature and results from the occlusion of microvascular beds. Clinical data indicate that more than five percent of patients with SCD have from three to ten episodes of painful vaso-occlusive crises per year. In many patients a vaso-occlusive episode will typically be resolved in about a week. In some cases, severe episodes may persist for several weeks or even months. An ischemia-reperfusion injury can also contribute to cumulative organ damage in SCD. In addition, irreversible organ damage can result from recurrent ischemic insults and may lead to acute chest syndrome, renal hypertrophy and isosthenuria (inability to concentrate urine), autoinfarction of the spleen, chronic skin ulcers, osteonecrosis, priapism and cerebrovascular accident.

Sickle Cell Disease has historically been viewed as a disease of red cell abnormalities. Recently, it has been suggested that the wide spectrum of clinical manifestations of this disease result in part from chronic inflammation. This concept is supported by evidence that SCD patients demonstrate many clinical symptoms of chronic inflammation such as increased cytokine levels, the presence of circulating endothelial cells, increased white blood cell counts and an increase in cellular markers of leukocyte and endothelial activation.

Currently, acute sickle crises are managed primarily with analgesics. Standard treatment is palliative and consists primarily of opioids, hydration, rest and behavioral therapies. The pain associated with vaso-occlusive crisis is often undertreated due to the concerns of the physician with respect to narcotic addiction, tolerance, respiratory depression and excessive sedation.

Hydroxyurea is currently the only FDA approved drug for treating Sickle Cell Disease. Hydroxyurea is an S-phase cytotoxic drug and is used for long-term therapy. It is believed to increase the levels of hemoglobin F which prevents formation of S-polymers and red cell sickling. It is also believed to increase NO production. A multi-center trial of hydroxyurea in adults with Sickle Cell Disease showed that hydroxyurea reduced the incidence of painful episodes by nearly half. However, presently hydroxyurea is used only in patients who suffer severe complications of SCD and who are capable of following the daily dosage regimes. The general belief is that Hydroxyurea therapy is effective only if given in a structured environment with a high potential for compliance. In addition, many SCD patients are refractory to Hydroxyurea.

There is a need for new therapies for treating disorders caused by Sickle Cell Disease. Current therapies are marginally effective and have undesirable side effects.

SUMMARY OF THE INVENTION

The present invention provides a therapeutic method for treating acute inflammatory event in a patient with sickle cell disease, comprising administering to a patient in need thereof a therapeutically effective amount of an $A_{2A}$ adenosine receptor agonist. The invention further comprises treating the patient with an $A_{2A}$ adenosine receptor agonist in combination with a Type IV phosphodiesterase (PDE) inhibitor, which can cause synergistic decreases in the inflammatory response mediated by leukocytes.

The agonists of $A_{2A}$ adenosine receptors of the invention can inhibit neutrophil, macrophage, platelet and T cell activation and thereby reduce inflammation caused autoimmune responses. The effects of adenosine $A_{2A}$ agonists can be enhanced by type IV phosphodiesterase inhibitors such as rolipram.

The invention also provides compounds of the invention for use in medical therapy (e.g., for use as an adjunct in the treatment of an inflammatory response, caused by sickle cell crises), with $A_{2A}$ adenosine receptor agonists, as well as the use of a compound of the invention for the manufacture of a medicament for reducing inflammation caused by a sickle cell crisis.

The invention also provides a pharmaceutical composition comprising an effective amount of the compound of the invention, e.g., formula I, or a pharmaceutically acceptable salt thereof, in combination with a pharmaceutically acceptable diluent or carrier, and optionally, in combination with a Type IV phosphodiesterase (PDE) inhibitor. In one embodiment, the composition is presented as a unit dosage form.

Additionally, the invention provides a therapeutic method for treating a pathological condition or symptom in a mammal, such as a human, wherein the activity of $A_{2A}$ adenosine receptors is implicated and agonism of said receptors is desired, comprising administering to a mammal in need of such therapy, an effective amount of a compound of the invention, e.g., formula I, or a pharmaceutically acceptable salt thereof. It is believed that activation of $A_{2A}$ adenosine receptors inhibits inflammation by affecting neutrophils, mast cells, monocytes/macrophages, platelets T-cells and/or eosinophils. Inhibition of these inflammatory cells results in tissue protection following tissue insults.

BRIEF DESCRIPTION OF THE FIGURES

FIG. 1 illustrates that the serum levels of the pro-inflammatory cytokines IL-6 and KC are elevated at baseline in NY-S mice.

FIG. 2 illustrates a rise serum IL-6 levels in NY-S mice in response to hypoxia-reperfusion injury.

FIG. 3 illustrates the effect of ATL146e on leukocyte adhesion.

FIG. 4 illustrates the WEHI cell adhesion to murine aortic endothelial cells.

FIGS. 5A-5C illustrate aggregation, measured as singlet loss (reduction in the number of single platelets), in platelet-rich plasma prepared from the blood of wild type and NY-S mice in response to activation by increasing concentrations of ADP (0-10 µM).

FIGS. 6A-6D illustrates representative sections from hematoxylin- and eosin-stained (H&E), inflation-fixed lung tissue from C57BL/6 and NY-S mice.

FIGS. 7A and 7B illustrate hypoxia-sensitive tracer accumulation in the tissues of hypoxic C57BL/6 and NY-S mice.

FIGS. 8A and 8B illustrate sections from C57BL/6 and NY-S lungs stained with the 2-nitroimidazole, pimonidazole hydrochloride.

FIGS. 9A and 9B illustrate the pulmonary function of mice during and after exposure to hypoxic air.

DETAILED DESCRIPTION OF THE INVENTION

The following definitions are used, unless otherwise described. Halo is fluoro, chloro, bromo, or iodo. Alkyl, alkoxy, aralkyl, alkylaryl, etc. denote both straight and branched alkyl groups; but reference to an individual radical such as "propyl" embraces only the straight chain radical, a branched chain isomer such as "isopropyl" being specifically referred to. Aryl includes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

Specific values listed below for radicals, substituents, and ranges, are for illustration only; they do not exclude other defined values or other values within defined ranges for the radicals and substituents.

Specifically, $(C_1-C_8)$alkyl can be methyl, ethyl, propyl, isopropyl, butyl, iso-butyl, sec-butyl, t-butyl, pentyl, 3-pentyl, hexyl, heptyl or octyl. As used herein, the term "cycloalkyl" encompasses bicycloalkyl (norbornyl, 2.2.2-bicyclooctyl, etc.) and tricycloalkyl (adamantyl, etc.), optionally comprising 1-2 N, O or S. Cycloalkyl also encompasses (cycloalkyl)alkyl. Thus, $(C_3-C_6)$cycloalkyl can be cyclopropyl, cyclobutyl, cyclopentyl, cyclohexyl and the like. $(C_1-C_8)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl $(CO_2R^2)$ can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio, $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazolyl, pyrazolyl, pyrrolyl, pyrazinyl, tetrazolyl, pyridyl (or its N-oxide), thienyl, pyrimidinyl (or its N-oxide), indolyl, isoquinolyl (or its N-oxide) or quinolyl (or its N-oxide).

Aryl denotes a phenyl radical or an ortho-fused bicyclic carbocyclic radical having about nine to ten ring atoms in which at least one ring is aromatic. Heteroaryl denotes a radical of a monocyclic aromatic ring containing five or six ring atoms consisting of carbon and 1, 2, 3, or 4 heteroatoms each selected from the group consisting of non-peroxide oxygen, sulfur, and N(Y) wherein Y is absent or is H, O, $(C_1-C_8)$ alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

The term "heterocycle" generally represents a non aromatic heterocyclic group, having from 3 to about 10 ring atoms, which can be saturated or partially unsaturated, containing at least one heteroatom (e.g., 1, 2, or 3) selected from the group consisting of oxygen, nitrogen, and sulfur. Specific, "heterocycle" groups include monocyclic, bicyclic, or tricyclic groups containing one or more heteroatoms selected from the group consisting of oxygen, nitrogen, and sulfur. A "heterocycle" group also can include one or more oxo groups (=O) attached to a ring atom. Non-limiting examples of heterocycle groups include 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, thiomorpholine, and the like.

The term "alkylene" refers to a divalent straight or branched hydrocarbon chain (e.g. ethylene —$CH_2CH_2$—).

The term "aryl$(C_1-C_8)$alkylene" for example includes benzyl, phenethyl, 3-phenylpropyl, naphthylmethyl and the like.

As used herein the term "in conjunction with" refers to co-administration of an anti-rejection agent with the $A_{2A}$ adenosine receptor agonist. The co-administration of an agent and an $A_{2A}$ adenosine receptor agonists includes administration of the agent and agonist either simultaneously, as a mixture, or sequentially. The sequential administration of the $A_{2A}$ adenosine receptor agonists can be prior to administration of the agent, within minutes or up to about 48 hours either before the administration of the agent. The $A_{2A}$ adenosine receptor agonists can also be administered after the agent. In one embodiment the administration of the $A_{2A}$ adenosine receptor agonists will be within about 24 hours, such as within about 12 hours.

The carbon atom content of various hydrocarbon-containing moieties is indicated by a prefix designating the minimum and maximum number of carbon atoms in the moiety, i.e., the prefix $C_i$-$C_j$ indicates a moiety of the integer "i" to the integer "j" carbon atoms, inclusive. Thus, for example, $(C_1-C_8)$alkyl refers to alkyl of one to eight carbon atoms, inclusive.

The compounds of the present invention are generally named according to the IUPAC or CAS nomenclature system. Abbreviations which are well known to one of ordinary skill in the art may be used (e.g., "Ph" for phenyl, "Me" for methyl, "Et" for ethyl, "h" for hour or hours and "rt" for room temperature).

In one embodiment, $A_{2A}$ agonist refers to an agent that activates the Adenosine $A_{2A}$ receptor with a Ki of <1 µM. An $A_{2A}$ agonist may be selective for $A_{2A}$ (e.g., at least 10, 50, or 100/1 over another adenosine receptor subtype/$A_{2A}$ receptor). An $A_{2A}$ agonist may also be cross reactive with other adenosine receptor subtypes (e.g., $A_1$, $A_{2B}$, and $A_3$). The $A_{2A}$ agonist may activate other receptors with a greater or lesser affinity than the $A_{2A}$ receptor.

In one embodiment, the present invention provides a method for treating acute inflammatory events in a patient with sickle cell disease, comprising administering to a patient in need thereof a therapeutically effective amount of an $A_{2A}$ adenosine receptor agonist. The acute inflammatory event can be associated with an acute vaso-occlusive or ischemic episode. The acute inflammatory event can be selected from: vaso-occlusive crises (i.e., pain crises), acute chest syndrome, cerebrovascular accident, splenic dysfunction, and renal dysfunction.

In one embodiment, an $A_{2A}$ agonist can be combined with one or more agents or additional therapeutic methods, including hydroxyurea, Decitibine, ICA 17043, transfusion, and analgesics.

In another embodiment, agonists of $A_{2A}$ adenosine receptors that are useful in the practice of the present invention include compounds having the formula (I):

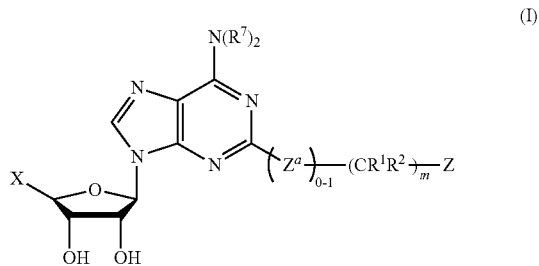

(I)

wherein
$Z^a$ is C≡C, O, NH, or NHN=$CR^{3a}$;
Z is $CR^3R^4R^5$ or $NR^4R^5$; each $R^1$ is independently hydrogen, halo, —$OR^a$, —$SR^a$, ($C_1$-$C_8$)alkyl, cyano, nitro, trifluoromethyl, trifluoromethoxy, ($C_3$-$C_8$)cycloalkyl, heterocycle, heterocycle($C_1$-$C_8$)alkylene-, aryl, aryl($C_1$-$C_8$)alkylene-, heteroaryl, heteroaryl($C_1$-$C_8$)alkylene-, —$CO_2R^a$, $R^aC$(=O)O—, $R^aC$(=O)—, —$OCO_2R^a$, $R^bR^cNC$(=O)O—, $R^aOC$(=O)N($R^b$)—, $R^bR^cN$—, $R^bR^cNC$(=O)—, $R^aC$(=O)N($R^b$)—, $R^bR^cNC$(=O)N($R^b$)—, $R^bR^cNC$(=S)N($R^b$)—, —$OPO_3R^a$, $R^aOC$(=S)—, $R^aC$(=S)—, —$SSR^a$, $R^aS$(=O)—, $R^aS$(=O)$_2$—, or —N=$NR^b$;

each $R^2$ is independently hydrogen, halo, ($C_1$-$C_8$)alkyl, ($C_3$-$C_8$)cycloalkyl, heterocycle, heterocycle($C_1$-$C_8$)alkylene-, aryl, aryl($C_1$-$C_8$)alkylene-, heteroaryl, or heteroaryl($C_1$-$C_8$)alkylene-;

alternatively, $R^1$ and $R^2$ and the atom to which they are attached is C=O, C=S or C=$NR^d$, $R^4$ and $R^5$ are independently H or ($C_1$-$C_8$)alkyl;

alternatively, $R^4$ and $R^5$ together with the atom to which they are attached form a saturated, partially unsaturated, or aromatic ring that is mono-, bi- or polycyclic and has 3, 4, 5, 6, 7, 8, 9 or 10 ring atoms optionally having 1, 2, 3, or 4 heteroatoms selected from non-peroxide oxy (—O—), thio (—S—), sulfinyl (—SO—), sulfonyl (—S(O)$_2$—) or amine (—$NR^b$—) in the ring;

wherein $R^4$ and $R^5$ are independently substituted with 0-3 $R^6$ groups or any ring comprising $R^4$ and $R^5$ is substituted with from 0 to 14 $R^6$ groups; wherein each $R^6$ is independently hydrogen, halo, —$OR^a$, —$SR^a$, ($C_1$-$C_8$)alkyl, cyano, nitro, trifluoromethyl, trifluoromethoxy, ($C_1$-$C_8$)cycloalkyl, ($C_6$-$C_{12}$)bicycloalkyl, heterocycle, heterocycle ($C_1$-$C_8$)alkylene-, aryl, aryl ($C_1$-$C_8$)alkylene-, heteroaryl, heteroaryl($C_1$-$C_8$)alkylene-, —$CO_2R^a$, $R^aC$(=O)O—, $R^aC$(=O)—, —$OCO_2R^a$, $R^bR^cNC$(=O)O—, $R^aOC$(=O)N($R^b$)—, $R^bR^cN$—, $R^bR^cNC$(=O)—, $R^aC$(=O)N($R^b$)—, $R^bR^cNC$(=O)N($R^b$)—, $R^bR^cNC$(=S)N($R^b$)—, —$OPO_3R^a$, $R^aOC$(=S)—, $R^aC$(=S)—, —$SSR^a$, $R^aS$(=O)—, —$NNR^b$, or two $R^6$ groups and the atom to which they are attached is C=O, C=S; or two $R^6$ groups together with the atom or atoms to which they are attached can form a carbocyclic or heterocyclic ring comprising from 1-6 carbon atoms and 1, 2, 3, or 4 heteroatoms selected from non-peroxide oxy (—O—), thio (—S—), sulfinyl (—SO—), sulfonyl (—S(O)$_2$—) or amine (—$NR^b$—) in the ring;

$R^3$ is hydrogen, halo, —$OR^a$, —$SR^a$, ($C_1$-$C_8$)alkyl, cyano, nitro, trifluoromethyl, trifluoromethoxy, ($C_3$-$C_8$)cycloalkyl, heterocycle, heterocycle($C_1$-$C_8$)alkylene-, aryl, aryl($C_1$-$C_8$)alkylene-, heteroaryl, heteroaryl($C_1$-$C_8$)alkylene-, —$CO_2R^a$, $R^aC$(=O)O—, $R^aC$(=O)—, —$OCO_2R^a$, $R^bR^cNC$(=O)O—, $R^aOC$(=O)N($R^b$)—, $R^bR^cN$—, $R^bR^cNC$(=O)—, $R^aC$(=O)N($R^b$)—, $R^bR^cNC$(=O)N($R^b$)—, $R^bR^cNC$(=S)N($R^b$)—, —$OPO_3R^a$, $R^aOC$(=S)—, $R^aC$(=S), —$SSR^a$, $R^aS$(=O)—, $R^aS$(=O)$_2$—, —$NNR^b$; or if the ring formed from $CR^4R^5$ is aryl or heteroaryl or partially unsaturated then $R^3$ can be absent;

$R^{3a}$ is hydrogen, ($C_1$-$C_8$)alkyl, or aryl;

each $R^7$ is independently hydrogen, ($C_1$-$C_8$)alkyl, ($C_3$-$C_8$) cycloalkyl, aryl, aryl($C_1$-$C_8$)alkylene, heteroaryl, or heteroaryl($C_1$-$C_8$)alkylene-;

X is —$CH_2OR^a$, —$CO_2R^a$, —$CH_2OC$(O)$R^a$, —C(O)$NR^bR^c$, —$CH_2SR^a$, —C(S)$OR^a$, —$CH_2OC$(S)$R^a$, —C(S)$NR^bR^c$, or —$CH_2N(R^b)(R^c)$;

alternatively, X is an aromatic ring of the formula:

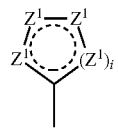

each $Z^1$ is non-peroxide oxy (—O—), S(O)$_{0-2}$, —C($R^8$)—, or amine (—$NR^8$—), provided that at least one $Z^1$ is non-peroxide oxy (—O—), thio (—S—), sulfinyl (—SO—), sulfonyl (—S(O)$_2$—) or amine (—$NR^8$—);

each $R^8$ is independently hydrogen, ($C_1$-$C_8$)alkyl, ($C_1$-$C_8$) alkenyl, ($C_3$-$C_8$)cycloalkyl, ($C_3$-$C_8$)cycloalkyl($C_1$-$C_8$)alkylene, ($C_3$-$C_8$)cycloalkenyl, ($C_3$-$C_8$)cycloalkenyl($C_1$-$C_8$)alkylene, aryl, aryl($C_1$-$C_8$)alkylene, heteroaryl, or heteroaryl($C_1$-$C_8$)alkylene, wherein any of the alkyl or alkenyl groups of $R^8$ are optionally interrupted by —O—, —S—, or —N($R^a$)—;

wherein any of the alkyl, cycloalkyl, heterocycle, aryl, or heteroaryl, groups of $R^1$, $R^2$, $R^3$, $R^{3a}$, $R^6$, $R^7$ and $R^8$ is optionally substituted on carbon with one or more (e.g. 1, 2, 3, or 4) substituents selected from the group consisting of halo, —$OR^a$, —$SR^a$, ($C_1$-$C_8$)alkyl, cyano, nitro, trifluoromethyl, trifluoromethoxy, ($C_3$-$C_8$)cycloalkyl, ($C_6$-$C_{12}$)bicycloalkyl, heterocycle, heterocycle($C_1$-$C_8$)alkylene-, aryl, aryloxy, aryl ($C_1$-$C_8$)alkylene-, heteroaryl, heteroaryl($C_1$-$C_8$)alkylene-, —$CO_2R^a$, $R^aC$(=O)O—, $R^aC$(=O)—, —$OCO_2R^a$, $R^bR^cNC$(=O)O—, $R^aOC$(=O)N($R^b$)—, $R^bR^cN$—, $R^bR^cNC$(=O)—, $R^aC$(=O)N($R^b$)—, $R^bR^cNC$(=O)N($R^b$)—, $R^bR^cNC$(=S)N($R^b$)—, —$OPO_3R^a$, $R^aOC$(=S)—, $R^aC$(=S)—, —$SSR^a$, $R^aS$(=O)$_p$—, $R^bR^cNS$(O)$_p$—, and —N=$NR^b$;

wherein any (C₁-C₈)alkyl, (C₃-C₈)cycloalkyl, (C₆-C₁₂)bi-cycloalkyl, (C₁-C₈)alkoxy, (C₁-C₈)alkanoyl, (C₁-C₈)alkylene, or heterocycle, is optionally partially unsaturated;

each $R^a$, $R^b$ and $R^c$ is independently hydrogen, (C₁-C₁₂)alkyl, (C₁-C₈)alkoxy-(C₁-C₁₂)alkyl, (C₃-C₈)cycloalkyl, (C₁-C₈)alkylthio, amino acid, aryl, aryl(C₁-C₈)alkylene, heteroaryl, or heteroaryl(C₁-C₈)alkylene;

alternatively $R^b$ and $R^c$, together with the nitrogen to which they are attached, form a pyrrolidino, piperidino, morpholino, or thiomorpholino ring;

$R^d$ is hydrogen or (C₁-C₆)alkyl;

i is 1 or 2 m is 0 to 8; and p is 0 to 2;

provided that m is at least 1 when Z is $NR^4R^5$; or a pharmaceutically acceptable salt thereof.

Specific values listed below for radicals, substituents, and ranges, are for illustration only; they do not exclude other defined values or other values within defined ranges for the radicals and substituents.

For example, specific values include compounds having the formula (Ia):

(Ia)

wherein $R^1$ is hydrogen, —OH, —CH₂OH, —OMe, —OAc, —NH₂, —NHMe, —NMe₂ or —NHAc;

$R^2$ is hydrogen, (C₁-C₈)alkyl, cyclopropyl, cyclohexyl or benzyl;

$R^3$ is hydrogen, OH, OMe, OAc, NH₂, NHMe, NMe₂ or NHAc;

$CR^4R^5$ or $NR^4R^5$ is optionally substituted with 0-2 $R^6$ groups and is cyclopentane, cyclohexane, piperidine, dihydro-pyridine, tetrahydro-pyridine, pyridine, piperazine, tetrahydro-pyrazine, dihydro-pyrazine, pyrazine, dihydro-pyrimidine, tetrahydro-pyrimidine, hexahydro-pyrimidine, pyrazine, imidazole, dihydro-imidazole, imidazolidine, pyrazole, dihydro-pyrazole, and pyrazolidine;

alternatively, the ring $CR^4R^5$ or $NR^4R^5$ is optionally substituted with 0-4 (e.g., 0 to 2) $R^6$ groups and is selected from the group consisting of:

$R^6$ is hydrogen, (C₁-C₈)alkyl, —$OR^a$, —$CO_2R^a$, $R^aC(=O)$—, $R^aC(=O)O$—, $R^bR^cN$—, $R^bR^cNC(=O)$—, or aryl;

$R^a$, $R^b$ and $R^c$ are independently hydrogen, (C₃-C₄)-cycloalkyl, (C₁-C₈)alkyl, aryl or aryl(C₁-C₈)alkylene;

each $R^7$ is independently hydrogen, alkyl (e.g., C₁-C₈-alkyl), aryl, aryl(C₁-C₈)alkylene or heteroaryl(C₁-C₈)alkylene;

$R^8$ is methyl, ethyl, propyl, 2-propenyl, cyclopropyl, cyclobutyl, cyclopropylmethyl, —(CH₂)₂CO₂CH₃, or —(CH₂)₂₋₃OH;

X is —CH₂$OR^a$, —$CO_2R^a$, —CH₂OC(O)$R^a$, or —C(O)$NR^bR^c$;

alternatively X is selected from:

and m is 0, 1 or 2;

or a pharmaceutically acceptable salt thereof.

Additional specific values include compounds having the formula (Ia), wherein:

$R^1$ is hydrogen, OH, OMe, or NH₂;

$R^2$ is hydrogen, methyl, ethyl or propyl;

$R^3$ is hydrogen, OH, OMe, or NH₂;

the ring $CR^4R^5$ or $NR^4R^5$ is selected from the group consisting of:

-continued

[chemical structures]

where q is from 0 to 4 (e.g., 0-2);
$R^6$ is hydrogen, $(C_1-C_8)$alkyl, —$OR^a$, —$CO_2R^a$, $R^aC(=O)$—, $R^aC(=O)O$—, $R^bR^cN$—, $R^bR^cNC(=O)$—, or aryl;
$R^a$ and $R^b$ are independently hydrogen, methyl, ethyl, propyl, butyl, ethylhexyl, cyclopropyl, cyclobutyl, phenyl or benzyl;
$N(R^7)_2$ is amino, methylamino, dimethylamino; ethylamino; pentylamino, diphenylethylamino, (pyridinylmethyl)amino, (pyridinyl)(methyl)amino, diethylamino or benzylamino; and,
$R^8$ is methyl, ethyl, propyl, or cyclopropyl;
X is —$CH_2OR^a$ or —$C(O)NR^bR^c$;
alternatively, X is selected from:

[chemical structures]

or a pharmaceutically acceptable salt thereof

Additional specific values include compounds having the formula (Ia), wherein:
$R^1$ is hydrogen, OH, or $NH_2$;
$R^2$ is hydrogen or methyl;
$R^3$ is hydrogen, OH, or $NH_2$;
the ring $CR^4R^5$ or $NR^4R^5$ is selected from the group consisting of:

[chemical structures]

-continued

[chemical structures]

where q is from 0 to 2;
$R^6$ is hydrogen, methyl, ethyl, t-butyl, phenyl, —$CO_2R^a$—$CONR^bR^c$, or $R^aC(=O)$—;
$R^b$ is H;
$R^a$ is methyl, ethyl, propyl, butyl, pentyl, ethylhexyl cyclopropyl, and cyclobutyl;
—$N(R^7)_2$ is amino, methylamino, dimethylamino; ethylamino; diethylamino or benzylamino;
or a pharmaceutically acceptable salt thereof.

Additional specific values include compounds having the formula (Ia), wherein:
$R^1$ is hydrogen or OH;
$R^2$ is hydrogen;
$R^3$ is hydrogen or OH;
the ring $CR^4R^5$ or $NR^4R^5$ is selected from the group consisting of:

[chemical structures]

$R^6$ is hydrogen, methyl, ethyl, —$CO_2R^a$, and —$CONR^bR^c$;
$R^b$ is H;
$R^a$ is methyl, ethyl, i-propyl, i-butyl, tert-butyl, and cyclopropyl;

N(R⁷)₂ is amino, or methylamino;

X is —CH₂OH,

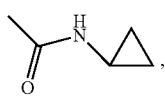

C(O)NHCH₃, or —C(O)NHCH₂CH₃;

or a pharmaceutically acceptable salt thereof.

Additional specific values include compounds wherein: the ring comprising R⁴, R⁵ and the atom to which they are connected is 2-methyl cyclohexane, 2,2-dimethylcyclohexane, 2-phenylcyclohexane, 2-ethylcyclohexane, 2,2-diethylcyclohexane, 2-tert-butyl cyclohexane, 3-methyl cyclohexane, 3,3-dimethylcyclohexane, 4-methyl cyclohexane, 4-ethylcyclohexane, 4-phenyl cyclohexane, 4-tert-butyl cyclohexane, 4-carboxymethyl cyclohexane, 4-carboxyethyl cyclohexane, 3,3,5,5-tetramethyl cyclohexane, 2,4-dimethyl cyclopentane, 4-cyclohexanecarboxylic acid, 4-cyclohexanecarboxylic acid esters, 4-methyloxyalkanoyl-cyclohexane, 4-piperidine-1-carboxylic acid methyl ester, 4-piperidine-1-carboxylic acid tert-butyl ester 4-piperidine, 4-piperazine-1-carboxylic acid methyl ester, 4-piperidine-1-carboxylic acid tert-butylester, 1-piperidine-4-carboxylic acid methyl ester, 1-piperidine-4-carboxylic acid tert-butyl ester, tert-butylester, 1-piperidine-4-carboxylic acid methyl ester, or 1-piperidine-4-carboxylic acid tert-butyl ester, 3-piperidine-1-carboxylic acid methyl ester, 3-piperidine-1-carboxylic acid tert-butyl ester, 3-piperidine, 3-piperazine-1-carboxylic acid methyl ester, 3-piperidine-1-carboxylic acid tert-butylester, 1-piperidine-3-carboxylic acid methyl ester, or 1-piperidine-3-carboxylic acid tert-butyl ester;

or a pharmaceutically acceptable salt thereof.

Additional specific values include compounds 1-33 represented in Table A or a pharmaceutically acceptable salt thereof:

TABLE A

| Ex. # | Rᶜ | R⁷ | —(R¹)ₘ—Z |
|---|---|---|---|
| 1. | Et | H | 4-(methoxycarbonyl)cyclohexylmethyl |
| 2. | cPr | H | 1-(methoxycarbonyl)piperidin-4-ylmethyl |
| 3. | Et | H | 1-(methoxycarbonyl)piperidin-4-ylmethyl |
| 4. | Et | H | 1-(ethoxycarbonyl)piperidin-4-ylmethyl |
| 5. | Et | H | 1-(isobutoxycarbonyl)piperidin-4-ylmethyl |
| 6. | Et | H | 4-(ethoxycarbonyl)piperazin-1-ylmethyl |
| 7. | Et | H | 4-(isobutoxycarbonyl)piperazin-1-ylmethyl |
| 8. | Et | H | 4-((methoxycarbonyloxy)methyl)cyclohexylmethyl |

TABLE A-continued
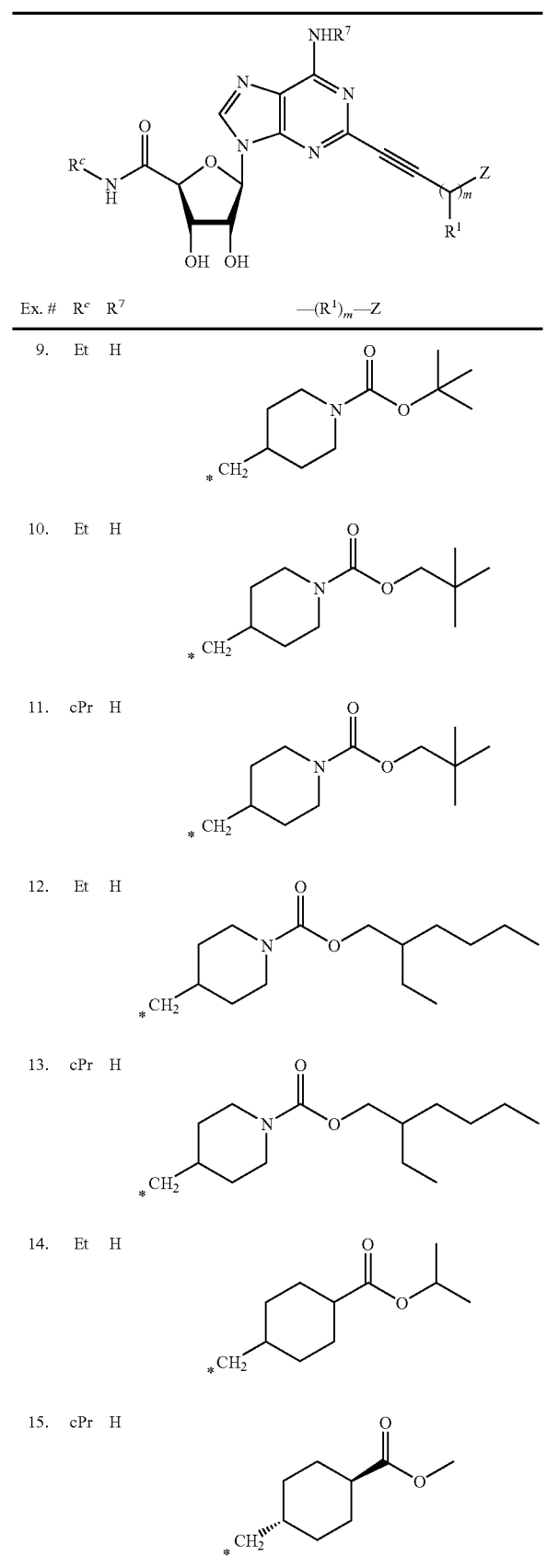
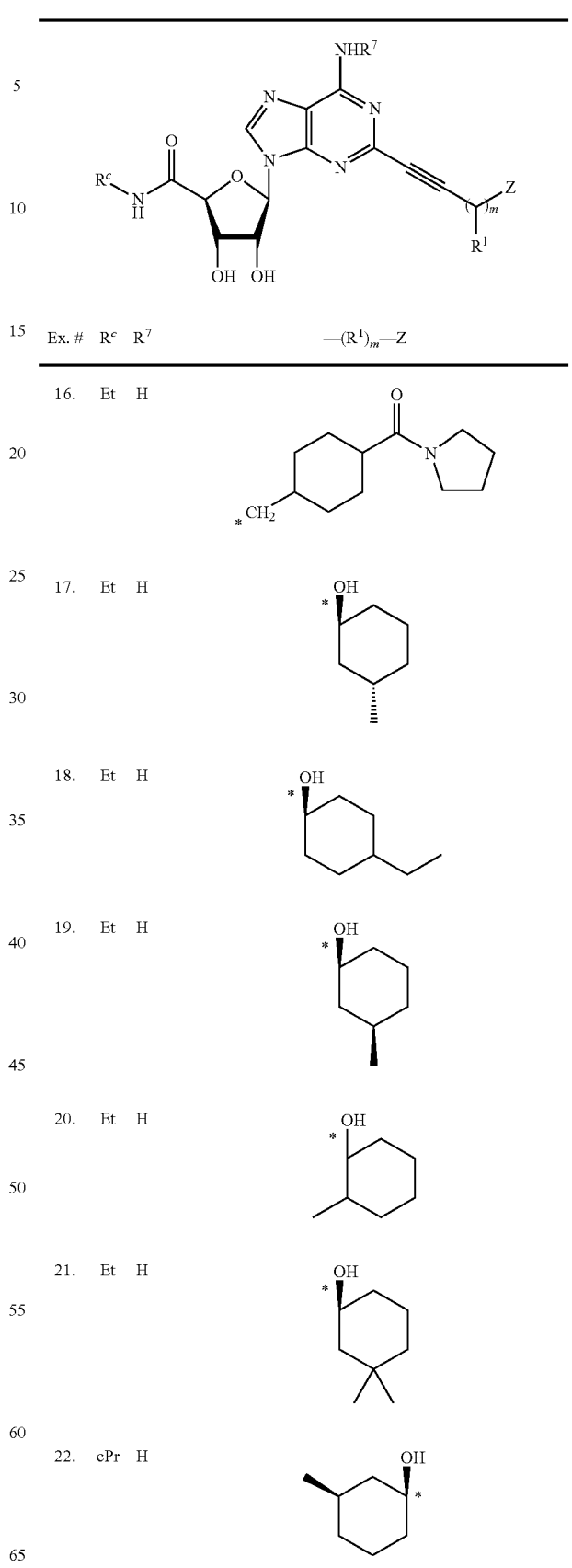

TABLE A-continued
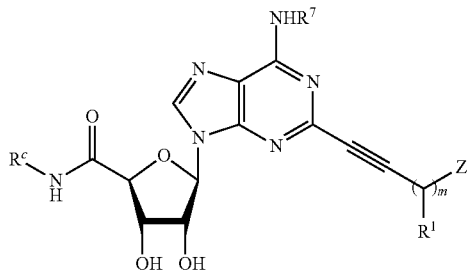
| Ex. # | R$^c$ | R$^7$ | —(R$^1$)$_m$—Z |
|---|---|---|---|
| 23. | Et | H | 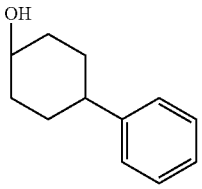 |
| 24. | Et | H | 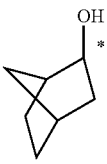 |
| 25. | cPr | H | 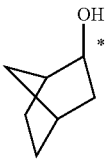 |
| 26. | cPr | H | 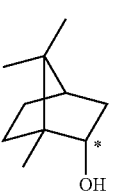 |
| 27. | Et | H | 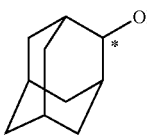 |
| 28. | cPr | H | 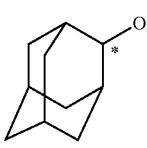 |
| 29. | Et | H | 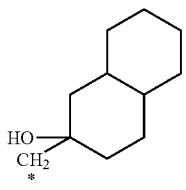 |
TABLE A-continued
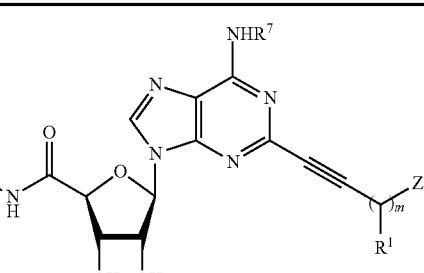
| Ex. # | R$^c$ | R$^7$ | —(R$^1$)$_m$—Z |
|---|---|---|---|
| 30. | cPr | H | 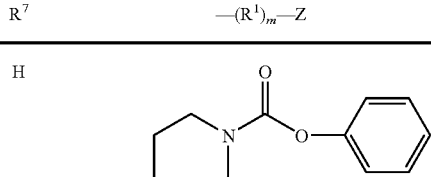 |
| 31. | Et | H | 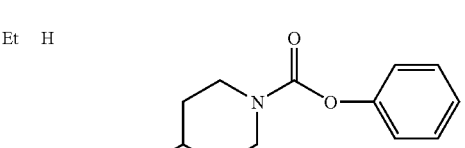 |
| 32. | cPr | H | 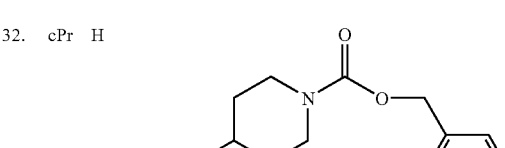 |
| 33. | Et | H | 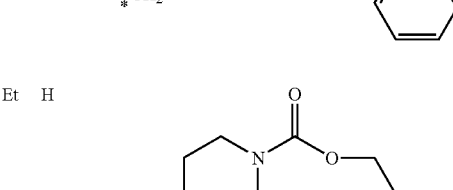 |
*signifies the point of attachment.
Additional specific values include compounds having the formula (Ib)-(Id) or a pharmaceutically acceptable salt thereof:
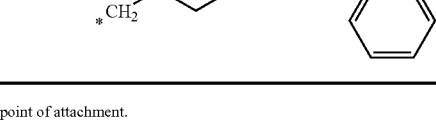 (Ib)
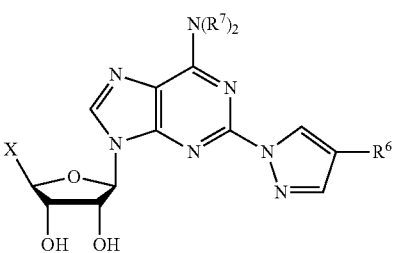

-continued

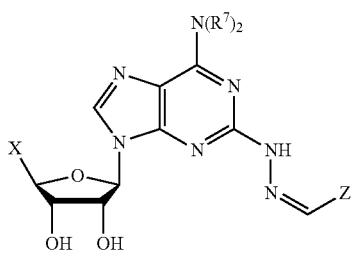
(Ic)

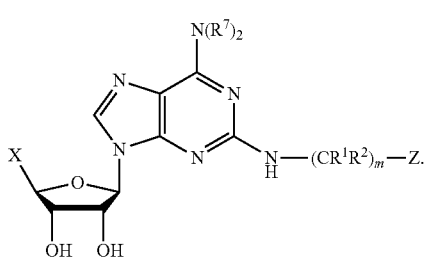
(Id)

A group of specific compounds of formula (Ia) are those wherein each $R^7$ is H, X is ethylaminocarbonyl, $R^1$ and $R^2$ are each hydrogen, and Z is a 4-piperidyl-1-carboxylic acid or ester group, wherein $R^a$ is methyl, ethyl, propyl, isopropyl, isobutyl, or t-butyl, 4.

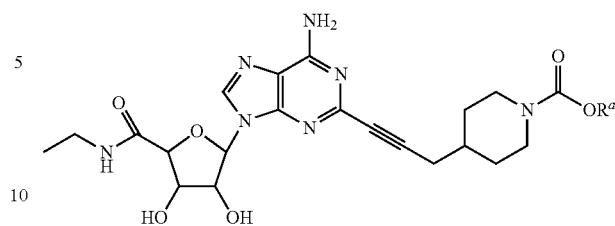

Specific $A_{2A}$ adenosine receptor agonists suitable for use with the present invention include those described in U.S. Pat. No. 6,232,297 and in U.S. Patent Application No. 2003/0186926 A1.

Specific compounds of the invention include formula (IA)

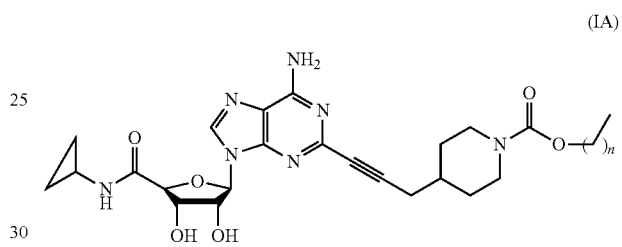
(IA)

In formula (IA) n is 0, 1, 2, 3, 4, 5, 6, 7, 8, 9, 10, 11, 12, 13, 14, 15, 16, 17, or 18. In another group of specific compounds n is, 5, 6, 7, 8, 9, 10, 11, 12, 13, 14, 15, 16, 17, or 18.

Specific compounds of the invention include formula (IB)

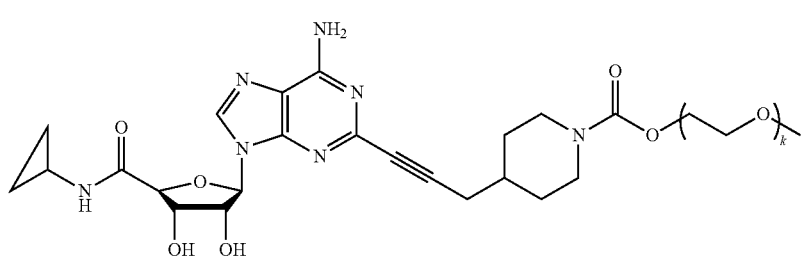
(IB)

In formula (IB) k is 1, 2, 3, 4, 5, 6, 7, 8, 9, 10, 11, 12, 13, 14, 15, 16, 17, or 18.

Specific compounds of the invention include formula (IC)

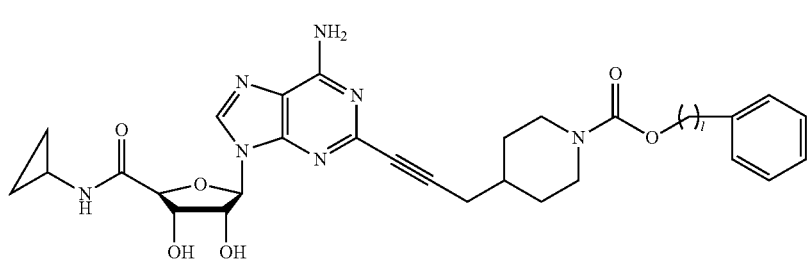
(IC)

In formula (IC) 1 is 0, 1, 2, 3, or 4.
Other specific compounds of the invention include

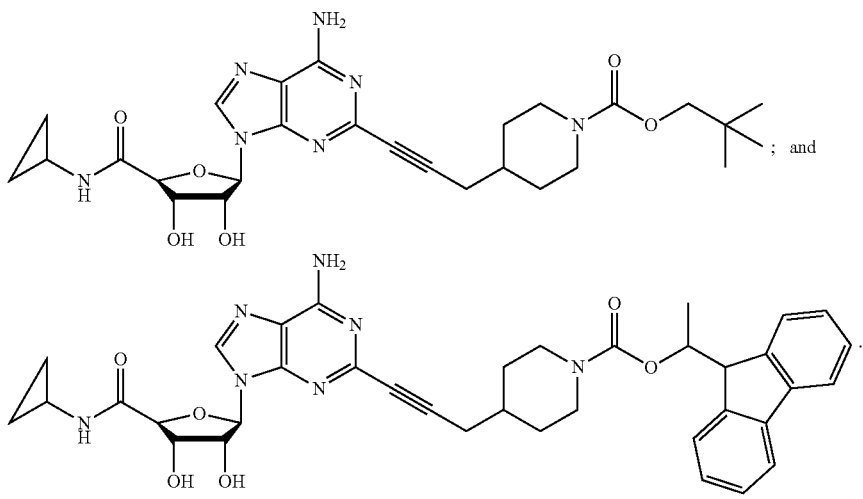

Examples of compounds useful in practicing the invention are illustrated in tables 1, 2, and 3 below:

TABLE 1

| Compound | R | $R^1$ | $R^2$ | $R^6$ |
|---|---|---|---|---|
| ATL2037 | NECA | H | H | $CH_2OH$ |
| MP9056 | NECA | OH | H | $CH_2OH$ |
| ATL146a | NECA | H | H | $CO_2H$ |
| MP9057 | NECA | OH | H | $CO_2H$ |
| ATL146e | NECA | H | H | $CO_2Me$ |
| MP9058 | NECA | OH | H | $CO_2Me$ |
| JR2145 | $CH_2OH$ | H | H | $CO_2Me$ |
| MP9059 | $CH_2OH$ | OH | H | $CO_2Me$ |
| ATL193 | NECA | H | H | $CH_2OAc$ |
| MP9060 | NECA | OH | H | $CH_2OAc$ |
| JR2147 | $CH_2OH$ | H | H | $CH_2OAc$ |
| MP9061 | $CH_2OH$ | OH | H | $CH_2OAc$ |
| JR3023 | NECA | H | H | $CH_2N(CH_3)_2$ |
| MP9062 | NECA | OH | H | $CH_2N(CH_3)_2$ |
| JR3021 | NECA | H | H | $COOCH_2CH_2NHBoc$ |
| MP9063 | NECA | OH | H | $COOCH_2CH_2NHBoc$ |
| JR3033 | NECA | H | H | $COOCH_2CH_2NH_2$ |
| MP9064 | NECA | OH | H | $COOCH_2CH_2NH_2$ |
| JR3037 | NECA | H | H | $CONHCH_2CH_3$ |
| MP9065 | NECA | OH | H | $CONHCH_2CH_3$ |
| JR3055 | NECA | H | H | $CONH_2$ |
| MP9072 | NECA | OH | H | $CONH_2$ |
| JR3065 | NECA | H | H | CONHMe |
| MP9066 | NECA | OH | H | CONHMe |
| JR3067B | NECA | H | H | Me, cis $CO_2Me$ |
| MP9067 | NECA | OH | H | Me, cis $CO_2Me$ |
| JR3067A | NECA | H | H | Me, trans $CO_2Me$ |
| MP9068 | NECA | OH | H | Me, trans $CO_2Me$ |
| JR3087 | NECA | H | H | $CH_2CH_3$ |
| MP9069 | NECA | OH | H | $CH_2CH_3$ |

TABLE 1-continued

| Compound | R | $R^1$ | $R^2$ | $R^6$ |
|---|---|---|---|---|
| JR3159A | NECA | OH | H | H |
| JR3159B | NECA | OH | H | H |
| JR3119 | NECA | H | H | $COCH_3$ |
| MP9070 | NECA | OH | H | $COCH_3$ |
| JR3121 | NECA | H | H | $CHCH_3(OH)$ |
| MP9071 | NECA | OH | H | $CHCH_3(OH)$ |
| JR3139 | NECA | OH | $C_6H_{11}$ | H |

NECA = $CH_3CH_2N(H)C(O)$—

TABLE 2

| Compound | $R^1$ | $R^2$ | $R^6$ |
|---|---|---|---|
| JR3261 | H | H | H |
| JR3259 | H | H | $CO_2tBu$ |
| JR3269 | H | H | $CO_2Et$ |
| JR4011 | H | H | $CO_2iBu$ |
| JR4009 | H | H | $CO_2iPr$ |

TABLE 2-continued

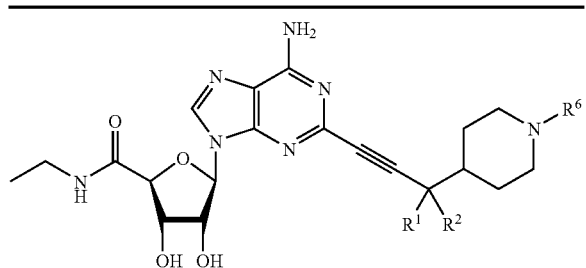

| Compound | R$^1$ | R$^2$ | R$^6$ |
|---|---|---|---|
| JR4007 | H | H | COMe |
| JR4051 | H | H | COC(CH$_3$)$_3$ |
| JR4047 | H | H | COCH$_2$(CH$_3$)$_3$ |
| MP9047 | H | H | COCH$_3$ |
| MP9048 | H | H | C(O)N(CH$_3$)$_2$ |
| MP9049 | H | H | C(O)N(CH$_3$)Et |
| MP9050 | H | H | C(O)N(CH$_3$)iPr |
| MP9051 | H | H | C(O)N(CH$_3$)iBu |
| MP9052 | H | H | C(O)NH(CH$_3$) |
| MP9053 | H | H | C(O)NH(Et) |
| MP9054 | H | H | C(O)NH(iPr) |
| MP9055 | H | H | C(O)NH(iBu) |
| TX3261 | OH | H | H |
| TX3259 | OH | H | CO$_2$tBu |
| TX3269 | OH | H | CO$_2$Et |
| TX4011 | OH | H | CO$_2$iBu |
| TX4009 | OH | H | CO$_2$iPr |
| TX4007 | OH | H | COMe |
| TX4051 | OH | H | COC(CH$_3$)$_3$ |
| TX4047 | OH | H | COCH$_2$(CH$_3$)$_3$ |
| TX9047 | OH | H | COCH$_3$ |
| TX9048 | OH | H | C(O)N(CH$_3$)$_2$ |
| TX9049 | OH | H | C(O)N(CH$_3$)Et |
| TX9050 | OH | H | C(O)N(CH$_3$)iPr |
| TX9051 | OH | H | C(O)N(CH$_3$)iBu |
| TX9052 | OH | H | C(O)NH(CH$_3$) |
| TX9053 | OH | H | C(O)NH(Et) |
| TX9054 | OH | H | C(O)NH(iPr) |
| TX9055 | OH | H | C(O)NH(iBu) |

TABLE 3

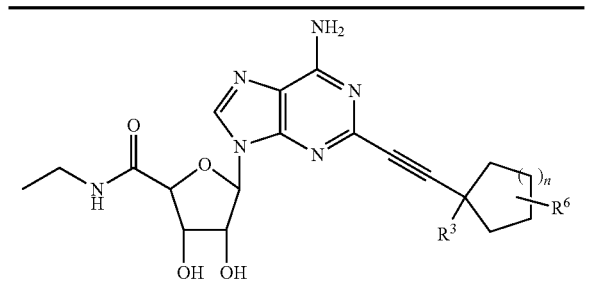

| Compound | n | R$^3$ | R$^6$ |
|---|---|---|---|
| JR3135 | 1 | OH | H |
| JR3089 | 2 | OH | H |
| JR3205 | 2 | NH$_2$ | H |
| JR3177A | 2 | OH | 2-CH$_3$ |
| JR3177B | 2 | OH | 2-CH$_3$ |
| JR3181A | 2 | OH | 2-CH$_3$ |
| JR3181B | 2 | OH | 2-CH$_3$ |
| JR3227 | 2 | OH | 2-C(CH$_3$)$_3$ |
| JR9876 | 2 | OH | 2-C$_6$H$_5$ |
| JR3179 | 2 | OH | 3-CH$_3$ |
| JR3221 | 2 | OH (R) | 3-CH$_3$ (R) |
| ATL203 | 2 | OH (S) | 3-CH$_3$ (R) |
| MP9041 | 2 | OH (R) | 3-CH$_3$ (S) |
| MP9042 | 2 | OH (S) | 3-CH$_3$ (S) |
| JR3201B | 2 | OH | 3-(CH$_3$)$_2$ |

TABLE 3-continued

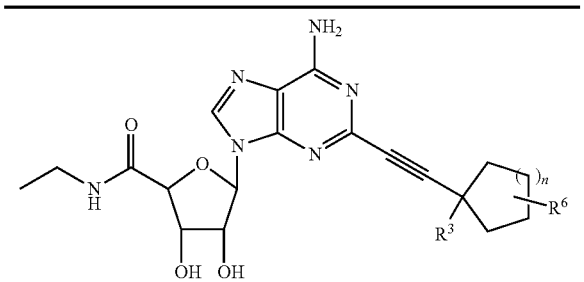

| Compound | n | R$^3$ | R$^6$ |
|---|---|---|---|
| MP9043 | 2 | OH (R) | 3-CH$_2$CH$_3$ (R) |
| MP9044 | 2 | OH (S) | 3-CH$_2$CH$_3$ (R) |
| MP9045 | 2 | OH (R) | 3-CH$_2$CH$_3$ (S) |
| MP9046 | 2 | OH (S) | 3-CH$_2$CH$_3$ (S) |
| JR3163 | 2 | OH | 3-(CH$_3$)$_2$, 5-(CH$_3$)$_2$ |
| JR9875 | 2 | OH | 4-CH$_3$ |
| JR3149 | 2 | OH | 4-C$_2$H$_5$ |
| JR3203 | 2 | OH | 4-C(CH$_3$)$_3$ |
| JR3161 | 2 | OH | 4-C$_6$H$_5$ |

In another embodiment, agonists of A$_{2A}$ adenosine receptors that are useful in the practice of the present invention include compounds having the formula (II):

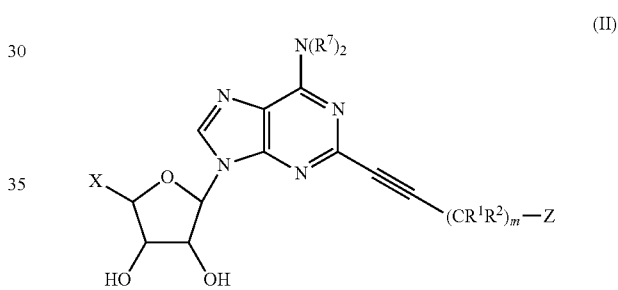

wherein Z is CR$^3$R$^4$R$^5$; each R$^1$, R$^2$ and R$^3$ is hydrogen; R$^4$ and R$^5$ together with the carbon atom to which they are attached form a cycloalkyl ring having 3, 4, 5, 6, 7, 8, 9 or 10 ring atoms; and wherein the ring comprising R$^4$ and R$^5$ is substituted with —(CH$_2$)$_{0-6}$—Y; where Y is —CH$_2$OR$^a$, —CO$_2$R$^a$, —OC(O)R$^a$, —CH$_2$OC(O)R$^a$, —C(O)NR$^b$R$^c$, —CH$_2$SR$^a$, —C(S)OR$^a$, —OC(S)R$^a$, —CH$_2$OC(S)R$^a$ or C(S)NR$^b$R$^c$ or —CH$_2$N(R$^b$)(R$^c$);

each R$^7$ is independently hydrogen, (C$_1$-C$_8$)alkyl, (C$_3$-C$_8$)cycloalkyl, aryl or aryl(C$_1$-C$_8$)alkylene;

X is —CH$_2$OR$^a$, —CO$_2$R$^a$, —CH$_2$OC(O)R$^a$, —C(O)NR$^b$R$^c$, —CH$_2$SR$^a$, —C(S)OR$^a$, —CH$_2$OC(S)R$^a$, C(S)NR$^b$R$^c$ or —CH$_2$N(R$^b$)(R$^c$);

each R$^a$, R$^b$ and R$^c$ is independently hydrogen, (C$_1$-C$_8$)alkyl, or (C$_1$-C$_8$)alkyl substituted with 1-3 (C$_1$-C$_8$)alkoxy, (C$_3$-C$_8$)cycloalkyl, (C$_1$-C$_8$)alkylthio, amino acid, aryl, aryl(C$_1$-C$_8$)alkylene, heteroaryl, or heteroaryl(C$_1$-C$_8$)alkylene; or R$^b$ and R$^c$, together with the nitrogen to which they are attached, form a pyrrolidino, piperidino, morpholino, or thiomorpholino ring; and m is 0 to about 6; or a pharmaceutically acceptable salt thereof.

A specific value for —N(R$^7$)$_2$ is amino, monomethylamino or cyclopropylamino.

A specific value for Z is carboxy- or —(C$_1$-C$_4$)alkoxycarbonyl-cyclohexyl(C$_1$-C$_4$)alkyl.

A specific value for $R^a$ is H or $(C_1\text{-}C_4)$alkyl, i.e., methyl or ethyl.

A specific value for $R^b$ is H, methyl or phenyl.

A specific value for $R^c$ is H, methyl or phenyl.

A specific value for $-(CR^1R^2)_m-$ is $-CH_2-$ or $-CH_2-CH_2-$.

A specific value for X is $CO_2R^a$, $(C_2\text{-}C_5)$alkanoylmethyl or amido.

A specific value for Y is $CO_2R^a$, $(C_2\text{-}C_5)$alkanoylmethyl or amido.

A specific value for m is 1.

Specific compounds useful for practicing the invention are compounds JR3259, JR3269, JR4011, JR4009, JR-1085 and JR4007.

Specific $A_{2A}$ adenosine receptor agonists suitable for use with the present invention having formula (II) include those described in U.S. Pat. No. 6,232,297. Specific compounds of formula (II) are those wherein each $R^7$ is H, X is ethylaminocarbonyl and Z is 4-carboxycyclohexylmethyl (DWH-146a), Z is 4-methoxycarbonylcyclohexylmethyl (DWH-146e), Z is 4-isopropylcarbonyl-cyclohexylmethyl (AB-1), Z is 4-acetoxymethyl-cyclohexylmethyl (JMR-193) or Z is 4-pyrrolidine-1-carbonylcyclohexylmethyl (AB-3). Additional compounds useful in practicing the invention are depicted below.

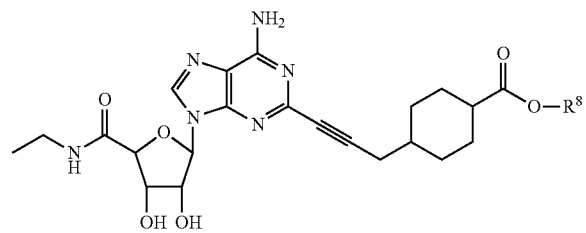

DWH-146: $R^8$ = H or Me.
AB-1: $R^8$ = iPr

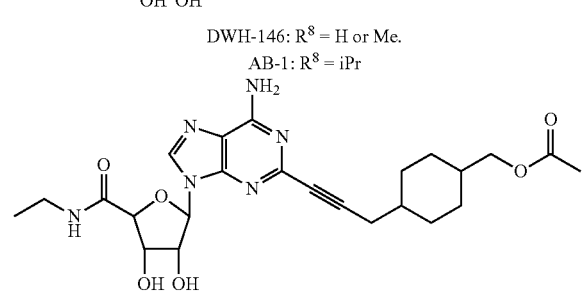

JMR-193

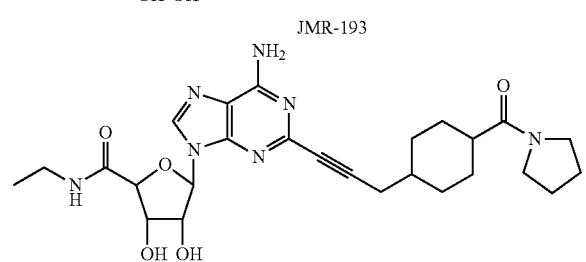

AB-3

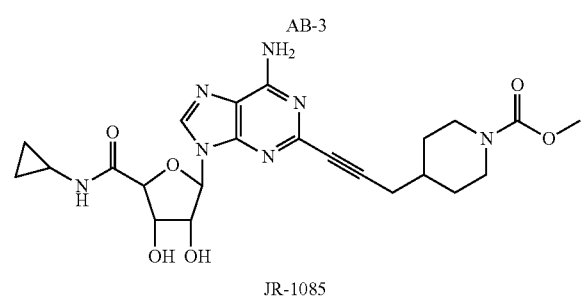

JR-1085

The specific $A_{2A}$ adenosine receptor agonists suitable for use with the present invention having formula (II) include those described in U.S. Pat. No. 6,232,297. These compounds, having formula (II), can be prepared according to the methods described therein.

Another specific group of agonists of $A_{2A}$ adenosine receptors that are useful in the practice of the present invention include compounds having the general formula (III):

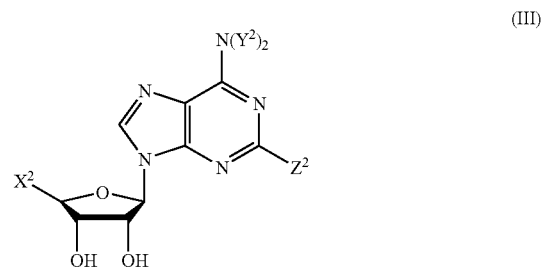

(III)

wherein $Z^2$ is a group selected from the group consisting of $-OR^{12}$, $-NR^{13}R^{14}$, a $-C\equiv C-Z^3$, and $-NH-N=R^{17}$;

each $Y^2$ is individually H, $C_1\text{-}C_6$ alkyl, $C_3\text{-}C_7$ cycloalkyl, phenyl or phenyl $C_1\text{-}C_3$ alkyl;

$R^{12}$ is $C_{1\text{-}4}$-alkyl; $C_{1\text{-}4}$-alkyl substituted with one or more $C_{1\text{-}4}$-alkoxy groups, halogens (fluorine, chlorine or bromine), hydroxy groups, amino groups, mono($C_{1\text{-}4}$-alkyl)amino groups, di($C_{1\text{-}4}$-alkyl)amino groups or $C_{6\text{-}10}$-aryl groups wherein the aryl groups may be substituted with one or more halogens (fluorine, chlorine or bromine), $C_{1\text{-}4}$-alkyl groups, hydroxy groups, amino groups, mono($C_{1\text{-}4}$-alkyl)amino groups or di($C_{1\text{-}4}$-alkyl)amino groups; or $C_{6\text{-}10}$-aryl; or $C_{6\text{-}10}$-aryl substituted with one or more halogens (fluorine, chlorine or bromine), hydroxy groups, amino groups, mono($C_{1\text{-}4}$-alkyl)amino groups, di($C_{1\text{-}4}$-alkyl)amino groups or $C_{1\text{-}4}$-alkyl groups;

one of $R^{13}$ and $R^{14}$ has the same meaning as $R^{12}$ and the other is hydrogen; and $R^{17}$ is a group having the formula (i)

(i)

wherein each of $R^{15}$ and $R^{16}$ independently may be hydrogen, $(C_3\text{-}C_7)$cycloalkyl or any of the meanings of $R^{12}$, provided that $R^{15}$ and $R^{16}$ are not both hydrogen;

$X^2$ is $CH_2OH$, $CH_3$, $CO_2R^{20}$ or $C(=O)NR^{21}R^{22}$ wherein $R^{20}$ has the same meaning as $R^{13}$ and wherein $R^{21}$ and $R^{22}$ have the same meanings as $R^{15}$ and $R^{16}$ or $R^{21}$ and $R^{22}$ are both H;

$Z^3$ has one of the following meanings:

$C_6\text{-}C_{10}$ aryl, optionally substituted with one to three halogen atoms, $C_1\text{-}C_6$ alkyl, $C_1\text{-}C_6$ haloalkyl, $C_1\text{-}C_6$ alkoxy, $C_1\text{-}C_6$ haloalkoxy, $C_2\text{-}C_6$ alkoxycarbonyl, $C_2\text{-}C_6$ alkoxyalkyl, $C_1\text{-}C_6$ alkylthio, thio, CHO, cyanomethyl, nitro, cyano, hydroxy, carboxy, $C_2\text{-}C_6$ acyl, amino $C_1\text{-}C_3$ monoalkylamino, $C_2\text{-}C_6$ dialkylamino, methylenedioxy or aminocarbonyl;

a group of formula $-(CH_2)_q$-Het wherein q is 0 or an integer from 1 to 3 and Het is 5 or 6 membered heterocyclic aromatic or non-aromatic ring, optionally benzocondensed, containing 1 to 3 heteroatoms selected from non-peroxide oxygen, nitrogen or sulphur, linked through a carbon atom or through a nitrogen atom;

$C_3$-$C_7$ cycloalkyl optionally containing unsaturation or $C_2$-$C_4$ alkenyl;

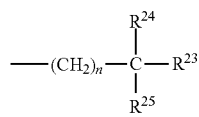 (ii)

wherein
$R^{23}$ is hydrogen, methyl or phenyl;
$R^{24}$ is hydrogen, $C_1$-$C_6$ linear or branched alkyl, $C_5$-$C_6$ cycloalkyl or $C_3$-$C_7$ cycloalkenyl, phenyl-$C_1$-$C_2$-alkyl or $R^{23}$ and $R^{24}$, taken together, form a 5 or 6-membered carbocyclic ring or $R^{25}$ is hydrogen and $R^{23}$ and $R^{24}$, taken together, form an oxo group or a corresponding acetalic derivative;
$R^{25}$ is OH, $NH_2$ dialkylamino, halogen, cyano; and n is 0 or 1 to 4; or
a) $C_1$-$C_{16}$ alkyl, optionally comprising 1-2 double bonds, O, S or $NY^2$;
or a pharmaceutically acceptable salt thereof.

Specific $C_{6-10}$-aryl groups include phenyl and naphthyl.

In one embodiment, in the compound of formula (III), $Z^2$ is a group of the formula (iii)

 (iii)

wherein n is an integer from 1-4, e.g., 2, and Ar is a phenyl group, tolyl group, naphthyl group, xylyl group or mesityl group. In one embodiment, Ar is a para-tolyl group and n=2.

In one embodiment, in the compound of formula (III), $Z^2$ is a group of the formula (iv)

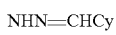 (iv)

wherein Cy is a $C_{3-7}$-cycloalkyl group, such as cyclohexyl or a $C_{1-4}$ alkyl group, such as isopropyl.

In another embodiment, in the compound of formula (III), $Z^2$ is a group of the formula (vii)

 (v)

wherein $Z^3$ is $C_3$-$C_{16}$ alkyl, hydroxy $C_2$-$C_6$ alkyl or (phenyl) (hydroxymethyl).

Specific examples of such compounds of formula (III) include those shown below:

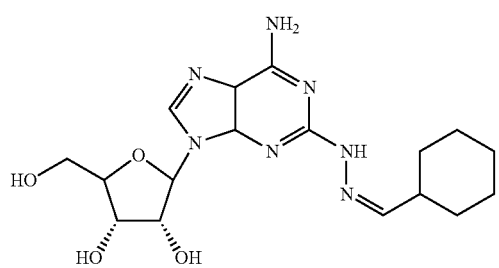

WRC-0740

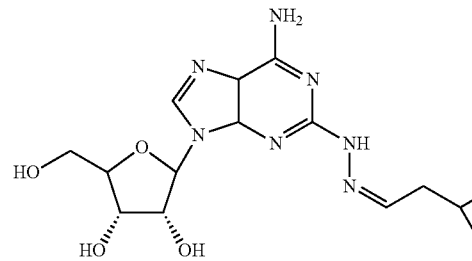

WRC-0474

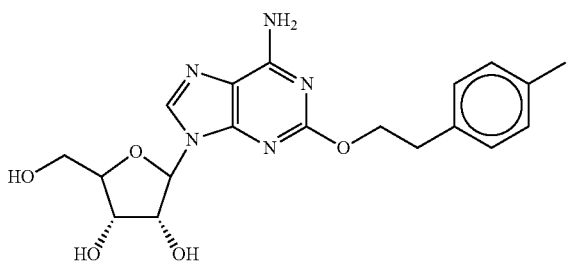

WRC-0090

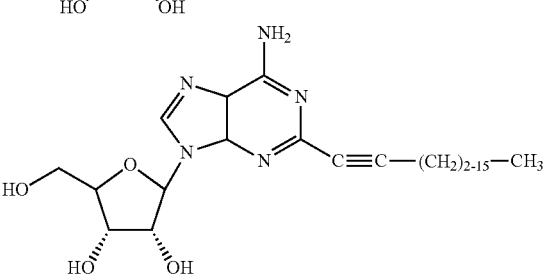

and

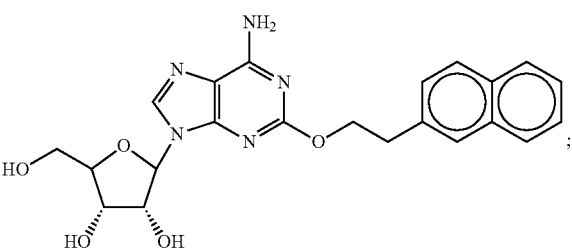

WRC-0018 wherein the H on $CH_2OH$ can optionally be replaced by ethylaminocarbonyl. Of these specific examples, WRC-0474 [SHA 211] and WRC-0470 are particularly preferred.

Such compounds may be synthesized as described in: Olsson et al. (U.S. Pat. Nos. 5,140,015 and 5,278,150); Cristalli (U.S. Pat. No. 5,593,975); Miyasaka et al. (U.S. Pat. No. 4,956,345); Hutchinson, A. J. et al., *J. Pharmacol. Exp. Ther.*, 251, 47 (1989); Olsson, R. A. et al., *J. Med. Chem.*, 29, 1683 (1986); Bridges, A. J. et al., *J. Med. Chem.*, 31, 1282 (1988); Hutchinson, A. J. et al., *J. Med. Chem.*, 33, 1919 (1990); Ukeeda, M. et al., *J. Med. Chem.*, 34, 1334 (1991); Francis, J. E. et al., *J. Med. Chem.*, 34, 2570 (1991); Yoneyama, F. et al., *Eur. J. Pharmacol.*, 213, 199-204 (1992); Peet, N. P. et al., *J. Med. Chem.*, 35, 3263 (1992); and Cristalli, G. et al., *J. Med. Chem.*, 35, 2363 (1992); all of which are incorporated herein by reference.

Another embodiment includes compounds having formula (III) where $Z^2$ is a group having formula (vi):

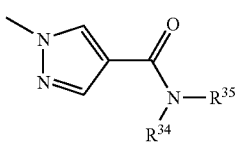

(vi)

wherein $R^{34}$ and $R^{35}$ are independently H, $C_1$-$C_6$ alkyl, $C_3$-$C_7$ cycloalkyl, phenyl, phenyl $C_1$-$C_3$ alkyl or $R^{34}$ and $R^{35}$ taken together with the nitrogen atom are a 5- or 6-membered heterocyclic ring containing 1-2 heteroatoms selected from non-peroxide oxygen, nitrogen ($N(R^{13})$) or sulphur atoms. In one embodiment, one of $R^{34}$ and $R^{35}$ is hydrogen and the other is ethyl, methyl or propyl. In another embodiment, one of $R^{34}$ and $R^{35}$ is hydrogen and the other is ethyl or methyl.

The 2-(pyrazol-1-yl)adenosine compounds of the invention, wherein $Z^2$ is a group having formula (vi), can be prepared by reacting a 2-chloro- or 2-iodo adenosine derivative with an 1H-pyrazole-4-carboxamides compound having formula (vii):

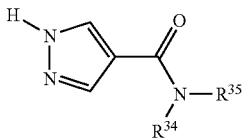

(vii)

where $R^{34}$ and $R^{35}$ are as described above, wherein selective protection/deprotection of the amido group is used as needed. A specific pyrazole derivative useful in practicing this invention is a compound having the formula:

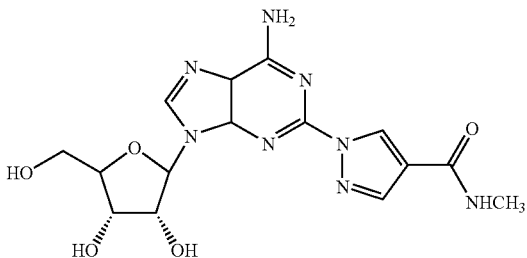

The 1H-pyrazole-4-carboxamides can be prepared starting with 1H-pyrazole-4-carboxylic acid, available from Aldrich Chemical Co. In the first step, the acid is converted to an ester, e.g., a methyl or ethyl ester. The ester is converted to the amide via aminolysis, e.g., with methylamine to form the methyl amide. The pyrazole-4-carboxamide will react with the 2-halopurines in the presence of a strong base to provide the 2-(pyrazol-1-yl)adenosine compounds having formula (III).

Another specific group of agonists of $A_{2A}$ adenosine receptors that are useful in the practice of the present invention include compounds having the general formula (IV):

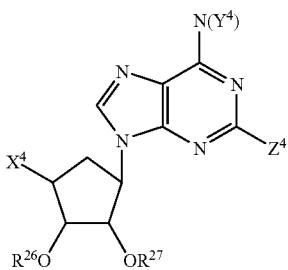

(IV)

wherein $Z^4$ is —$NR^{28}R^{29}$;

$R^{28}$ is hydrogen or ($C_1$-$C_4$) alkyl; and $R^{29}$ is a) ($C_1$-$C_4$) alkyl;

b) ($C_1$-$C_4$) alkyl substituted with one or more ($C_1$-$C_4$) alkoxy, halogen, hydroxy, amino, mono(($C_1$-$C_4$) alkyl) amino, di(($C_1$-$C_4$) alkyl)amino or ($C_6$-$C_{10}$) aryl wherein aryl is optionally substituted with one or more halogen, hydroxy, amino, ($C_1$-$C_4$)alkyl, $R^{30}$OOC—(($C_1$-$C_4$) alkyl)-, $R^{31}R^{32}$NC(=O)—(($C_1$-$C_4$)alkyl)-, mono(($C_1$-$C_4$)alkyl)amino or di(($C_1$-$C_4$)alkyl)amino;

c) ($C_6$-$C_{10}$)aryl; or d) ($C_6$-$C_{10}$)aryl substituted with one or more halogen, hydroxy, amino, mono(($C_1$-$C_4$)alkyl)amino, di(($C_1$-$C_4$) alkyl)amino or ($C_1$-$C_4$)alkyl;

wherein each $Y^4$ is individually H, ($C_1$-$C_6$)alkyl, ($C_3$-$C_7$) cycloalkyl, phenyl or phenyl($C_1$-$C_3$)alkyl; and $X^4$ is —C(=O)$NR^{31}R^{32}$, —COOR$^{30}$, or —CH$_2$OR$^{30}$;

wherein each of $R^{31}$ and $R^{32}$ are independently; hydrogen; $C_{3-7}$-cycloalkyl; ($C_1$-$C_4$)alkyl; ($C_1$-$C_4$)alkyl substituted with one or more ($C_1$-$C_4$)alkoxy, halogen, hydroxy, —COOR$^{33}$, amino, mono(($C_1$-$C_4$)alkyl)amino, di(($C_1$-$C_4$)alkyl)amino or ($C_6$-$C_{10}$)aryl wherein aryl is optionally substituted with one or more halogen, ($C_1$-$C_4$)alkyl, hydroxy, amino, mono(($C_1$-$C_4$) alkyl)amino or di(($C_1$-$C_4$) alkyl)amino; ($C_6$-$C_{10}$)aryl; or ($C_6$-$C_{10}$)aryl substituted with one or more halogen, hydroxy, amino, mono(($C_1$-$C_4$)alkyl)amino, di(($C_1$-$C_4$)alkyl)amino or ($C_1$-$C_4$)alkyl;

$R^{26}$ and $R^{27}$ independently represent hydrogen, lower alkanoyl, lower alkoxy-lower alkanoyl, aroyl, carbamoyl or mono- or di-lower alkylcarbamoyl; and $R^{30}$ and $R^{33}$ are independently hydrogen, ($C_1$-$C_4$)alkyl, ($C_6$-$C_{10}$)aryl or ($C_6$-$C_{10}$) aryl(($C_1$-$C_4$)alkyl); or a pharmaceutically acceptable salt thereof.

In one embodiment of formula (IV), at least one of $R^{28}$ and $R^{29}$ is ($C_1$-$C_4$)alkyl substituted with one or more ($C_1$-$C_4$) alkoxy, halogen, hydroxy, amino, mono(($C_1$-$C_4$)alkyl)amino, di(($C_1$-$C_4$)alkyl)amino or ($C_6$-$C_{10}$)aryl wherein aryl is optionally substituted with one or more halogen, hydroxy, amino, ($C_1$-$C_4$)alkyl, $R^{30}$OOC—($C_1$-$C_4$)alkyl, mono(($C_1$-$C_4$)alkyl)amino or di(($C_1$-$C_4$)alkyl)amino.

In another embodiment, at least one of $R^{31}$ and $R^{32}$ is $C_{1-4}$-alkyl substituted with one or more ($C_1$-$C_4$)alkoxy, halogen, hydroxy, amino, mono(($C_1$-$C_4$)alkyl)amino, di(($C_1$-$C_4$) alkyl)amino or $C_{6-10}$-aryl wherein aryl is optionally substituted with one or more halogen, hydroxy, amino, ($C_1$-$C_4$) alkyl, $R^{30}$OOC—($C_1$-$C_4$)alkylene-, mono(($C_1$-$C_4$)alkyl) amino or di(($C_1$-$C_4$)alkyl)amino.

In another embodiment, at least one of $R^{28}$ and $R^{29}$ is $C_{6-10}$-aryl substituted with one or more halogen, hydroxy, amino, mono(($C_1$-$C_4$)alkyl)amino, di(($C_1$-$C_4$)alkyl)amino or ($C_1$-$C_4$)alkyl.

In another embodiment, at least one of $R^{31}$ and $R^{32}$ is $C_{6-10}$-aryl substituted with one or more halogen, hydroxy, amino, mono(($C_1$-$C_4$)alkyl)amino, di(($C_1$-$C_4$)alkyl)amino or ($C_1$-$C_4$)alkyl.

In a specific combination, $R^{31}$ is hydrogen and $R^{32}$ is ($C_1$-$C_4$)alkyl, cyclopropyl or hydroxy-($C_2$-$C_4$)alkyl. A specific $R^{28}$ group is ($C_1$-$C_4$)alkyl substituted with ($C_6$-$C_{10}$)aryl, that is in turn substituted with $R^{30}$O(O)C—($C_1$-$C_4$)alkylene-.

A specific compound having formula (IV) is:

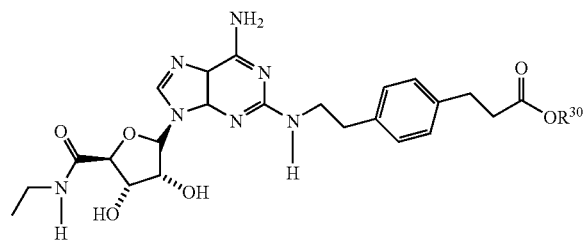

wherein $R^{30}$ is hydrogen, methyl, ethyl, n-propyl or isopropyl. One embodiment provides a compound wherein the $R^{30}$ group is methyl or ethyl. In one embodiment, the $R^{30}$ group is methyl.

Two compounds that are particularly useful in practicing the present invention have the formula:

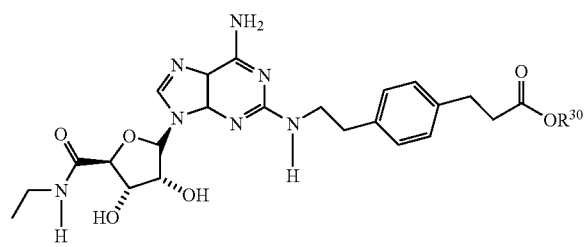

wherein $R^{30}$ is hydrogen (acid, CGS21680) and where $R^{30}$ is methyl (ester, JR2171).

The compounds of the invention having formula (IV) may be synthesized as described in: U.S. Pat. No. 4,968,697 or *J. Med. Chem.*, 33, 1919-1924, (1990).

Another agonist compound useful in the present invention is IB-MECA:

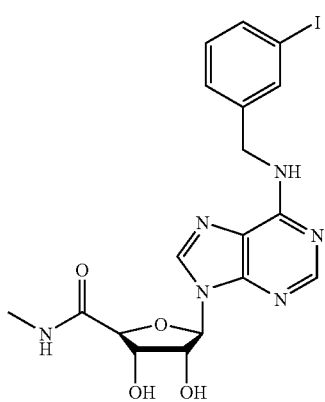

It will be appreciated by those skilled in the art that the compounds of formulas described herein, e.g., (I), (II), (III), and (IV), have more than one chiral center and may be isolated in optically active and racemic forms. In one embodiment, the riboside moiety of the compounds is derived from D-ribose, i.e., the 3',4'-hydroxyl groups are alpha to the sugar ring and the 2' and 5' groups is beta (3R, 4S, 2R, 5S). When the two groups on the cyclohexyl group are in the 1- and 4-position, they are preferably trans. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, or enzymatic techniques, by synthesis from optically-active starting materials, by chiral synthesis, or by chromatographic separation using a chiral stationary phase) and how to determine adenosine agonist activity using the tests described herein, or using other similar tests which are well known in the art.

Specifically, the invention also provides the use of a compound of formula (I) or a pharmaceutically acceptable salt thereof to prepare a medicament for treating systemic intoxification in a mammal (e.g., a human).

Specifically, the invention also provides the use of a compound of formula (I) or a pharmaceutically acceptable salt thereof to prepare a medicament for treating inflammation caused by bacterial, fungal or viral infections and the inflammation caused by the treatment of these infections, e.g., by the death of the bacterial or viral cells in a mammal (e.g., a human).

The present method also includes the administration of a Type IV phosphodiesterase (PDE) inhibitor in combination with compounds having formulae (I), (II), (III), or (IV). The combination of the compounds of the invention with type IV phosphodiesterase inhibitor provides synergistic decreases in the inflammatory response of immune cells. Examples of Type IV phosphodiesterase (PDE) inhibitors include those disclosed in U.S. Pat. No. 4,193,926, and WO 92-079778, and Molnar-Kimber, K. L. et al., *J. Immunol.*, 150, 295A (1993), all of which are incorporated herein by reference.

Suitable Type IV phosphodiesterase (PDE) inhibitors include racemic and optically active 4-(polyalkoxyphenyl)-2-pyrrolidones of general formula (VI):

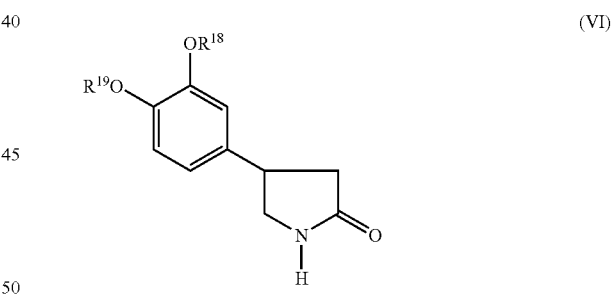

(disclosed and described in U.S. Pat. No. 4,193,926) wherein $R^{18}$ and $R^{19}$ are independently the same or different and are hydrocarbon radicals having up to 18 carbon atoms with at least one being other than methyl, a heterocyclic ring, or alkyl of 1-5 carbon atoms which is substituted by one or more of halogen atoms, hydroxy, carboxy, alkoxy, alkoxycarbonyl or an amino group or amino.

Examples of hydrocarbon $R^{18}$ and $R^{19}$ groups are saturated and unsaturated, straight-chain and branched alkyl of 1-18, e.g., 1-5, carbon atoms, cycloalkyl and cycloalkylalkyl, e.g., 3-7 carbon atoms, and aryl and aralkyl, e.g., of 6-10 carbon atoms, especially monocyclic.

Rolipram is an example of a suitable Type IV phosphodiesterase or PDE inhibitor included within the above formula. Rolipram has the following formula:

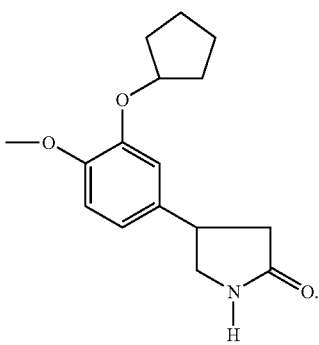

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound in combination with a suitable excipient. Such pharmaceutical compositions can be prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention can be administered parenterally (for example, by intravenous, intraperitoneal or intramuscular injection), topically, orally, or rectally.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, isotonic agents will be included, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, methods of preparation include vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing about 0.05 mg to about 500 mg, conveniently about 0.1 mg to about 250 mg, most conveniently, about 1 mg to about 150 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compositions can conveniently be administered orally, sublingually, transdermally, or parenterally at dose levels of about 0.01 to about 150 μg/kg, about 0.1 to about 50 μg/kg, and about 0.1 to about 10 μg/kg of mammal body weight.

For parenteral administration the compounds are presented in aqueous solution in a concentration of from about 0.1 to about 10%, such as about 0.1 to about 7%. The solution may contain other ingredients, such as emulsifiers, antioxidants or buffers.

The preparation of compounds useful in practicing the present invention are disclosed in U.S. patent application Ser. No. 10/236,379, filed Oct. 1, 2002, and can generally be prepared as illustrated in Schemes 1A and 1B below. Starting materials can be prepared by procedures described in these schemes, procedures described in the General methods below or by procedures that would be well known to one of ordinary skill in organic chemistry. The variables used in Schemes 1A and Scheme 1B are as defined herein or as in the claims.

The preparation of alkynyl cycloalkanols is illustrated in Scheme 1A. A solution of an appropriate cycloalkanone (where j is from 0-5) is prepared in a solvent such as THF. A solution of a suitable ethynylmagnesium halide compound in a solvent is added to the cycloalkanone. After addition, the solution is allowed to stir at about 20 C for about 20 hours. The reaction is monitored via TLC until the starting material is consumed. The reaction is quenched with water, filtered over a plug of sand and silica, washed with a solvent, such as EtOAc, and evaporated to provide the product. Typically, two products are formed, the isomers formed by the axial/equatorial addition of the alkyne (where m is as defined above, and the sum of m1 and m2 is from 0 to about 7) to the ketone. The compounds are purified via flash chromatography using EtOAc/Hexanes to provide the product.

Scheme 1A

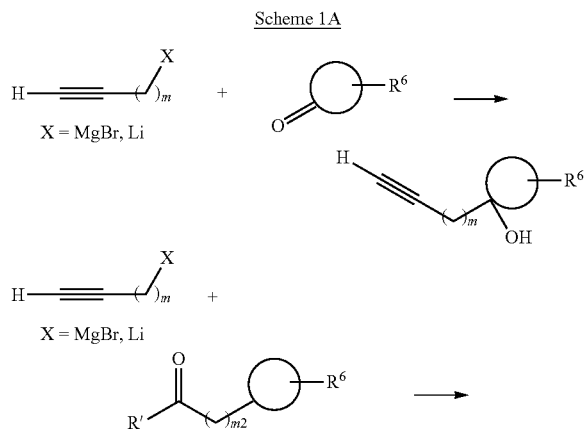

-continued

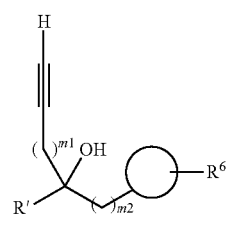

As used herein the term "treating" includes prophylaxis of the specific disorder or condition, or alleviation of the symptoms associated with a specific disorder or condition and/or preventing or eliminating said symptoms.

The preparation of 2-alkynyladenosines is illustrated in Scheme 1B. A flame-dried round bottom under nitrogen is charged with 5-(6-Amino-2-iodo-purin-9-yl)-3,4-dihydroxytetrahydrofuran-2-carboxylic acid ethylamide (NECA 2-Iodoadenosine) and a solvent such as DMF. The appropriate alkyne, wherein R is a —(CR$^1$R$^2$)$_m$ Z group, is dissolved in acetonitrile followed by TEA, 5 mole % Pd(PPh$_3$)$_4$, and CuI. All solvents are thoroughly degassed.

The solution is allowed to stir for about 24 hours at room temperature, and monitored until complete by HPLC. If the reaction is not complete after this time, additional catalyst, CuI, and TEA are added. After the reaction is complete, the solvents are removed under high-vacuum and the residue taken up in a small amount of DMF. This product is isolated using preparative silica TLC. The product is purified by RP-HPLC.

Scheme 1B

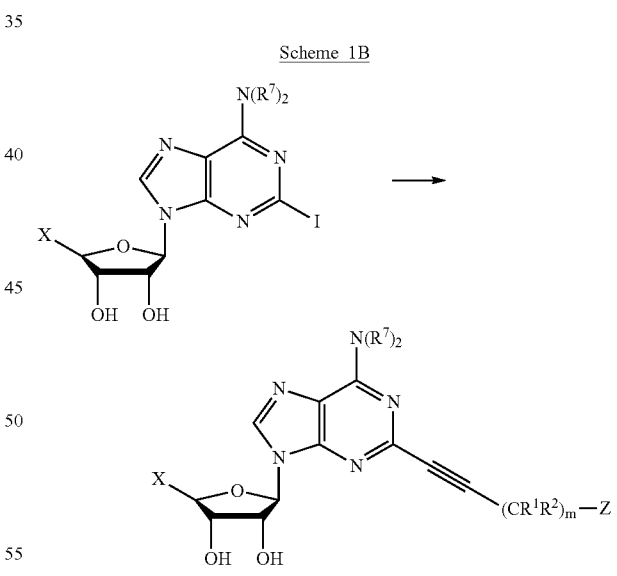

The following abbreviations have been used herein:

| | |
|---|---|
| 2-Aas | 2-alkynyladenosines; |
| $^{125}$I-ABA | N$^6$-(4-amino-3-$^{125}$iodo-benzyl)adenosine |
| APCI | Atmospheric pressure chemical ionization |
| ATL146e | 4-{3-[6-Amino-9-(5-ethylcarbamoyl-3,4-dihydroxy-tetrahydro-furan-2-yl)-9H-purin-2-yl]-prop-2-ynyl}cyclohexanecarboxylic acid methyl ester; |
| CCPA | 2-chloro-N$^6$-cyclopentyladenosine; |

-continued

| | |
|---|---|
| CGS21680 | 2-[4-(2-carboxyethyl)phenethylamino]-5'-N-ethyl-carboxamidoadenosine; |
| Cl-IB-MECA | $N^6$-3-iodo-2-chlorobenzyladenosine-5'-N-methyl-uronamide; |
| CPA | $N^6$-cyclopentyladenosine |
| DMF | dimethylformamide |
| DMSO | dimethylsulfoxide |
| DMSO-$d_6$ | deuterated dimethylsulfoxide |
| EtOAc | ethyl acetate |
| eq | equivalent |
| GPCR | G protein coupled receptor; $hA_{2A}AR$, Recombinant human $A_{2A}$ adenosine receptor; |
| IADO | 2-Iodoadenosine |
| $^{125}$I-APE, | 2-[2-(4-amino-3-[$^{125}$I]iodophenyl)ethylamino]-adenosine; |
| NECA | 5'-N-ethylcarboxamidoadenosine; |
| IB-MECA | $N^6$-3-iodobenzyladenosine-5'-N-methyluronamide; |
| 2-Iodoadenosine | 5-(6-amino-2-iodo-purin-9-yl)-3,4-dihydroxytetra-hydro-furan-2-carboxylic ethylamide |
| HPLC | high-performance liquid chromatography |
| HRMS | high-resolution mass spectrometry |
| $^{125}$I-ZM241385, | $^{125}$I-4-(2-[7-amino-2-[2-furyl][1,2,4]triazolo[2,3-a]-[1,3,5]triazin-5-yl-amino]ethyl)phenol; |
| INECA | 2-iodo-N-ethylcarboxamidoadenosine |
| LC/MS | liquid chromatography/mass spectrometry |
| m.p. | melting point |
| MHz | megahertz |
| MRS 1220, | N-(9-chloro-2-furan-2-yl-[1,2,4]triazolo[1,5-c]-quinazolin-5-yl)-2-phenylacetamide; |
| MS | mass spectrometry |
| NECA | N-ethylcarboxamidoadenosine |
| NMR | nuclear magnetic resonance |
| RP-HPLC | reverse phase high-performance liquid chromatography |
| TBAF | tetrabutylammonium fluoride |
| TBS | tert-butyldimethylsilyl |
| TBDMSCl | tert-butyldimethylsilylchloride |
| TEA | triethylamine |
| TFA | trifluoroacetic acid |
| THF | tetrahydrofuran |
| TLC | thin layer chromatography |
| p-TSOH | para-toluenesulfonic acid |
| XAC | 8-(4-((2-a-minoethyl)aminocarbonyl-methyloxy)-phenyl)-1-3-dipropylxanthine. |

The invention will now be illustrated using the following non-limiting examples.

EXAMPLES

Animals

Several genetic models of SCD have been developed in mice. NY-Sickle mice (NY-S or NY1DD) originally described by Fabry were used. The NY-S mouse is homozygous for a deletion of the murine βmajor-globin gene and expresses the human βS and human α2 globin genes (βHβS [βMDD]). Over 70% of all β-globins expressed in this mouse are expressed as human βS. The NY-S (NY1DD) mouse has been back-crossed onto the C57BL/6 strain and C57BL/6 mice are used as experimental controls.

Cytokine Measurements

NY-S (NY1DD) mice exhibited an elevated inflammatory state relative to C57BL/6 control mice. The serum levels of the pro-inflammatory cytokines IL-6 an KC are elevated at baseline in the NY-S (NY1DD) mice (FIG. 1), as are TNF-α, the hematopoietic growth factor G-CSF and the acute phase reactant serum amyloid P-component (not shown).

Hypoxia/reperfusion injury is a general manifestation of SCD. Since hypoxia is reported to induce an inflammatory response in NY-S (NY1DD) mice, hypoxia in mice was used as a surrogate for sickle cell crisis in man. The effect of hypoxic stress on serum cytokine levels in Compound No. 2 of Table A above and vehicle-treated NY-S (NY1DD) mice was investigated. Compound No. 2 of Table A above is an $A_2A$-selective agonist with a longer half-life than ATL146e. FIG. 2 shows a rise serum IL-6 levels in NY-S (NY1DD) mice in response to hypoxia/reoxygenation injury. NY-S (NY1DD) mice (n=3) were subjected to 3 hours hypoxia (10% $O_2$) followed by 4 hours reoxygenation in ambient air. At the end of the hypoxic period, the animals received either vehicle or Number 2 of Table A above (5 µg/kg), by intraperitoneal bolus. During the reperfusion period mice received additional hourly injections of Number 2 of Table A above (1 µg/kg). At the end of the reperfusion period blood was drawn by the retro-orbital route and serum was prepared using Microtainer™ brand serum separators (Becton Dickinson, Franklin Lakes, N.J.). Serum IL-6 levels were assayed by ELISA (eBioscience, San Diego, Calif.). As compared to baseline, there is a large elevation of IL-6 in response to hypoxia/reoxygenation injury in vehicle-treated NY-S (NY1DD) mice. Most of the increase is abolished in mice receiving Number 2 of Table A above after hypoxia. This is an important experiment because it establishes that an A2A agonist can reverse cytokine elevation when it is administered after stress (hypoxia). This is clinically important because most patients seek medical attention after the initiation of sickle cell crisis.

Intravital Microscopy

An exteriorized cremaster muscle preparation was used to study the microcirculation in vivo as a means of assaying the effect of the test compounds, e.g., ATL146e, on leukocyte interactions with the endothelium. FIG. 3 shows the effect of ATL146e on leukocyte adhesion. In this experiment, mice were not stressed with hypoxia, but the manipulation of the cremaster tissue for microscopic examination itself produces some rolling and adherence of leukocytes, probably due to release of chemokines from damaged tissue. Adherent leukocytes were defined as those which moved less than one circumference in an observational period (30 seconds/vessel). At baseline, NY-S (NY1DD) mice have more than three times the number of adherent leukocytes/field when compared to C57BL/6 mice. In two groups of NY-S (NY1DD) mice, ATL146e was administered by either infusion (Alzet minipump, 10 ng/kg/min, overnight) or by bolus injection (intraperitoneal, 5 µg/kg, 30 minutes prior to cremaster exteriorization). Treatment with ATL146e causes a pronounced reduction in leukocyte adhesion when administered by either route. It is notable that the dose of ATL146e used for infusion is well below the dose that elicits cardiovascular effects, hypotension and reflex tachycardia. These results illustrate that the anti-inflammatory therapy will reduce the severity of vaso-occlusive crises and that ATL146e has beneficial effects on microvascular flow.

Endothelial Adhesions Adhesion Assays

Adhesion of both sickle RBCs and leukocytes in SCD is believed dependent on endothelial activation. Patients with SCD have increased numbers of circulating endothelial cells, revealing an abnormally activated phenotype. Murine aortic endothelial cells (MAECs) were prepared from C57BL/6 and NY-S (NY1DD) mice. In a static adhesion assay using WEHI monocytes activation of the endothelium as manifested by increasing monocyte adhesion can be quantified. MAECs prepared from C57BL/6 mice form a monolayer which is not highly activated as assessed by the small number of adherent monocytes. As a positive control for endothelial activation C57BL/6 MAECs were stimulated with murine TNFα (10 U/ml). When stimulated with TNFα there is a three-fold increase in the number of monocytes captured indicating endothelial activation by TNFα MAEC monolayers prepared from NY-S (NY1DD) mice mediate greatly increased monocyte adhesion (six-fold relative to control). Clearly, the endothelium of NY-S (NY1DD) sickle mice is in a state of activation at baseline.

Platelet Activation

Adenosine 5'-diphosphate (ADP) is a critical mediator of platelet activation. Two members of the $P_2Y$-receptor family ($P_2Y_1$, $P_2Y_{12}$) are responsible for the initiation and amplification of the aggregation response. FIG. 5 shows aggregation, measured as singlet loss (reduction in the number of single platelets), in platelet-rich plasma prepared from the blood of wild type and NY-S (NY1DD) mice in response to activation by increasing concentrations of ADP (0-10 µM). We have discovered that even at baseline (shear stress only), platelets isolated from NY-S (NY1DD) mice exhibit significantly increased aggregation as compared to control platelets (FIGS. 5A & 5B—lowest line on graph). Platelets from NY-S (NY1DD) mice consistently demonstrate increased sensitivity to activation by ADP and show hyper-responsiveness to sub-maximal doses of ADP (FIG. 5B). When NY-S (NY1DD) mice were pretreated in vivo with ATL146e (Alzet mini-pump, 10 ng/kg/min, O/N) platelet activation in platelet rich plasma prepared from these animals (at all doses of ADP added in vitro) was reduced to below control levels (FIG. 5C).

Pulmonary Histology

FIG. 6 shows representative sections from hematoxylin- and eosin-stained (H&E), inflation-fixed lung tissue from C57BL/6 and NY-S (NY1DD) mice. Under normoxic conditions, while the lungs of the wild type mice are clear, there is a high incidence of focal vascular congestion in the NY-S (NY1DD) mice (FIGS. 6A & 6B, see arrows). The disseminated pink color throughout the section may be due to elevated numbers of possibly adherent capillary red cells. The extent of vascular congestion is exacerbated in the NY-S (NY1DD) mice following 3 hour of hypoxia (10% $O_2$; FIG. 6c). The increased susceptibility of the NY-S (NY1DD) mice to hypoxia-induced lung injury is evidenced both as an increase in the total area of involvement and the size of the vessels congested (see arrow, FIG. 6C). Finally, the severity of the hypoxia-induced vascular congestion in the NY-S (NY1DD) mice is significantly reduced by treatment with ATL146e initiated in this experiment prior to hypoxic stress (Alzet mini-pump, 10 ng/kg/min, O/N) (FIG. 6D).

Pulmonary Hypoxia

BRU59-21 (Oxo[[3,3,9,9-tetramethyl-5-oxa-6-(2-nitro-1H-imidazol-1-yl)-4,8-diazaundecane-2,10-dione dioximato] (3-)-N,N',N'',N''']-technetium), is a 99mTc-labeled tracer which shows selective accumulation in hypoxic cells (<40 ppm $O_2$). Animals were subject to 3 hours hypoxia (10% $O_2$)/1 hour reoxygenation. After 30 minutes of reoxygenation the mice were given a bolus intra-jugular injection of BRU59-21 (~300 µCi). At the end of the reoxygenation period planar gamma camera images were taken with a ten minute acquisition window. The images in FIG. 7 show tracer accumulation in the tissues of hypoxic C57BL/6 and NY-S (NY1DD) mice. FIG. 7A shows color-enhanced images of tracer distribution in a C57/B6 and NY-S mouse (orientation is head-down). There is a large non-specific signal present in the abdomen due to hepatic metabolism and clearance of the tracer via the intestinal tract. Anterior to the abdominal signal is a bilateral signal which is absent from the C57/B6 mice and localized to the lungs in the NY-S (NY1DD) mouse. FIG. 7B shows three untreated NY-S (NY1DD) mice (animals 1-3) and 2 ATL146e-treated NY-S (NY1DD) mice (Alzet mini-pump, 10 ng/kg/min, O/N; animals 4-5). Qualitative examination of the signal intensity in the thoracic cavity (see boxed area) indicates the presence of significantly more lung-specific signal in the untreated mice relative to those mice which were treated with ATL146e.

FIG. 8 shows sections from C57BL/6 and NY-S (NY1DD) lungs stained with the 2-nitroimidazole, pimonidazole hydrochloride (Hypoxyprobe™-1, Chemicon International). The test compound is also a hypoxia-sensitive nitroimidazole which precipitates in cells with a $pO_2$ of <10 mmHg. C57BL/6 and NY-S (NY1DD) mice were exposed to a total of 4 hours of hypoxic air (8% $O_2$). After 3 hours the mice were removed from the chamber and given an intraperitoneal injection of Hypoxyprobe-1 (60 mg/kg) and then returned to the chamber for the remainder of the protocol. Immediately upon removal from the hypoxia chamber, lungs from each animal were removed and fixed in paraformaldehyde. Samples were paraffin-embedded, sectioned, and mounted and peroxidase immunohistochemistry was performed according to manufacturer's instructions. While the lung of the C57BL/6 control mouse is clear, there is significant peroxidase staining in the lung tissue of the NY-S (NY1DD) mouse. The staining is most intense in association with the endothelium of the blood vessels (A), but also present in association with the epithelia of some larger airways (B) and alveolar airspaces (C).

Plethysmography

Clinicians have disclosed that breathing disorders can occur in SCD patients during vaso-occlusive crisis (VOC). Patients with VOC and associated chest pain exhibit shallow, rapid breathing patterns as compared to patients with pain elsewhere. Pain-associated shallow breathing during sickle crisis may contribute to the pathogenesis of acute chest syndrome. To characterize the extent of hypoxia-induced lung injury in NY-S (NY1DD) mice, pulmonary function was assessed using unrestrained whole-body plethysmography during and after exposure to hypoxic air. Naïve NY-S (NY1DD) mice were compared to NY-S (NY1DD) mice which had been treated with ATL146e (Alzet pump, 10 ng/kg/min, overnight). During a 3 hour hypoxic stress (8% $O_2$) breathing frequency is significantly reduced in ATL146e-treated mice (FIG. 9, n=2 each group). Minute volume, defined as the total volume breathed during one minute, was computed on a breath by breath basis and suggests that the respiratory stress of hypoxia was alleviated by treatment with ATL146e.

Detailed Methods:

Cytokine Levels

Blood was drawn by the retro-orbital route and serum was prepared using Microtainer™ brand serum separators (Becton Dickinson, Franklin Lakes, N.J.). The serum was aliquoted and stored at −80° C. until assay. Serum cytokine levels are assayed using either of two methodologies. For broad-based cytokine screening we use the Bio-Plex Suspension Array System (Bio-Rad Laboratories, Inc., Hercules, Calif.) which allows multi-analyte detection with a broad dynamic range. Up to 18 cytokines can be assayed simultaneously in a 15 µl serum sample. For focused cytokine screening, or for cytokines not available in Bio-Plex format, we use Ready-SET-Go! ELISA-set reagents (eBioscience, San Diego, Calif.). All assays are run according to the manufacturer's protocols.

Intravital Microscopy

Mice were anesthetized with an intraperitoneal injection of ketamine (125 mg/kg; Sanofi Winthrop Pharmaceuticals, New York, N.Y.), xylazine (12.5 mg/kg; Phoenix Scientific, St. Joseph, Mo.) and atropine sulfate (0.025 mg/kg; Fujisawa, Deerfield, Ill.), and placed on a 38° C. heating pad. The trachea was intubated using polyethylene (PE) 90 tubing (ID 0.86 m, OD 1.27 mm; Becton Dickinson, Sparks, Md.). The left carotid artery was cannulated using PE10 tubing (ID 0.28 mm, OD 0.61 mm). The cremaster was exteriorized, pinned to the stage, and superfused with thermocontrolled bicarbonate-buffered saline (131.9 mM NaCl, 18 mM NaHCO$_3$, 4.7 mM KCl, 2.0 mM CaCl$_2$.2H$_2$O, and 1.2 mM MgCl$_2$) equilibrated with 5% CO$_2$ in N$_2$.

Microscopic observations were made on a Zeiss intravital microscope (Axioskop, Carl Zeiss, Inc., Thornwood, N.Y.) with a saline immersion objective (SW 40/0.75) visualized under bright field illumination. Recordings were made through a CCD camera (model VE-1000CD, Dage-MTI, Michigan City, Ind.) on a Panasonic S-VHS recorder. Randomly selected venules with diameters between 19 and 54 μm were recorded for 1.5 minutes.

A MicroMotion DC30 video compression card (Pinnacle Systems, Mountain View, Calif.) was used to digitize video recordings from a JVC HR-53600U VHS recorder into a Macintosh computer (Adobe Premiere software). Digitized video clips were analyzed with the public domain NIH image program with custom-written macros. Adherent cells were defined as leukocytes that did not move for at least 30 seconds. Data are presented as mean±SEM. Individual comparisons between groups were calculated using a one-tailed t test with p<0.05.

Platelet Function Studies:

Mice were first anesthetized with the use of a vaporizer (Vapomatic, A.M. Bickford, INC., Wales Center, N.Y.) delivering 1.5% isoflurane (Abbott Laboratories, Chicago, Ill.). The animals were ventilated with 100% oxygen (tidal volume 0.3 mL; rate 125 breaths/min; respiratory/expiratory ratio 1; positive end-expiratory pressure (PEEP) was between 5 and 10 cm H$_2$O) at a low rate of 0.8 L/min via an animal ventilator (Columbus Instruments, Columbus, Ohio). The depth of anesthesia was comparable as determined by the pedal withdrawal reflex.

Platelet isolation. Blood samples were then obtained by retro-orbital blood collection and anticoagulated with phosphate buffer saline (PBS) lacking calcium and magnesium (BioWhittaker), heparin (1000 Units/mL) from porcine intestinal mucosa (Upjohn), and acid-citrate-dextrose buffer (120 mM sodium citrate, 110 mM glucose, 80 mM citric acid) in the proportion PBS:heparin:ACD=15 μL:20 μL:50 μL per 1 mL of blood. Platelet rich plasma (PRP) was then prepared from the anticoagulated whole blood by four short centrifugations (180 G for 3 min each).

Platelet aggregation assay—single particle counting. To test platelet reactivity in vitro, PRP was pre-incubated at 37° C. for 10 minutes and then stirred for 5, 10, 15, 20, and 30 seconds at 37° C., with saline or different concentrations of ADP (10 μM-0.6 μM) using a thermomixer-R (Eppendorf, Westbury, N.Y.), under orbital shaking conditions (1,200 rpm) to reproduce in vitro low-shear stress. A rotational rate and the use of 50 μL total reaction volume induced shear stress of 1 to 5 dyn/cm$^2$. The reaction was quenched with glutaraldehyde (1%), and platelet aggregation then evaluated by the loss of platelet singlets, using a resistive-particle counter. The loss of platelet singlets was expressed as a percent value of the control platelet count (platelet count in PRP incubated for 10 minutes in 37° C. in the absence of shear forces).

Optical aggregometry—In a Chronolog aggregometer, platelet suspensions (250 μl) are stirred at 1200 rpm with disposable Teflon coated magnets (6 mm length×1 mm diameter) in siliconized glass cuvettes (0.624 cm diameter) at 37±0.3° C. in a "single channel aggregation module". PRP and test compounds are mixed. An infra-red light is simultaneously passed through both the PPP and containing platelets PRP. Photo sensitive diodes detect the light transmission through PRP as well as PPP. The instrument develops a voltage proportional to the light transmittance through PRP and it is recorded as a function of time utilizing the software AGGRO/LINK for Windows v. 4.75.

Gamma Camera Imaging

C57BL/6 and NY-S (NY1DD) mice were subject to 3 hour hypoxia/1 hour reperfusion (10% O$_2$). Thirty minutes after the start of the reperfusion period the mice were anesthetized (ketamine 125 mg/kg; xylazine 12.5 mg/kg, IP) and given a bolus intra jugular injection of BRU59-21 (~300 μCi). At the end of the reperfusion period planar gamma camera images were collected. Anesthetized mice were imaged side-by-side in planar mode directly on the inverted face of a low energy, high resolution (LEHR) collimator mounted on a Siemens Orbiter gamma camera (Siemens Medical Solutions USA, Inc., Malvern Pa.). The images were acquired for 10 minutes using a 15% window centered on the 140 keV Tc99m photopeak and a 128×128 pixel image count matrix.

Plethysmography:

Plexiglas chambers (4 in diameter) are connected to a direct airflow sensor (Buxco Max II, Buxco Electronics). Constant airflow through the chambers is maintained at 70 ml/min. The flow signals are amplified by a channel amplifier (EMKA Technologies), converted to a digital signal, and recorded using IOX software (EMKA Technologies). The respiratory parameters minute ventilation (MV, ml/min), respiratory frequency (f, breaths/min), expiratory time (TE, msec), and relaxation time (RT, msec) are calculated and plotted as change over time. The chambers are calibrated by injecting 1 ml of air. The mice are placed unrestrained into the chambers and after a 30 min adjustment period, respiratory activity is recorded while the animal breathes either ambient air or hypoxic gas (8% O$_2$).

Monocyte Adhesion Assays:

Aortic endothelial cells from C57BL/6J and NY-S (NY1DD) mice were harvested from the aorta under sterile conditions. A monocyte adhesion assay that utilizes primary MAECs and WEHI78/24 cells were performed according to Hatley et al. WEHI cells are labeled with calcein-AM using standard methods described by the manufacturer (Molecular Probes). For the adhesion assay, MAECs were cultured to confluency in a 48-well plate and incubated with 35,000 calcein-labeled WEHI cells/well for 30 min at 37° C. Non-adherent cells were rinsed, and adherent cells were fixed with 1% glutaraldehyde. The number of adherent monocytes within a 10×10 eyepiece grid at 40× magnification was counted using an epifluorescence microscopy. As a positive control for monocyte adhesion, MAECs were incubated with 10 units/ml recombinant murine TNFα (R&D Systems #410-MT) for 4 hours.

All cited publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method to treat an acute inflammatory event in a subject with sickle cell disease consisting essentially of administering to a subject in need thereof an effective amount of an $A_{2A}$ adenosine receptor agonist, wherein the $A_{2A}$ adenosine receptor agonist is a compound having formula (I):

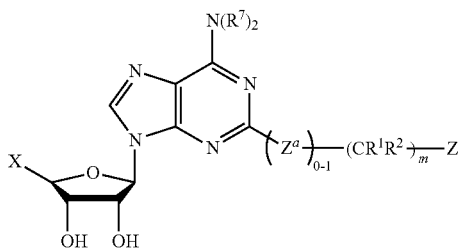

wherein $Z^a$ is C≡C, O, NH, or NHN=CR$^{3a}$;

Z is CR$^3$R$^4$R$^5$ or NR$^4$R$^5$;

each R$^1$ is independently hydrogen, halo, —OR$^a$, —SR$^a$, (C$_1$-C$_8$)alkyl, cyano, nitro, trifluoromethyl, trifluoromethoxy, (C$_3$-C$_8$)cycloalkyl, heterocycle, heterocycle (C$_1$-C$_8$)alkylene-, aryl, aryl(C$_1$-C$_8$)alkylene-, heteroaryl, heteroaryl(C$_1$-C$_8$)alkylene-, —CO$_2$R$^a$, R$^a$C(=O)O—, R$^a$C(=O)—, —OCO$_2$R$^a$, R$^b$R$^c$NC(=O)O—, R$^a$OC(=O)N(R$^b$)—, R$^b$R$^c$N—, R$^b$R$^c$NC(=O)—, R$^a$C(=O)N(R$^b$)—, R$^b$R$^c$NC(=O)N(R$^b$)—, R$^b$R$^c$NC(=S)N(R$^b$)—, R$^a$OC(=S)—, R$^a$C(=S)—, —SSR$^a$, R$^a$S(=O)—, R$^a$S(=O)$_2$—, or —N=NR$^b$;

each R$^2$ is independently hydrogen, halo, (C$_1$-C$_8$)alkyl, (C$_3$-C$_8$)cycloalkyl, heterocycle, heterocycle(C$_1$-C$_8$) alkylene-, aryl, aryl(C$_1$-C$_8$)alkylene-, heteroaryl, or heteroaryl(C$_1$-C$_8$)alkylene-; or R$^1$ and R$^2$ and the atom to which they are attached is C=O, C=S or C=NR$^d$;

R$^4$ and R$^5$ are independently H or (C$_1$-C$_8$)alkyl; or

R$^4$ and R$^5$ together with the atom to which they are attached form a saturated, partially unsaturated, or aromatic ring that is mono-, bi-, or polycyclic having 3, 4, 5, 6, 7, 8, 9 or 10 ring atoms optionally having 1, 2, 3, or 4 heteroatoms selected from non-peroxide oxy (—O—), thio (—S—), sulfinyl (—SO—), sulfonyl (—S(O)$_2$—) or amine in the ring;

wherein R$^4$ and R$^5$ are independently substituted with 0-3 R$^6$ groups or any ring comprising R$^4$ and R$^5$ is substituted with from 0 to 14 R$^6$ groups; wherein each R$^6$ is independently hydrogen, halo, —OR$^a$, —SR$^a$, (C$_1$-C$_8$) alkyl, cyano, nitro, trifluoromethyl, trifluoromethoxy, (C$_3$-C$_8$)cycloalkyl, (C$_6$-C$_{12}$)bicycloalkyl, heterocycle, heterocycle (C$_1$-C$_8$)alkylene-, aryl, aryl (C$_1$-C$_8$)alkylene-, heteroaryl, heteroaryl(C$_1$-C$_8$)alkylene-, —CO$_2$R$^a$, R$^a$C(=O)O—, R$^a$C(=O)—, —OCO$_2$R$^a$, R$^b$R$^c$NC(=O)O—, R$^a$OC(=O)N(R$^b$)—, R$^b$R$^c$N—, R$^b$R$^c$NC(=O)—, R$^a$C(=O)N(R$^b$)—, R$^b$R$^c$NC(=O)N (R$^b$)—, R$^b$R$^c$NC(=S)N(R$^b$)—, R$^a$OC(=S)—, R$^a$C(=S)—, —SSR$^a$, R$^a$S(=O)—, —NNR$^b$, or two R$^6$ groups and the atom to which they are attached is C=O, C=S; or two R$^6$ groups together with the atom or atoms to which they are attached can form a carbocyclic or heterocyclic ring comprising from 1-6 atoms and optionally comprising 1, 2, 3, or 4 heteroatoms selected from non-peroxide oxy (—O—), thio (—S—), sulfinyl (—SO—), sulfonyl (—S(O)$_2$—) or amine in the ring;

R$^3$ is hydrogen, halo, —OR$^a$, —SR$^a$, (C$_1$-C$_8$)alkyl, cyano, nitro, trifluoromethyl, trifluoromethoxy, (C$_3$-C$_8$)cycloalkyl, heterocycle, heterocycle(C$_1$-C$_8$)alkylene-, aryl, aryl(C$_1$-C$_8$)alkylene-, heteroaryl, heteroaryl(C$_1$-C$_8$)alkylene-, —CO$_2$R$^a$, R$^a$C(=O)O—, R$^a$C(=O)—, —OCO$_2$R$^a$, R$^b$R$^c$NC(=O)O—, R$^a$OC(=O)N(R$^b$)—, R$^b$R$^c$N—, R$^b$R$^c$NC(=O)—, R$^a$C(=O)N(R$^b$)—, R$^b$R$^c$NC(=O)N(R$^b$)—, R$^b$R$^c$NC(=S)N(R$^b$)—, R$^a$OC(=S)—, R$^a$C(=S)—, —SSR$^a$, R$^a$S(=O)—, R$^a$S(=O)$_2$—, or —NNR$^b$; or if the ring formed from CR$^4$R$^5$ is aryl or heteroaryl or partially unsaturated then R$^3$ can be absent;

R$^{3a}$ is hydrogen, (C$_1$-C$_8$)alkyl or aryl;

each R$^7$ is independently hydrogen, (C$_1$-C$_8$)alkyl, (C$_3$-C$_8$) cycloalkyl, aryl, aryl(C$_1$-C$_8$)alkylene, heteroaryl, or heteroaryl(C$_1$-C$_8$)alkylene-;

X is —CH$_2$OR$^a$, —CO$_2$R$^a$, —CH$_2$OC(O)R$^a$, —C(O) NR$^b$R$^c$, —CH$_2$SR$^a$, —C(S)OR$^a$, —CH$_2$OC(S)R$^a$, —C(S)NR$^b$R$^c$, or —CH$_2$N(R$^b$)(R$^c$); or

X is an aromatic ring of the formula:

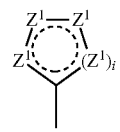

each Z$^1$ is non-peroxide oxy (—O—), S(O)$_{0-2}$, —C(R$^8$)—, or amine (—NR$^8$—), provided that at least one Z$^1$ is non-peroxide oxy (—O—), thio (—S—), sulfinyl (—SO—), sulfonyl (—S(O)$_2$—) or amine (—NR$^8$—);

each R$^8$ is independently hydrogen, (C$_1$-C$_8$)alkyl, (C$_1$-C$_8$) alkenyl, (C$_3$-C$_8$)cycloalkyl, (C$_3$-C$_8$)cycloalkyl(C$_1$-C$_8$) alkylene, (C$_3$-C$_8$)cycloalkenyl, (C$_3$-C$_8$)cycloalkenyl (C$_1$-C$_8$)alkylene, aryl, aryl(C$_1$-C$_8$)alkylene, heteroaryl, or heteroaryl(C$_1$-C$_8$)alkylene, wherein any of the alkyl or alkenyl groups of R$^8$ are optionally interrupted by —O—, —S—, or —N(R$^a$)—;

wherein any of the alkyl, cycloalkyl, heterocycle, aryl, or heteroaryl, groups of R$^1$, R$^2$, R$^3$, R$^{3a}$, R$^6$, R$^7$ and R$^8$ is optionally substituted on carbon with one or more substituents selected from the group consisting of halo, —OR$^a$, —SR$^a$, (C$_1$-C$_8$)alkyl, cyano, nitro, trifluoromethyl, trifluoromethoxy, (C$_3$-C$_8$)cycloalkyl, (C$_6$-C$_{12}$)bicycloalkyl, heterocycle, heterocycle(C$_1$-C$_8$)alkylene-, aryl, aryloxy, aryl (C$_1$-C$_8$)alkylene-, heteroaryl, heteroaryl(C$_1$-C$_8$)alkylene-, —CO$_2$R$^a$, R$^a$C(=O)O—, R$^a$C(=O)—, —OCO$_2$R$^a$, R$^b$R$^c$NC(=O)O—, R$^a$OC (=O)N(R$^b$)—, R$^b$R$^c$N—, R$^b$R$^c$NC(=O)—, R$^a$C(=O) N(R$^b$)—, R$^b$R$^c$NC(=O)N(R$^b$)—, R$^b$R$^c$NC(=S)N (R$^b$)—, R$^a$OC(=S)—, R$^a$C(=S)—, —SSR$^a$, R$^a$S (=O)$_p$—, R$^b$R$^c$NS(O)$_p$—, and —N=NR$^b$;

wherein any (C$_1$-C$_8$)alkyl, (C$_3$-C$_8$)cycloalkyl, (C$_6$-C$_{12}$)bicycloalkyl, (C$_1$-C$_8$)alkoxy, (C$_1$-C$_8$)alkanoyl, (C$_1$-C$_8$) alkylene, or heterocycle, is optionally partially unsaturated;

each R$^a$, is independently hydrogen, (C$_1$-C$_{12}$)alkyl, (C$_1$-C$_8$)alkoxy-(C$_1$-C$_8$)alkyl-, (C$_1$-C$_8$)alkylthio-(C$_1$-C$_8$) alkyl-, or amino acid, each R$^b$, and R$^c$ is independently hydrogen, (C$_1$-C$_{12}$)alkyl, (C$_1$-C$_8$)alkoxy-(C$_1$-C$_8$)alkyl-, (C$_3$-C$_8$)cycloalkyl, (C$_1$-C$_8$)alkylthio-(C$_1$-C$_8$)alkyl or amino acid, alternatively R$^b$ and R$^c$, together with the nitrogen to which they are attached, form a pyrrolidino, piperidino, morpholino, or thiomorpholino ring;

R$^d$ is hydrogen or (C$_1$-C$_6$)alkyl;

i is 1 or 2 m is 0 to 8 and p is 0 to 2;

provided that m is at least 1 when Z is NR$^4$R$^5$; or a pharmaceutically acceptable salt thereof, so as to treat an acute inflammatory event in a subject with sickle cell disease.

2. The method of claim 1, wherein the compound is of formula (Ia):

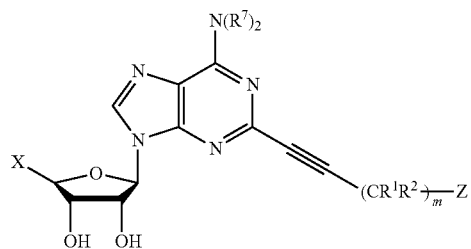

(Ia)

R¹ is hydrogen, —OH, —CH₂OH, —OMe, —OAc, —NH₂, —NHMe, —NMe₂ or —NHAc;
R² is hydrogen, (C₁-C₈)alkyl, cyclopropyl, cyclohexyl or benzyl;
R³ is hydrogen, OH, OMe, OAc, NH₂, NHMe, NMe₂ or NHAc;
CR⁴R⁵ or NR⁴R⁵ is optionally substituted with 0-2 R⁶ and is cyclopentane, cyclohexane, piperidine, dihydro-pyridine, tetrahydro-pyridine, pyridine, piperazine, tetrahydro-pyrazine, dihydro-pyrazine, pyrazine, dihydro-pyrimidine, tetrahydro-pyrimidine, hexahydro-pyrimidine, pyrazine, imidazole, dihydro-imidazole, imidazolidine, pyrazole, dihydro-pyrazole, or pyrazolidine; or
the ring CR⁴R⁵ or NR⁴R⁵ is optionally substituted with 0-2 R⁶ and is selected from the group consisting of:

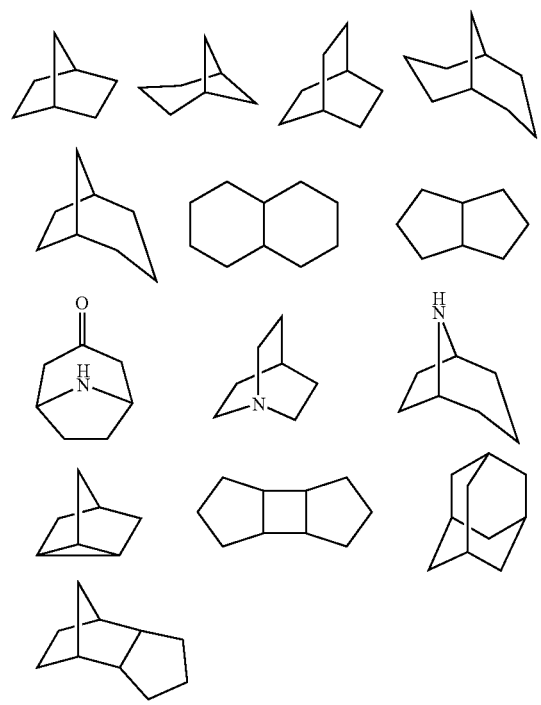

R⁶ is hydrogen, (C₁-C₈)alkyl, —ORᵃ, —CO₂Rᵃ, RᵇRᶜNC(=O)—, or aryl;
Rᵃ and Rᵇ are independently hydrogen, (C₃-C₄)-cycloalkyl, or (C₁-C₈)alkyl;
each R⁷ is independently hydrogen, (C₁-C₈)alkyl, aryl, aryl(C₁-C₈)alkylene, or heteroaryl(C₁-C₈)alkylene;
R⁸ is methyl, ethyl, propyl, 2-propenyl, cyclopropyl, cyclobutyl, cyclopropylmethyl, —(CH₂)₂CO₂CH₃, or —(CH₂)₂₋₃OH;
X is —CH₂ORᵃ, —CO₂Rᵃ, —CH₂OC(O)Rᵃ, or —C(O)NRᵇRᶜ; or
X is selected from:

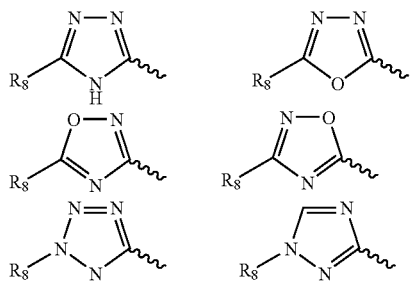

m is 0, 1, or 2;
or a pharmaceutically acceptable salt thereof.

3. The method of claim 2, wherein
R¹ is hydrogen, OH, OMe, or NH₂;
R² is hydrogen, methyl, ethyl or propyl;
R³ is hydrogen, OH, OMe, or NH₂;
the ring CR⁴R⁵ or NR⁴R⁵ is selected from the group consisting of:

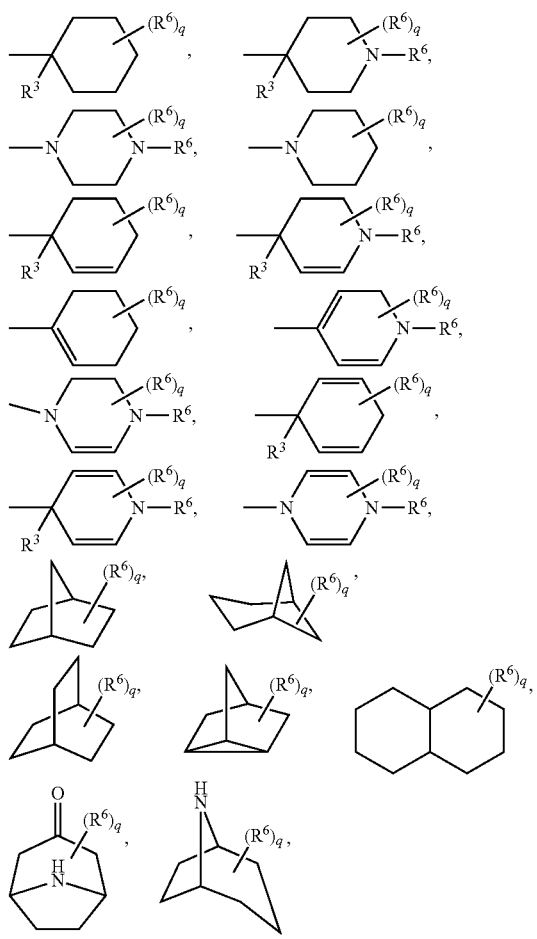

q is from 0 to 4;
R⁶ is hydrogen, (C₁-C₈)alkyl, —CO₂Rᵃ, —CO₂Rᵃ, RᵃC(=O)—, RᵃC(=O)O—, RᵇRᶜN—, RᵇRᶜNC(=O)—, or aryl;
Rᵃ and Rᵇ are independently hydrogen, methyl, ethyl, propyl, butyl, ethylhexyl, cyclopropyl, or cyclobutyl;
N(R⁷)₂ is amino, methylamino, dimethylamino; ethylamino; pentylamino, diphenylethylamino, (pyridinylmethyl)amino, (pyridinyl)(methyl)amino, diethylamino or benzylamino; and,
R⁸ is methyl, ethyl, propyl, or cyclopropyl;
X is —CH₂ORᵃ or —C(O)NRᵇRᶜ; or
X is selected from:

or a pharmaceutically acceptable salt thereof.

4. The method of claim 3, wherein:
R¹ is hydrogen, OH, or NH₂;
R² is hydrogen or methyl;
R³ is hydrogen, OH, or NH₂;
the ring CR⁴R⁵ or NR⁴R⁵ is selected from the group consisting of:

where q is from 0 to 2;
R⁶ is hydrogen, methyl, ethyl, t-butyl, phenyl, —CO₂Rᵃ— CONRᵇRᶜ, or RᵃC(=O)—;
Rᵇ is H;
Rᵃ is methyl, ethyl, propyl, butyl, pentyl, ethylhexyl cyclopropyl, or cyclobutyl; —N(R⁷)₂ is amino, methylamino, dimethylamino; ethylamino; diethylamino or benzylamino;
or a pharmaceutically acceptable salt thereof.

5. The method of claim 4, wherein:
R¹ is hydrogen or OH;
R² is hydrogen;
R³ is hydrogen or OH;
the ring CR⁴R⁵ or NR⁴R⁵ is selected from the group consisting of:

R⁶ is hydrogen, methyl, ethyl, —CO₂Rᵃ, or —CONRᵇRᶜ;
Rᵇ is H;
Rᵃ is methyl, ethyl, i-propyl, i-butyl, tert-butyl, or cyclopropyl;
N(R⁷)₂ is amino, or methylamino;
X is —CH₂OH, C(O)NHCH₃, or —C(O)NHCH₂CH₃;
or a pharmaceutically acceptable salt thereof.

6. The method of claim 1, wherein the ring comprising R⁴ and R⁵ is 2-methyl cyclohexane, 2,2-dimethylcyclohexane, 2-phenyl cyclohexane, 2-ethylcyclohexane, 2,2-diethylcyclohexane, 2-tert-butyl cyclohexane, 3-methyl cyclohexane, 3,3-dimethylcyclohexane, 4-methyl cyclohexane, 4-ethylcyclohexane, 4-phenyl cyclohexane, 4-tert-butyl cyclohexane, 4-carboxymethyl cyclohexane, 4-carboxyethyl cyclohexane, 3,3,5,5-tetramethyl cyclohexane, 2,4-dimethyl cyclopentane, 4-cyclohexanecarboxylic acid, 4-cyclohexanecarboxylic acid esters, 4-methyloxyalkanoyl-cyclohexane, 4-piperidine-1-carboxylic acid methyl ester, 4-piperidine-1-carboxylic acid tert-butyl ester, 4-piperidine, 4-piperazine-1-carboxylic acid methyl ester, 4-piperidine-1-carboxylic acid tert-butylester, 1-piperidine-4-carboxylic acid methyl ester, 1-piperidine-4-carboxylic acid tert-butyl ester, tert-butylester, 1-piperidine-4-carboxylic acid methyl ester, or 1-piperidine-4-carboxylic acid tert-butyl ester, 3-piperidine-1-carboxylic acid methyl ester, 3-piperidine-1-carboxylic acid tert-butyl ester, 3-piperidine, 3-piperazine-1-carboxylic acid methyl ester, 3-piperidine-1-carboxylic acid tert-butylester, 1-piperidine-3-carboxylic acid methyl ester, or 1-piperidine-3-carboxylic acid tert-butyl ester;

or a pharmaceutically acceptable salt thereof.

7. The method of claim 1, wherein the $A_{2A}$ adenosine receptor agonist is

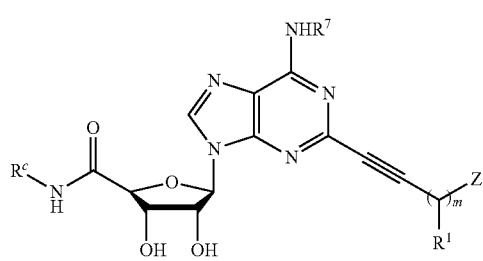

wherein $R^c$ is Et; $R_7$ is H and —$(R^1CH)_m$—Z is selected from the group consisting of:

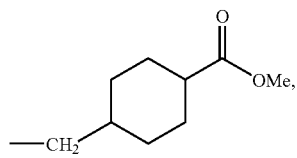

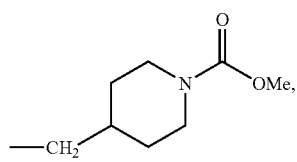

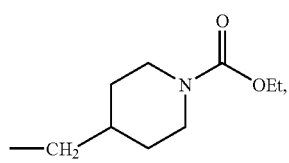

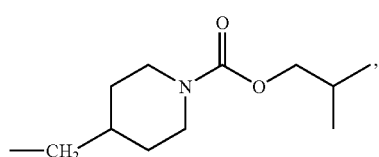

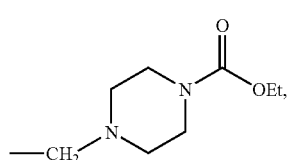

-continued

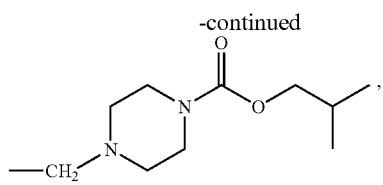

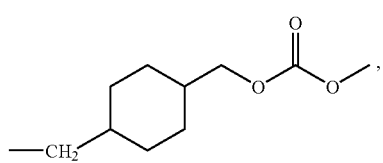

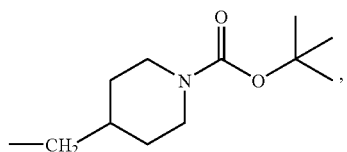

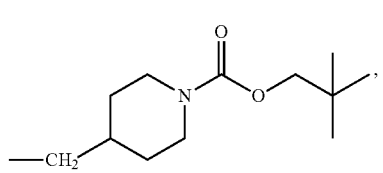

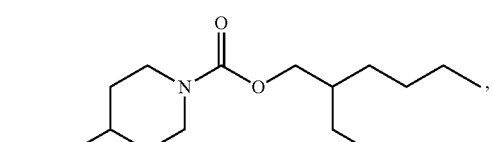

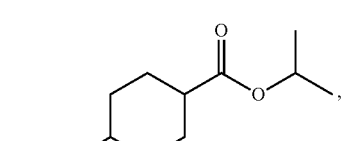

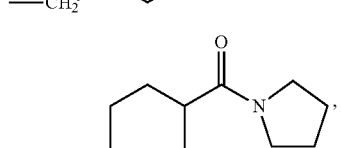

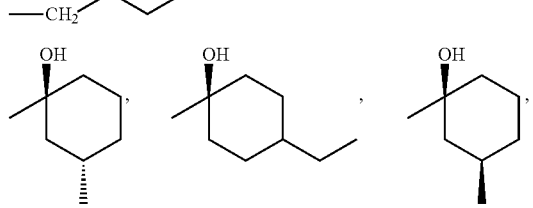

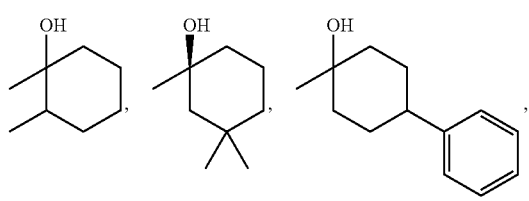

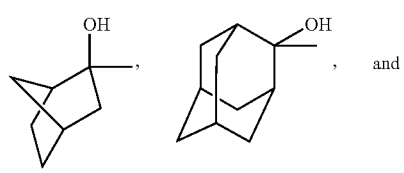

and

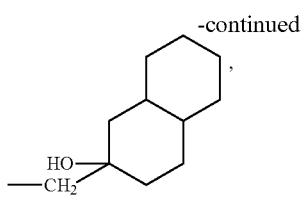

or a pharmaceutically acceptable salt thereof.

8. The method of claim 1, wherein the $A_{2A}$ adenosine receptor agonist is

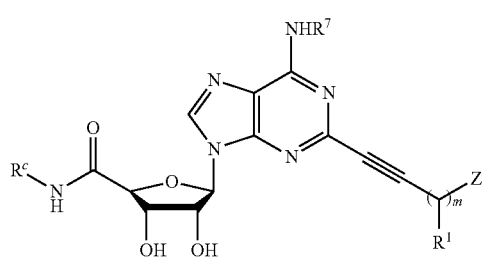

wherein $R^c$ is cPr; $R_7$ is H and —$(R^1CH)_m$—Z is selected from the group consisting of:

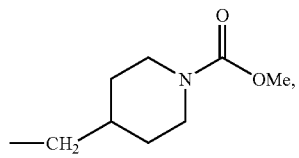

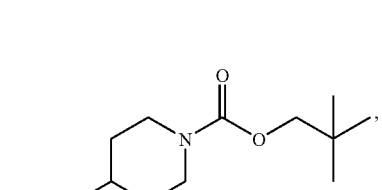

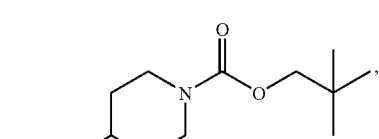

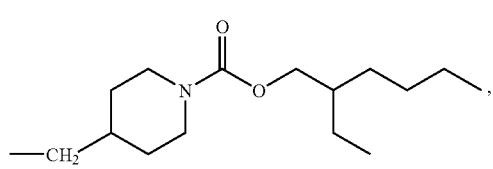

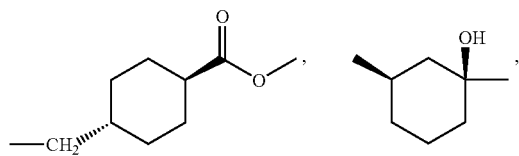

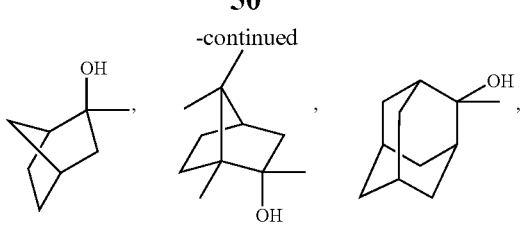

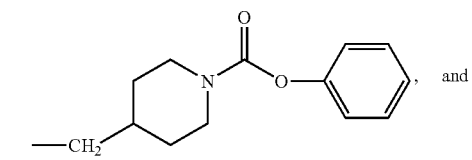

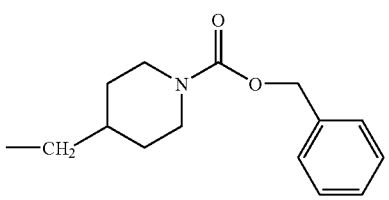

or a pharmaceutically acceptable salt thereof.

9. The method of claim 7, wherein $R^c$ is Et, $R^7$ is H and —$(R^1CH)_m$—Z is

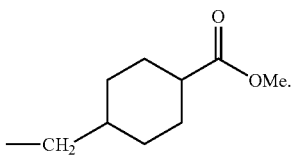

10. The method of claim 1, wherein the $A_{2A}$ adenosine receptor agonist is formula (Ib)-(Id) or a pharmaceutically acceptable salt thereof:

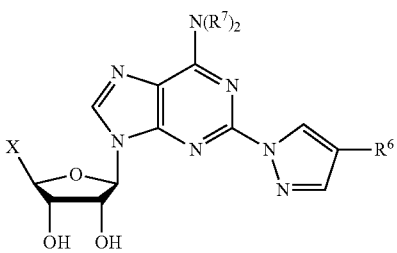

(Ib)

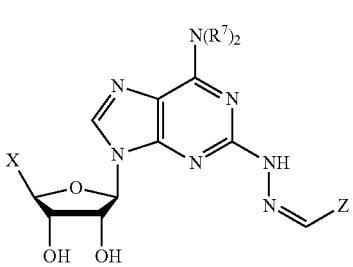

(Ic)

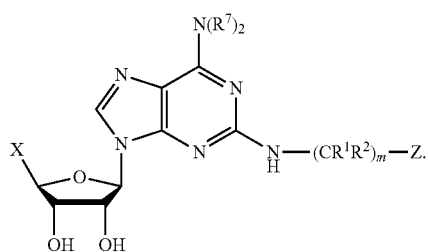
11. The method of claim 10, wherein the $A_{2A}$ adenosine receptor agonist is selected from:
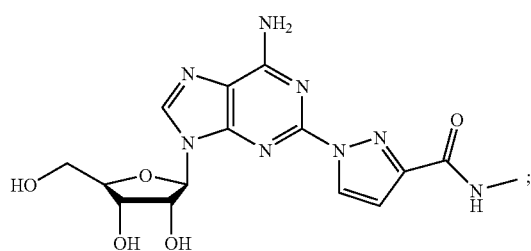
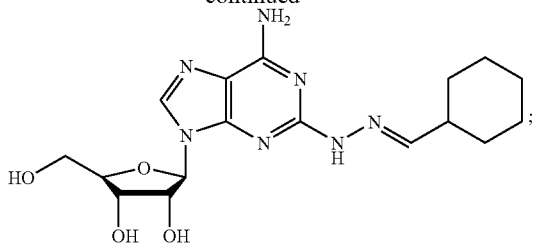
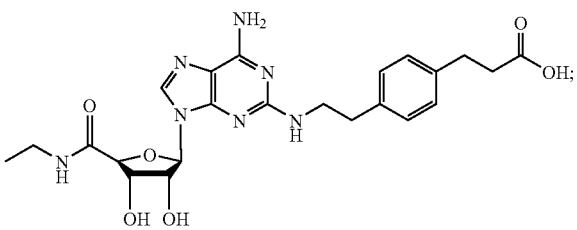
or a pharmaceutically acceptable salt thereof.
* * * * *